(12) United States Patent
Saxty et al.

(10) Patent No.: US 8,722,687 B2
(45) Date of Patent: *May 13, 2014

(54) IMIDAZO [1,2-A]PYRIDINE DERIVATIVES AS FGFR KINASE INHIBITORS FOR USE IN THERAPY

(75) Inventors: Gordon Saxty, Cambridge (GB); Valerio Berdini, Cambridge (GB); Christopher William Murray, Cambridge (GB); Eddy Jean Edgard Freyne, Rumst (BE); Yannick Aimé Eddy Ligny, Sotteville-lès Rouen (FR); Pascal Ghislain André Bonnet, Berchem (BE); Berthold Wroblowski, Vosselaar (BE); Alexandra Papanikos, Antwerp (BE)

(73) Assignee: Astex Therapeutics Ltd, Cambridge (GB)

(*) Notice: Subject to any disclaimer, the term of this patent is extended or adjusted under 35 U.S.C. 154(b) by 248 days.

This patent is subject to a terminal disclaimer.

(21) Appl. No.: 13/264,596

(22) PCT Filed: Apr. 15, 2010

(86) PCT No.: PCT/GB2010/050618
§ 371 (c)(1),
(2), (4) Date: Oct. 14, 2011

(87) PCT Pub. No.: WO2010/119285
PCT Pub. Date: Oct. 21, 2010

(65) Prior Publication Data
US 2012/0041000 A1 Feb. 16, 2012

Related U.S. Application Data

(60) Provisional application No. 61/169,503, filed on Apr. 15, 2009.

(30) Foreign Application Priority Data

Apr. 15, 2009 (GB) .................................. 0906470.0

(51) Int. Cl.
| | |
|---|---|
| *C07D 239/42* | (2006.01) |
| *C07D 401/04* | (2006.01) |
| *A61K 31/44* | (2006.01) |
| *A01N 43/42* | (2006.01) |
| *C07D 513/02* | (2006.01) |
| *C07D 515/02* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 413/00* | (2006.01) |

(52) U.S. Cl.
USPC ............ 514/256; 514/300; 546/121; 544/333

(58) Field of Classification Search
USPC .................... 514/256, 300; 546/121; 544/333
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,554,630 A | 9/1996 | Teuber et al. | |
| 5,882,864 A | 3/1999 | An et al. | |
| 5,990,146 A | 11/1999 | Boschelli et al. | |
| 6,218,529 B1 | 4/2001 | An et al. | |
| 6,465,484 B1 | 10/2002 | Bilodeau et al. | |
| 6,498,165 B1 | 12/2002 | Armstrong et al. | |
| 6,855,719 B1 | 2/2005 | Thomas et al. | |
| 7,074,801 B1 | 7/2006 | Yoshida et al. | |
| 8,071,614 B2 | 12/2011 | Saxty et al. | |
| 8,076,354 B2 | 12/2011 | Saxty et al. | |
| 8,131,527 B1 | 3/2012 | Saxty et al. | |
| 8,481,531 B2 | 7/2013 | Saxty et al. | |
| 2002/0041880 A1 | 4/2002 | DeFeo-Jones et al. | |
| 2003/0203897 A1 | 10/2003 | Love et al. | |
| 2004/0019210 A1 | 1/2004 | Chivikas Connolly et al. | |
| 2004/0067948 A1 | 4/2004 | Hallett | |
| 2004/0220189 A1 | 11/2004 | Sun et al. | |
| 2004/0267510 A1 | 12/2004 | Bemis et al. | |
| 2006/0035921 A1 | 2/2006 | Castelhano et al. | |
| 2006/0089362 A1 | 4/2006 | Seno et al. | |

(Continued)

FOREIGN PATENT DOCUMENTS

| | | |
|---|---|---|
| EP | 1382603 A1 | 1/2004 |
| EP | 1724258 A1 | 11/2006 |

(Continued)

OTHER PUBLICATIONS

Lee et al., Nature reviews/cancer, vol. 8, (2008), pp. 579-591.*
Search Report for GB0625827.1 dated Apr. 25, 2007.
Search Report for GB0719998.7 dated Nov. 12, 2007.
Search Report for PCT/GB2007/004960 dated Sep. 22, 2008.
Search Report for GB0625826.3 dated Apr. 25, 2007.
Search Report for GB0720000.9 dated Nov. 12, 2007.
Search Report for PCT/GB2007/004934 dated May 6, 2008.
Search Report for GB0810902.7 dated Sep. 17, 2008.
Search Report for PCT/EP2009/057318 dated Oct. 12, 2009.
Search Report for GB0720038.9 dated Apr. 17, 2008.
Search Report for PCT/GB2008/003439 dated Jan. 29, 2009.

(Continued)

*Primary Examiner* — Niloofar Rahmani
(74) *Attorney, Agent, or Firm* — Heslin Rothenberg Farley & Mesiti P.C.

(57) ABSTRACT

The invention relates to new bicyclic heterocyclyl derivatives of formula (I), to pharmaceutical compositions comprising said compounds and to the use of said compounds in the treatment of diseases, e.g. cancer.

20 Claims, No Drawings

(56) References Cited

U.S. PATENT DOCUMENTS

| | | |
|---|---|---|
| 2006/0116402 A1 | 6/2006 | Crew et al. |
| 2006/0189629 A1 | 8/2006 | Bolger et al. |
| 2007/0185140 A1 | 8/2007 | Bordon-Pallier et al. |
| 2008/0139606 A1 | 6/2008 | Tabart et al. |
| 2008/0167314 A1 | 7/2008 | Uchikawa et al. |
| 2012/0208791 A1* | 8/2012 | Berdini et al. ......... 514/210.18 |

FOREIGN PATENT DOCUMENTS

| | | |
|---|---|---|
| EP | 1748048 A1 | 1/2007 |
| EP | 1790650 A1 | 5/2007 |
| EP | 1882475 A1 | 1/2008 |
| EP | 2116543 A1 | 11/2009 |
| JP | 2001-057292 | 2/2001 |
| JP | 2004-002826 | 1/2004 |
| WO | 95/35296 A1 | 12/1995 |
| WO | 96/34866 A1 | 11/1996 |
| WO | 97/12613 A1 | 4/1997 |
| WO | 98/03510 A1 | 1/1998 |
| WO | 98/54093 A1 | 12/1998 |
| WO | 99/38868 A1 | 8/1999 |
| WO | 00/12089 A1 | 3/2000 |
| WO | 00/53605 A1 | 9/2000 |
| WO | 01/00207 A1 | 1/2001 |
| WO | 01/00213 A1 | 1/2001 |
| WO | 01/00214 A1 | 1/2001 |
| WO | 01/14375 A1 | 3/2001 |
| WO | 01/18000 A1 | 3/2001 |
| WO | 01/21634 A1 | 3/2001 |
| WO | 01/38326 A2 | 5/2001 |
| WO | 01/66098 A2 | 9/2001 |
| WO | 02/12238 A2 | 2/2002 |
| WO | 02/34748 A1 | 5/2002 |
| WO | 02/38569 A1 | 5/2002 |
| WO | 02/46168 A1 | 6/2002 |
| WO | 02/066477 A2 | 8/2002 |
| WO | 02/066478 A1 | 8/2002 |
| WO | 02/066480 A2 | 8/2002 |
| WO | 02/066481 A1 | 8/2002 |
| WO | 02/074773 A1 | 9/2002 |
| WO | 02/080914 A2 | 10/2002 |
| WO | 03/007955 A2 | 1/2003 |
| WO | 03/048132 A1 | 6/2003 |
| WO | 03/050117 A1 | 6/2003 |
| WO | 03/050119 A2 | 6/2003 |
| WO | 03/082208 A2 | 10/2003 |
| WO | 03/088208 A2 | 10/2003 |
| WO | 03/092595 A2 | 11/2003 |
| WO | 03/099811 A1 | 12/2003 |
| WO | 03/099816 A1 | 12/2003 |
| WO | 03/099817 A1 | 12/2003 |
| WO | 03/101993 A1 | 12/2003 |
| WO | 2004/026867 A2 | 4/2004 |
| WO | 2004/035579 A1 | 4/2004 |
| WO | 2004/052286 A2 | 6/2004 |
| WO | 2004/052315 A2 | 6/2004 |
| WO | 2004/087153 A2 | 10/2004 |
| WO | 2005/021531 A1 | 3/2005 |
| WO | 2005/021544 A2 | 3/2005 |
| WO | 2005/054230 A1 | 6/2005 |
| WO | 2005/075470 A1 | 8/2005 |
| WO | 2006/000420 A1 | 1/2006 |
| WO | 2006/034402 A2 | 3/2006 |
| WO | 2006/038001 A1 | 4/2006 |
| WO | 2006/070198 A1 | 7/2006 |
| WO | 2006/070943 A1 | 7/2006 |
| WO | 2006/091671 A1 | 8/2006 |
| WO | 2006/094235 A1 | 9/2006 |
| WO | 2006/108103 A1 | 10/2006 |
| WO | 2006/135667 A1 | 12/2006 |
| WO | 2007/036732 A1 | 4/2007 |
| WO | 2007/109362 A2 | 9/2007 |
| WO | 2007/112093 A2 | 10/2007 |
| WO | 2008/003511 A1 | 1/2008 |
| WO | 2008/008747 A1 | 1/2008 |
| WO | 2008/075068 A2 | 6/2008 |
| WO | 2008/078091 A1 | 7/2008 |
| WO | 2008/078100 A2 | 7/2008 |
| WO | 2008/081910 A1 | 7/2008 |
| WO | 2008/124323 A1 | 10/2008 |
| WO | 2008/154642 A2 | 12/2008 |
| WO | 2009/002534 A1 | 12/2008 |
| WO | 2009/047506 A1 | 4/2009 |
| WO | 2009/047522 A1 | 4/2009 |
| WO | 2009/150240 A1 | 12/2009 |
| WO | 2010/119284 A1 | 10/2010 |
| WO | 2010/119285 A1 | 10/2010 |

OTHER PUBLICATIONS

Search Report for GB0720041.3 dated Apr. 17, 2008.
Search Report for PCT/GB2008/003418 dated Jan. 29, 2009.
Search Report for GB0906472.6 dated Jul. 7, 2009.
Search Report for PCT/GB2010/050617 dated Jul. 20, 2010.
Search Report for GB0906470.0 dated Jul. 8, 2009.
Search Report for PCT/GB2010/050618 dated Jul. 23, 2010.
Bilodeau, Mark T. et al., Design and Synthesis of 1,5-Dairylbenzimidazoles as Inhibitors of the VEGF-Receptor KDR, Bioorganic & Medicinal Chemistry Letters 13, 2003, pp. 2485-2488.
Clark, Michael P. et al., Development of new pyrrolopyrimidine-based inhibitors of Janus kinase 3 (JAK3), Bioorganic & Medicinal Chemistry Letters 17 (5), 2007, pp. 1250-1253.
Wermuth, Camille G., Molecular Variations Based on Isosteric Replacements, The Practice of Medicinal Chemistry, 1996, pp. 203-237.
Fraley, Mark E. et al., Synthesis and Initial SAR Studies of 3,6-Disubstituted Pyrazolo[1,5-α]pyrimidines: A New Class of KDR Kinase Inhibitors, Bioorganic & Medicinal Chemistry Letters 12, 2002, pp. 2767-2770.
Wu, Zhicai et al., Design and Synthesis of 3,7-diarylimidazopyridines as inhibitors of the VEGF-receptor KDR, Bioorganic & Medicinal Chemistry Letters 14, 2004, pp. 909-912.
Fraley, Mark E. et al., Optimization of a Pyrazolo[1,5-α]pyrimidine Class of KDR Kinase Inhibitors: Improvements in Physical Properties Enhance Cellular Activity and Pharmacokinetics, Bioorganic & Medicinal Chemistry Letters 12, 2002, pp. 3537-3541.
Skaper, Stephen D. et al., The FGFR1 Inhibitor PD 173074 Selectively and Potently Antagonizes FGF-2 Neurotrophic and Neurotropic Effects, Journal of Neurochemistry, 2000, pp. 1520-1527.
Mohammadi, Moosa et al., Crystal structure of an angiogenesis inhibitor bound to the FGR receptor tyrosine kinase domain, The EMBO Journal, vol. 17, No. 20, 1998, pp. 5896-5904.
Connolly, Cleo J.C. et al., Discovery and Structure-Activity Studies of a Novel Series of Pyrido[2,3-d]Pyrimidine Tyrosine Kinase Inhibitors, Bioorganic & Medicinal Chemistry Letters, vol. 7, No. 18, 1997, pp. 2415-2420.
Hamby, James M. et al., Structure-Activity Relationships for a Novel Series of Pyrido[2,3-d]pyrimidine Tyrosine Kinase Inhibitors, J. Med. Chem, 40, 1997, pp. 2296-2303.
Scribner, Andrew et al., Synthesis and biological activity of imidazopyridine anticoccidial agents: Part I, European Journal of Medicinal Chemistry 42, 2007, pp. 1334-1357.
Anderson, Malcolm et al., Imidazo[1,2-α]pyridines: A Potent and Selective Class of Cyclin-Dependent Kinase Inhibitors Identified Through Structure-Based Hybridisation, Bioorganic & Medicinal Chemistry Letters 13, 2003, pp. 3021-3026.
Mohammadi, Moosa et al., Structures of the Tyrosine Kinase Domain of Fibroblast Growth Factor Receptor in Complex with Inhibitors, Science, 276, 1997, pp. 955-960.
Dorwald, F. Zaragoza, Side Reactions in Organic Synthesis, 2005, Wiley: VCH, Weinheim p. IX of Preface.
Vippagunta, Sudha R., et al., Crystalline solids, Advanced Drug Delivery Reviews 48, 2001, pp. 3-26.
West, Anthony R., Solid state chemistry and its applications, Department of Chemistry, University of Aberdeen, 1988, pp. 358 and 365.
Hamdi et al. "Solvates of Indomethacin"; *Journal of Thermal Analysis and Calorimetry*; 2004; pp. 985-1001; vol. 76.

(56) References Cited

OTHER PUBLICATIONS

Morissette et al. "High-throughput crystallization: polymorphs, salts, co-crystals and solvates of pharmaceutical solids"; *Advanced Drug Delivery Reviews*; 2004; pp. 275-300; vol. 56.
Palmer, Brian D., et al. "Structure-Activity Relationships for 1-Phenylbenzimidazoles as Selective ATP Site Inhibitors of the Platelet-Derived Growth Factor Receptor" *Journal of Medicinal Chemistry*, 1998, 41 (27), pp. 5457-5465.
Berge, Stephen M. et al. "Pharmaceutical Salts", *Journal of Pharmaceutical Sciences*, vol. 66, No. 1, 1977, pp. 1-19.
Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.
Angerer, Lynne M. et al. "Demonstration of Tissue-Specific Gene Expression by in Situ Hybridization", *Methods in Enzymology*, vol. 152, 1987, pp. 649-661.
Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.
Orre, Maxine and Rogers, Peter A.W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

* cited by examiner

IMIDAZO [1,2-A]PYRIDINE DERIVATIVES AS FGFR KINASE INHIBITORS FOR USE IN THERAPY

CROSS REFERENCE TO RELATED APPLICATIONS

This application is a national stage filing under section 371 of International Application No. PCT/GB2010/050618, filed on Apr. 15, 2010, and published in English on Oct. 21, 2010, as WO 2010/119285, and claims priority to British Application No. 0906470.0, filed on Apr. 15, 2009, and to U.S. Provisional Application No. 61/169,503, filed on Apr. 15, 2009. The entire disclosures of each of the prior applications are hereby incorporated herein by reference.

FIELD OF THE INVENTION

The invention relates to new bicyclic heterocyclyl derivative compounds, to pharmaceutical compositions comprising said compounds and to the use of said compounds in the treatment of diseases, e.g. cancer.

SUMMARY OF THE INVENTION

According to a first aspect of the invention there is provided a compound of formula (I):

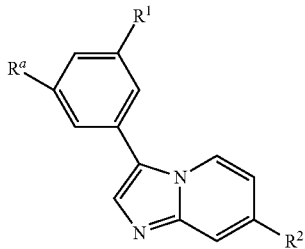

(I)

wherein
$R^1$ represents —NHCONR$^4$R$^5$ or —NHCSNR$^4$R$^5$ or —NH-heterocyclyl wherein heterocyclyl represents thiadiazolyl or oxadiazolyl, and wherein the heterocyclyl group is optionally substituted by one or more (e.g. 1, 2 or 3) halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^d$, —(CH$_2$)$_n$—O—$C_{1-6}$ alkyl, —O—(CH$_2$)$_n$—OR$^d$, halo$C_{1-6}$ alkyl, halo$C_{1-6}$ alkoxy, $C_{1-6}$ alkanol, =O, =S, nitro, Si(R$^d$)$_4$, —(CH$_2$)$_s$—CN, —S—R$^d$, —SO—R$^d$, —SO$_2$—R$^d$, —COR$^d$, —(CR$^d$R$^e$)$_s$—COOR$^f$, —(CH$_2$)$_s$—CONR$^d$R$^e$, —(CH$_2$)$_s$—NR$^d$R$^e$, —(CH$_2$)$_s$—NR$^d$COR$^e$, —(CH$_2$)$_s$—NR$^d$SO$_2$—R$^e$, —(CH$_2$)$_s$—NH—SO$_2$—NR$^d$R$^e$, —OCONR$^d$R$^e$, —(CH$_2$)$_s$—NR$^d$CO$_2$R$^e$, —O—(CH$_2$)$_s$—CR$^d$R$^e$—(CH$_2$)$_t$—OR$^f$ or —(CH$_2$)$_s$—SO$_2$NR$^d$R$^e$ groups;
$R^a$ represents $C_{2-4}$alkoxy, halo$C_{2-4}$alkoxy, $C_{1-4}$alkoxy $C_{1-4}$alkyl, cyclobutoxy, cyclopropoxy, —CH—$C_{1-4}$alkyl, —N(C$_{1-4}$alkyl)$_2$, —$C_{1-4}$alkyl-NH(C$_{1-4}$alkyl), —C$_{1-4}$alkyl-N(C$_{1-4}$alkyl)$_2$, —C$_{1-4}$alkyl-S(=O)$_2$—C$_{1-4}$alkyl or —S(=O)$_2$—C$_{1-4}$alkyl;

$R^2$ represents —C(=O)—R$^x$, —O—R$^x$ or a 5 or 6-membered heterocyclyl optionally substituted by one or more (e.g. 1, 2 or 3) halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^g$, —(CH$_2$)$_n$—O—$C_{1-6}$ alkyl, —O—(CH$_2$)$_n$—OR$^g$, halo$C_{1-6}$ alkyl, halo$C_{1-6}$ alkoxy, $C_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_s$—SO$_2$NR$^g$R$^h$ groups;
$R^x$ represents $C_{3-6}$cycloalkyl optionally substituted with hydroxyl or NR'R", or $C_{1-6}$alkyl optionally substituted with hydroxyl or NR'R";
R' and R" each independently represent hydrogen, $C_{1-4}$alkyl or R' and R" taken together with the nitrogen to which they are attached may form a saturated heterocycle selected from piperidinyl, piperazinyl, morpholinyl or thiomorpholinyl;
$R^4$ and $R^5$ each independently represent hydrogen, $C_{1-6}$ alkyl, $C_{2-6}$ alkenyl, $C_{2-6}$ alkynyl, cycloalkyl, $C_{3-8}$ cycloalkenyl, $C_{1-6}$ alkanol, halo$C_{1-6}$ alkyl, —(CH$_2$)$_n$—NR$^g$R$^h$, —(CH$_2$)$_s$—COOR$^k$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^p$ groups;
$R^p$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^g$, —(CH$_2$)$_n$—O—$C_{1-6}$ alkyl, —O—(CH$_2$)$_n$—OR$^g$, halo$C_{1-6}$ alkyl, halo$C_{1-6}$ alkoxy, $C_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_5$—SO$_2$NR$^g$R$^h$ groups;
$R^d$, $R^e$ and $R^f$ independently represent hydrogen, $C_{1-6}$ alkyl, $C_{2-6}$ alkenyl, $C_{2-6}$ alkynyl, $C_{1-6}$ alkanol, hydroxy, $C_{1-6}$alkoxy, halo$C_{1-6}$ alkyl, —CO—(CH$_2$), —$C_{1-6}$alkoxy, $C_{3-8}$ cycloalkyl, $C_{3-8}$ cycloalkenyl;
$R^g$, $R^h$ and $R^k$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$alkoxy, halo$C_{1-6}$ alkyl, —CO—(CH$_2$)$_n$—$C_{1-6}$alkoxy, $C_{1-6}$alkylamino-, $C_{3-8}$ cycloalkyl, $C_{3-8}$ cycloalkenyl;
m and n independently represent an integer from 1-4;
s and t independently represent an integer from 0-4;
or a pharmaceutically acceptable salt, solvate or derivative thereof.

WO 2008/078100 (Astex), WO 2008/078091 (Astex), WO 2009/047522 (Astex), WO 2009/047506 (Astex), WO2009/150240 (Astex), U.S. Pat. No. 7,074,801 (Eisai), WO 2006/091671 (Eli Lilly), WO 2003/048132 (Merck), WO 2006/135667 (BMS), WO 2005/080330 (Chugai), WO 2006/094235 (Sirtris Pharmaceuticals) and WO 2006/034402 (Synta Pharmaceuticals) each disclose a series of heterocyclyl derivatives.

DETAILED DESCRIPTION OF THE INVENTION

According to a first aspect of the invention there is provided a compound of formula (I):

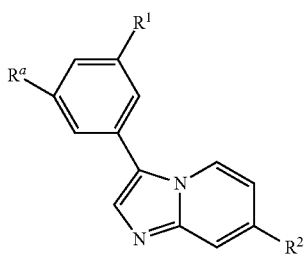

(I)

wherein $R^1$ represents —NHCONR$^4$R$^5$ or —NHCSNR$^4$R$^5$ or —NH-heterocyclyl wherein heterocyclyl represents thiadiazolyl or oxadiazolyl, and wherein the heterocyclyl group is optionally substituted by one or more (e.g. 1, 2 or 3) halogen, $C_{1-6}$ alkyl, $C_{2-6}$ alkenyl, $C_{2-6}$ alkynyl, $CO_{3-8}$ cycloalkyl, $C_{3-8}$ cycloalkenyl, —OR$^d$, —(CH$_2$)$_n$—O—C$_{1-6}$ alkyl, —O—(CH$_2$)—OR$^d$, haloC$_{1-6}$ alkyl, haloC$_{1-6}$ alkoxy, C$_{1-6}$ alkanol, =O, =S, nitro, Si(R$^d$)$_4$, —(CH$_2$)$_s$—CN, —S—R$^d$, —SO—R$^d$, —SO$_2$—R$^d$, —COR$^d$, —(CR$^d$R$^e$)$_s$—COOR$^f$, —(CH$_2$)$_s$—CONR$^d$R$^e$, —(CH$_2$)$_s$—NR$^d$R$^e$, —(CH$_2$)$_s$—NR$^d$COR$^e$, —(CH$_2$)$_s$—NR$^d$SO$_2$—R$^e$, —(CH$_2$)$_s$—NH—SO$_2$—NR$^d$R$^e$, —OCONR$^d$R$^e$, —(CH$_2$)$_s$—NR$^d$CO$_2$R$^e$, —O—(CH$_2$)$_s$—CR$^d$R$^e$—(CH$_2$)$_t$—OR$^f$ or —(CH$_2$)$_s$—SO$_2$NR$^d$R$^e$ groups;

R$_a$ represents C$_{2-4}$alkoxy, haloC$_{2-4}$alkoxy, C$_{1-4}$alkoxy C$_{1-4}$alkyl, cyclobutoxy, cyclopropoxy, —N(C$_{1-4}$alkyl)$_2$, —C$_{1-4}$alkyl-NH(C$_{1-4}$alkyl), —C$_{1-4}$alkyl-N(C$_{1-4}$alkyl)$_2$, C$_{1-4}$alkyl-S(=O)$_2$—C$_{1-4}$alkyl or —S(=O)$_2$—C$_{1-4}$alkyl;

$R^2$ represents —C(=O)—R$^x$, —O—R$^x$ or a 5 or 6-membered heterocyclyl optionally substituted by one or more (e.g. 1, 2 or 3) halogen, C$_{1-6}$ alkyl, C$_{2-6}$ alkenyl, C$_{2-6}$ alkynyl, C$_{3-5}$ cycloalkyl, C$_{3-5}$ cycloalkenyl, —OR$^g$, —(CH$_2$)$_n$—O—C$_{1-6}$ alkyl, —O—(CH$_2$)$_n$—OR$^g$, haloC$_{1-6}$ alkyl, haloC$_{1-6}$ alkoxy, C$_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_s$—SO$_2$NR$^g$R$^h$ groups;

$R^x$ represents C$_{3-6}$cycloalkyl optionally substituted with hydroxyl or NR'R", or C$_{1-6}$alkyl optionally substituted with hydroxyl or NR'R";

R' and R" each independently represent hydrogen, C$_{1-4}$alkyl or R' and R" taken together with the nitrogen to which they are attached may form a saturated heterocycle selected from piperidinyl, piperazinyl, morpholinyl or thiomorpholinyl;

$R^4$ and $R^5$ each independently represent hydrogen, C$_{1-6}$ alkyl, C$_{2-6}$ alkenyl, C$_{2-6}$ alkynyl, C$_{3-8}$ cycloalkyl, C$_{3-8}$ cycloalkenyl, C$_{1-6}$ alkanol, haloC$_{1-6}$ alkyl, —(CH$_2$)$_n$—NR$^g$R$^h$, —(CH$_2$)$_s$COOR$^k$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said C$_{1-6}$ alkyl, C$_{2-6}$ alkenyl, C$_{2-6}$ alkynyl, C$_{3-8}$ cycloalkyl, C$_{3-8}$ cycloalkenyl, aryl and heterocyclyl groups may be optionally substituted by one or more (e.g. 1, 2 or 3) R$^p$ groups;

R$^p$ represents halogen, C$_{1-6}$ alkyl, C$_{2-5}$ alkenyl, C$_{2-6}$ alkynyl, C$_{3-8}$ cycloalkyl, C$_{3-8}$ cycloalkenyl, —OR$^g$, —(CH$_2$)$_n$—O—C$_{1-6}$ alkyl, —O—(CH$_2$)$_n$—OR$^g$, haloC$_{1-6}$ alkyl, haloC$_{1-6}$ alkoxy, C$_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_s$—SO$_2$NR$^g$R$^h$ groups;

R$^d$, R$^e$ and R$^f$ independently represent hydrogen, C$_{1-6}$ alkyl, C$_{2-6}$ alkenyl, C$_{2-6}$ alkynyl, C$_{1-6}$ alkanol, hydroxy, C$_{1-6}$alkoxy, haloC$_{1-6}$ alkyl, —CO—(CH$_2$)$_n$—C$_{1-6}$alkoxy, C$_{3-8}$ cycloalkyl, C$_{3-8}$ cycloalkenyl;

R$^g$, R$^h$ and R$^k$ independently represent hydrogen, C$_{1-6}$ alkyl, C$_{2-6}$ alkenyl, C$_{2-6}$ alkynyl, C$_{1-6}$ alkanol, —COOC$_{1-6}$ alkyl, hydroxy, C$_{1-6}$alkoxy, haloC$_{1-6}$ alkyl, —CO—(CH$_2$)$_n$—C$_{1-6}$alkoxy, C$_{1-6}$alkylamino-, C$_{3-8}$ cycloalkyl, C$_{3-8}$ cycloalkenyl;

m and n independently represent an integer from 1-4;
s and t independently represent an integer from 0-4;
or a pharmaceutically acceptable salt, solvate or derivative thereof.

The terms 'C$_{1-6}$ alkyl', 'C$_{1-4}$ alkyl' or 'C$_{2-4}$ alkyl' as used herein as a group or a part of the group refers to a linear or branched saturated hydrocarbon group containing from 1 to 6, from 1 to 4 or from 2 to 4, carbon atoms respectively. Examples of such groups include methyl, ethyl, n-propyl, isopropyl, n-butyl, isobutyl, sec-butyl, tert butyl, n-pentyl, isopentyl, neopentyl or hexyl and the like.

The term 'C$_{2-6}$ alkenyl' as used herein as a group or a part of the group refers to a linear or branched hydrocarbon group containing from 2 to 6 carbon atoms and containing a C=C bond.

The terms 'C$_{1-6}$ alkoxy', 'C$_{1-4}$ alkoxy' or 'C$_{2-4}$ alkoxy' used herein refer to an —O—C$_{1-6}$ alkyl group wherein C$_{1-6}$ alkyl is as defined herein, an —O—C$_{1-4}$ alkyl group wherein C$_{1-4}$ alkyl is as defined herein or an —O—C$_{2-4}$ alkyl group wherein C$_{2-4}$ alkyl is as defined herein. Examples of such groups include methoxy, ethoxy, propoxy, butoxy, pentoxy or hexoxy and the like.

The term 'C$_{1-6}$ alkanol' as used herein refers to a C$_{1-6}$ alkyl group substituted by one or more hydroxy groups, wherein C$_{1-6}$ alkyl is as defined herein. Examples of such groups include hydroxymethyl, hydroxyethyl, hydroxypropyl and the like.

The term 'C$_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'C$_{3-6}$ cycloalkyl' as used herein refers to a saturated monocyclic hydrocarbon ring of 3 to 6 carbon atoms. Examples of such groups include cyclopropyl, cyclobutyl, cyclopentyl, cyclohexyl, and the like.

The term 'halogen' as used herein refers to a fluorine, chlorine, bromine or iodine atom.

The term 'haloC$_{1-6}$ alkyl' as used herein refers to a C$_{1-6}$ alkyl group as defined herein wherein at least one hydrogen atom is replaced with halogen. Examples of such groups include fluoroethyl, trifluoromethyl or trifluoroethyl and the like.

The term 'haloC$_{1-6}$ alkoxy' or 'haloC$_{2-4}$ alkoxy' as used herein refers to a C$_{1-6}$ alkoxy group as herein defined or a C$_{2-4}$ alkoxy as herein defined wherein at least one hydrogen atom is replaced with halogen. Examples of such groups include difluoromethoxy or trifluoromethoxy and the like.

The term 'C$_{1-4}$ alkoxy C$_{1-4}$ alkyl" as used herein refers to a C$_{1-4}$ alkyl group as herein defined wherein at least one hydrogen atom is replaced with a C$_{1-4}$ alkoxy group as herein defined. Examples of such groups include methoxymethyl (—CH$_2$—O—CH$_3$), ethoxymethyl (—CH$_2$—O—CH$_2$—CH$_3$), and methoxyethyl (—CH$_2$—CH$_2$—O—CH$_3$) and the like.

The term "aryl" as used herein refers to a cyclic hydrocarbon group having aromatic character. The term "aryl"

embraces polycyclic (e.g. bicyclic) ring systems wherein one or more rings are non-aromatic, provided that at least one ring is aromatic. In such polycyclic systems, the group may be attached by the aromatic ring, or by a non-aromatic ring. In general, such groups may be monocyclic or bicyclic and may contain, for example, 6 to 12 ring members, more usually 6 to 10 ring members. Examples of monocyclic groups are groups containing 6 ring members. Examples of bicyclic groups are those containing 10 and 12 ring members.

Examples of aryl groups include phenyl, naphthyl, indenyl, and tetrahydronaphthyl groups.

References to "heterocyclyl" groups as used herein shall, unless the context indicates otherwise, include both aromatic and non-aromatic ring systems. Thus, for example, the term "heterocyclyl groups" includes within its scope aromatic, non-aromatic, unsaturated, partially saturated and fully saturated heterocyclyl ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Where reference is made herein to heterocyclyl groups, heterocyclyl ring can, unless the context indicates otherwise, be unsubstituted or substituted by one or more substituents for example molecular fragments, molecular scaffolds or functional groups as discussed herein. It will be appreciated that references to "heterocyclyl" groups include reference to heterocyclyl groups which may be optionally substituted by one or more (e.g. 1, 2 or 3) groups as indicated above.

The heterocyclyl groups can be a heteroaryl groups having from 5 to 12 ring members, more usually from 5 to 10 ring members and in particular 5 to 6 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

The term "non-aromatic group" embraces unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine. Partially saturated heterocyclyl groups include pyrazolines, for example 2-pyrazoline and 3-pyrazoline.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzothiene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of non-aromatic heterocyclyl groups are groups having from 3 to 12 ring members, more usually 5 to 10 ring members and in particular 5 to 6 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocyclic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as oxa- and aza analogues of bicycloalkanes and tricycloalkanes (e.g. oxa-adamantane). For an explanation of the distinction between fused and bridged ring systems, see *Advanced Organic Chemistry*, by Jerry March, 4th Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

In one embodiment $R^2$ represents a 5 or 6-membered heterocyclyl substituted by one halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^g$, —$(CH_2)_n$—O—$C_{1-6}$ alkyl, —O—$(CH_2)_n$—$OR^g$, halo$C_{1-6}$ alkyl, halo$C_{1-6}$ alkoxy, $C_{1-6}$ alkanol, =O, =S, nitro, Si$(R^g)_4$, —$(CH_2)$—CN, —S—$R^g$, —SO—$R^g$, —$SO_2$—$R^g$, —$COR^g$, —$(CR^gR^h)$—$COOR^k$, —$(CH_2)_s$—$CONR^gR^h$, —$(CH_2)_s$—$NR^gR^h$, —$(CH_2)_s NR^g COR^h$, —$(CH_2)_s$—$NR^g SO_2$—$R^h$, —$(CH_2)$—NH—$SO_2$—$NR^gR^h$, —$OCONR^gR^h$, —$(CH_2)_s$—$NR^g CO_2R^h$, —O—$(CH_2)_s$—$CR^gR^h$—$(CH_2)_t$—$OR^k$ or —$(CH_2)_s$—$SO_2NR^gR^h$ groups.

In one embodiment $R^2$ represents —C(=O)—$R^x$, —O—$R^x$ or a heterocyclyl selected from thiadiazolyl, oxadiazolyl, imidazoyl, piperidinyl, pyridinyl and pyrimidinyl wherein the heterocyclyl is optionally substituted by one or more, for example one or two, of halogen, $C_{1-6}$alkyl, halo$C_{1-6}$ alkyl, —$(CH_2)_s$—$NR^gR^h$, $C_{1-6}$alkanol or —$(CR^gR^h)COOR^k$, wherein $R^x$ is $C_{3-6}$cycloalkyl or $R^x$ is $C_{1-6}$alkyl substituted with hydroxyl, and $R^g$, $R^h$ and $R^k$ are independently selected from hydrogen or $C_{1-6}$alkyl.

In one embodiment $R^2$ represents —C(=O)—$R^x$, —O—$R^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of —$CH_3$, —$C(CH_3)_2$, —F, —$CF_3$, —$NH_2$, —$N(CH_3)_2$, —$C_{4-6}$alkanol or —$(CR^gR^h)COOR^k$. In one embodiment $R^g$, $R^h$ and $R^k$ are independently selected from hydrogen or $C_{1-6}$alkyl.

In one embodiment $R^2$ represents a heterocyclyl selected from thiadiazolyl, oxadiazolyl, imidazoyl, piperidinyl, pyridinyl and pyrimidinyl wherein the heterocyclyl is optionally substituted by one or more, for example one or two, of halogen, $C_{1-6}$alkyl, halo$C_{1-6}$ alkyl, —$(CH_2)_s$—$NR^gR^h$, $C_{1-6}$alkanol or —$(CR^gR^h)COOR^k$, e.g. —$CH_3$, —$C(CH_3)_2$, —F, —$CF_3$, —$NH_2$, —$N(CH_3)_2$, —$C_4$alkanol or —$C(CH_3)_2COOCH_2CH_3$.

In one embodiment $R^g$, $R^h$ and $R^k$ are independently selected from hydrogen or $C_{1-6}$alkyl e.g. hydrogen, —$CH_3$ or —$CH_2CH_3$.

In one embodiment $R^2$ represents —C(=O)—$R^x$, —O—$R^x$, or a 5 or 6 membered heterocyclyl selected from thiadiazolyl, oxadiazolyl, pyridinyl or pyrimidinyl wherein each heterocyclyl is optionally substituted by one or more, for example one or two, of —$CH_3$, —F, —$CF_3$ or —$NH_2$.

In one embodiment $R^2$ represents a 5 or 6 membered heterocyclyl selected from thiadiazolyl, oxadiazolyl, pyridinyl or pyrimidinyl wherein each heterocyclyl is substituted by one or more, for example one, of —$CH_3$, —F, —$CF_3$ or —$NH_2$.

In one embodiment $R^2$ represents —C(=O)—$R^x$ or —O—$R^x$, wherein $R^x$ is $C_{3-6}$cycloalkyl or $R^x$ is $C_{1-6}$alkyl substituted with hydroxyl, or $R^2$ represents a 5 or 6 membered heterocyclyl selected from thiadiazolyl, oxadiazolyl, pyridinyl or pyrimidinyl wherein each heterocyclyl is optionally substituted by one or more, for example one or two, of —$CH_3$, —F, —$CF_3$ or —$NH_2$.

In one embodiment $R^2$ represents thiadiazolyl, oxadiazolyl or pyrimidinyl. In one embodiment the thiadiazolyl, oxadiazolyl or pyrimidinyl is optionally substituted by one or more, for example one or two, of —$CH_3$, —F, $CF_3$ or —$NH_2$. In one embodiment the thiadiazolyl, oxadiazolyl or pyrimidinyl is substituted by one or more, for example one, of —$CH_3$, —F, $CF_3$ or —$NH_2$.

In one embodiment $R^2$ represents thiadiazolyl or oxadiazolyl. In one embodiment the thiadiazolyl or oxadiazolyl is optionally substituted by one or more, for example one or two, of —$CH_3$, —F, —$CF_3$ or —$NH_2$. In one embodiment the thiadiazolyl or oxadiazolyl is substituted by one or more, for example one, of —$CH_3$, —F, —$CF_3$ or —$NH_2$.

In a further embodiment $R^2$ represents oxadiazolyl optionally substituted by one or more, for example one or two, of —$CH_3$, —F, —$CF_3$ or —$NH_2$. In a further embodiment $R^2$ represents oxadiazolyl substituted by one or more, for example one, of —$CH_3$, —F, —$CF_3$ or —$NH_2$ In a still further embodiment $R^2$ represents thiadiazolyl optionally substituted by one or more, for example one or two, of $C_{1-6}$ alkyl. In a still further embodiment $R^2$ represents thiadiazolyl substituted by one or more, for example one, of $C_{1-6}$ alkyl.

In one embodiment $R^2$ represents unsubstituted thiadiazolyl, unsubstituted oxadiazolyl, substituted thiadiazolyl or substituted oxadiazolyl wherein the substituent is $C_{1-2}$ alkyl. In a further embodiment $C_{1-2}$ alkyl is —$CH_3$.

In one embodiment $R^2$ represents unsubstituted thiadiazolyl or unsubstituted oxadiazolyl. In one embodiment the thiadiazolyl or oxadiazolyl is substituted by one $C_{1-2}$ alkyl. In a further embodiment $C_{1-2}$ alkyl is —$CH_3$.

In one embodiment $R^2$ represents —C(=O)—$R^x$ or —O—$R^x$.

In one embodiment $R^2$ represents —C(=O)—$R^x$ or —O—$R^x$ wherein $R^x$ represents $C_{3-6}$cycloalkyl or $R^x$ represents $C_{1-6}$alkyl optionally substituted with hydroxyl or NR'R".

In one embodiment $R^2$ represents —C(=O)—$R^x$ or —O—$R^x$ wherein $R^x$ is $C_{3-6}$cycloalkyl or $R^x$ is $C_{1-6}$alkyl substituted with hydroxyl, or a NR'R" wherein R' and R" taken together with the nitrogen to which they are attached form a saturated heterocyclyl selected from piperidinyl, piperazinyl, morpholinyl or thiomorpholinyl.

In one embodiment $R^2$ represents —C(=O)—$R^x$ wherein $R^x$ is $C_{3-6}$cycloalkyl. In a further embodiment $C_{3-6}$cycloalkyl is cyclopropyl.

In one embodiment $R^2$ represents —O—$R^x$ wherein $R^x$ is $C_{1-6}$alkyl substituted with hydroxyl. In a further embodiment $R^x$ is $C_{2-3}$alkyl substituted with hydroxyl.

In one embodiment $R^x$ is $C_{3-6}$cycloalkyl or $R^x$ is $C_{1-6}$alkyl substituted with hydroxyl.

In one embodiment $R^2$ is pyrimidinyl (e.g. pyrimidin-2-yl or pyrimidin-3-yl or pyrimidin-4-yl) optionally substituted by one or more, for example one or two, of halogen, $C_{1-6}$ alkyl, halo$C_{1-6}$ alkyl, or —$(CH_2)_s$—$NR^gR^h$ groups, for example —$CH_3$, —F, —$CF_3$, —$N(CH_3)_2$ or —$NH_2$. In one embodiment $R^2$ is pyrimidinyl (e.g. pyrimidin-2-yl or pyrimidin-3-yl or pyrimidin-4-yl) substituted by one or more, for example one, of halogen, $C_{1-6}$ alkyl, halo$C_{1-6}$ alkyl, or —$(CH_2)_s$—$NR^gR^h$ groups, for example —$CH_3$, —F, —$CF_3$, —$N(CH_3)_2$ or —$NH_2$.

In one embodiment $R^2$ is a pyrimidinyl optionally substituted by one or more, for example one or two, of —$CH_3$, —F, —$CF_3$ or —$NH_2$. In one embodiment $R^2$ is a pyrimidinyl substituted by one or more, for example one, of —$CH_3$, —F, —$CF_3$ or —$NH_2$ In one embodiment $R^2$ is pyrimidin-2-yl unsubstituted or substituted by one or two of —F or —$NH_2$.

In one embodiment $R^2$ is pyrimidinyl (e.g. pyrimidin-2-yl or pyrimidin-3-yl or pyrimidin-4-yl) optionally substituted by one or more, for example one or two, of —$(CH_2)$—$NR^gR^h$, e.g. —$NH_2$ or —$N(CH_3)_2$. In one embodiment $R^2$ is pyrimidinyl (e.g. pyrimidin-2-yl or pyrimidin-3-yl or pyrimidin-4-yl) substituted by one or more, for example one, of —$(CH_2)_s$—$NR^gR^h$, e.g. —$NH_2$ or —$N(CH_3)_2$.

In one embodiment $R^2$ is pyrimidin-3-yl optionally substituted by one or more, for example one —$(CH_2)_s$—$NR^gR^h$, where s is zero and $R^g$ and $R^h$ are $C_{1-6}$ alkyl. In one embodiment $R^g$ and $R^h$ are —$CH_3$.

In one embodiment $R^2$ is pyrimidin-4-yl substituted by one or two of —$CH_3$, —$CF_3$ or —$NH_2$.

In one embodiment $R^2$ represents pyrimidinyl for example pyrimidin-2-yl or pyrimidin-3-yl. In one embodiment the pyrimidinyl (e.g. pyrimidin-2-yl) is optionally substituted by one or more, for example one or two, of $C_{1-6}$alkyl, $C_{1-6}$alkanol or —$(CR^gR^h)COOR^k$. In one embodiment the pyrimidinyl (e.g. pyrimidin-2-yl) is substituted by one or more, for example one, of $C_{1-6}$alkyl, $C_{1-6}$alkanol or —$(CR^gR^h)COOR^k$.

In one embodiment $R^2$ represents pyrimidinyl. In one embodiment the pyrimidinyl is optionally substituted by one or more, for example one or two, of —$CH(CH_3)_2$, —$C(CH_3)_2OH$, —$C(CH_3)_2CH_2OH$, —$C(CH_3)_2COOH$ or —$C(CH_3)_2COOCH_2CH_3$. In one embodiment the pyrimidinyl is substituted by one or more, for example one, of —$CH(CH_3)_2$, —$C(CH_3)_2OH$, or —$C(CH_3)_2COOCH_2CH_3$.

In one embodiment $R^2$ represents pyrimidinyl. In one embodiment the pyrimidinyl is substituted by one or more, for example one or two, of —$CH(CH_3)_2$, —$C(CH_3)_2OH$, —$C(CH_3)_2CH_2OH$, —$C(CH_3)_2COOH$ or —$C(CH_3)_2COOCH_2CH_3$, in particular or more, for example one or two, of —$CH(CH_3)_2$, —$C(CH_3)_2CH_2OH$ or —$C(CH_3)_2COOCH_2CH_3$.

In a further embodiment $R^2$ is pyrimidin-2-yl substituted by one or more, for example one or two, of —$CH(CH_3)_2$, —$C(CH_3)_2OH$, —$C(CH_3)_2CH_2OH$, —$C(CH_3)_2COOH$ or —$C(CH_3)_2COOCH_2CH_3$, in particular one or more, for example one or two, of —$CH(CH_3)_2$, —$C(CH_3)_2CH_2OH$ or —$C(CH_3)_2COOCH_2CH_3$.

In one embodiment $R^2$ is pyridinyl optionally substituted by one or more, for example one or two, of —$CH_3$, —F, —$CF_3$ or —$NH_2$.

In one embodiment $R^2$ is pyridin-2-yl substituted by one or two of —$CH_3$ or —F.

In one embodiment when $R^2$ represents 5 or 6-membered heterocyclyl it is a 5 or 6-membered heterocyclyl other than optionally substituted pyrazolyl.

In one embodiment $R^2$ represents imidazoyl optionally substituted by one or more, for example one or two, of $C_{1-6}$alkyl.

In one embodiment $R^2$ represents imidazoyl substituted by one or more, for example one, of $C_{1-6}$alkyl. In a further embodiment $R^2$ represents imidazoyl substituted by one or more, for example one, of —$CH_3$. In a still further embodiment $R^2$ represents N-linked imidazoyl substituted by one or more, for example one, —$CH_3$.

In one embodiment $R_a$ represents $C_{2-4}$alkoxy, $C_{1-4}$alkoxy$C_{1-4}$alkyl, cyclobutoxy, —NH—$C_{1-4}$alkyl, —$C_{1-4}$alkyl-NH($C_{1-4}$alkyl), or —$C_{1-4}$alkyl-N($C_{1-4}$alkyl)$_2$ e.g. ethyloxy (—O—$CH_2$—$CH_3$), n-propyloxy, (—O—($CH_2$)$_2$—$CH_3$), —$CH_2$—O—$CH_3$, cyclobutoxy, —NH—($CH_2$)$_2$—$CH_3$, —$CH_2$—NH($CH_3$), or —$CH_2$—N($CH_3$)$_2$.

In another embodiment $R_a$ represents $C_{2-4}$alkoxy, $C_{1-4}$alkoxy$C_{1-4}$alkyl, or cyclobutoxy e.g. ethyloxy (—O—$CH_2$—$CH_3$), n-propyloxy (—O—($CH_2$)$_2$—$CH_3$), —$CH_2$—O—$CH_3$, or cyclobutoxy.

In one embodiment $R^a$ represents $C_{2-4}$alkoxy. In a further embodiment the $C_{2-4}$alkoxy is ethyloxy (—O—$CH_2$—$CH_3$), n-propyloxy (—O—($CH_2$)$_2$—$CH_3$) or i-propyloxy (—O—$CH(CH_3)_2$).

In one embodiment $R^a$ represents halo$C_{2-4}$alkoxy. In a further embodiment the halo$C_{2-4}$alkoxy is —O—$CH_2$—$CF_3$.

In one embodiment $R^a$ represents —$C_{1-4}$alkoxy$C_{1-4}$alkyl. In a further embodiment the —$C_{1-4}$alkoxy$C_{1-4}$alkyl is —$CH_2$—O—$CH_3$.

In one embodiment $R^a$ represents —NH—$C_{1-4}$alkyl. In a further embodiment the —NH—$C_{1-4}$alkyl group is —NH—$CH(CH_3)_2$.

In one embodiment $R^a$ represents —$C_{1-4}$alkyl-N($C_{1-4}$alkyl)$_2$. In a further embodiment the —$C_{1-4}$alkyl-N($C_{1-4}$alkyl)$_2$ is —$CH_2$—N($CH_3$)$_2$.

In one embodiment $R^a$ represents —$C_{1-4}$alkyl-S(=O)$_2$—$C_{1-4}$alkyl. In a further embodiment the —$C_{1-4}$alkyl-S(=O)$_2$—$C_{1-4}$ alkyl is —$CH_2$—$SO_2$—$CH_3$.

In one embodiment $R^a$ represents —S(=O)$_2$—$C_{1-4}$alkyl. In a further embodiment the —S(=O)$_2$—$C_{1-4}$alkyl is —$SO_2$—$CH_3$.

In one embodiment $R^a$ represents —$C_{1-4}$alkyl-NH($C_{1-4}$alkyl). In a further embodiment the —$C_{1-4}$alkyl-NH($C_{1-4}$alkyl) is —$CH_2$—NH$CH_3$.

In one embodiment $R_a$ represents $C_{2-4}$alkoxy, halo$C_2$alkoxy, $C_{1-4}$alkoxy$C_{1-4}$alkyl, cyclobutoxy, cyclopropoxy, —N($C_{1-4}$alkyl)$_2$, —$C_{1-4}$alkyl-NH($C_{1-4}$alkyl), —$C_{1-4}$alkyl-N($C_{1-4}$alkyl)$_2$, or —S(=O)$_2$—$C_{1-4}$alkyl.

In one embodiment $R^1$ represents —NHCONR$^4$R$^5$ or —NHCSNR$^4$R$^5$. In a further embodiment $R^4$ represents hydrogen. In a still further embodiment $R^5$ represents $C_{1-6}$ alkanol, halo$C_{1-6}$ alkyl, $C_{3-8}$ cycloalkyl, $C_{1-6}$alkyl substituted with a $C_{3-8}$ cycloalkyl or $C_{1-6}$ alkyl substituted by one or more —($CH_2$)$_s$—CN groups or $C_{1-6}$alkyl optionally substituted by one or more —($CH_2$)$_s$—NR$^g$R$^h$.

In a yet further embodiment the $C_{3-8}$ cycloalkyl is a $C_{3-6}$ cycloalkyl.

In a still further embodiment $R^5$ is $C_{1-6}$ alkyl substituted by —($CH_2$)$_s$—CN, wherein s is 0.

In a yet further embodiment $R^5$ is $C_{1-6}$ alkyl substituted by —($CH_2$)$_s$—NR$^g$R$^h$, wherein s is 0 and R$^g$ and R$^h$ are independently hydrogen or $C_{1-4}$alkyl. In a still further embodiment R$^g$ and R$^h$ are both hydrogen. In a still further embodiment R$^g$ and R$^h$ are both $C_{1-4}$alkyl. In a still further embodiment one of R$^g$ and R$^h$ is $C_{1-4}$alkyl and the other is hydrogen.

In one embodiment $R^1$ represents —NHCONR$^4$R$^5$. In a further embodiment $R^4$ represents hydrogen. In a still further embodiment $R^5$ represents $C_{1-6}$alkyl substituted by one or more R$^p$ groups. In a still further embodiment each R$^p$ group is independently chosen from halogen, for example fluorine, and —OR$^g$. In a yet further embodiment R$^g$ represents hydrogen.

In one embodiment $R^1$ represents —NHCONR$^4$R$^5$. In one embodiment $R^1$ represents —NHCONR$^4$R$^5$ wherein $R^4$ represents hydrogen and $R^5$ represents ethyl or $CH_2CF_3$. In an alternative embodiment. $R^1$ represents —NHCONR$^4$R$^5$ wherein $R^4$ represents hydrogen and $R^5$ cyclopropyl. In an alternative embodiment, $R^1$ represents —NHCONR$^4$R$^5$ wherein $R^4$ and $R^5$ both represent hydrogen.

In one embodiment $R^1$ represents —NH-thiadiazolyl or —NH-oxadiazolyl.

In one embodiment $R^1$ represents —NH-thiadiazolyl or —NH-oxadiazolyl and the thiadiazolyl or oxadiazolyl is substituted by one or more, (for example 1, 2 or 3) $C_{1-6}$ alkyl groups. In a further embodiment each $C_{1-6}$ alkyl is a $C_{1-4}$ alkyl.

In one embodiment if $R^1$ is —NHCONR$^4$R$^5$ wherein $R^4$ and $R^5$ each independently represent hydrogen or $C_{3-8}$cycloalkyl and $R^a$ represents $C_{2-4}$alkoxy, halo$C_{2-4}$alkoxy, $C_{1-4}$alkoxy$C_{1-4}$alkyl, cyclobutloxy, cyclopropoxy, —NH—$C_{1-4}$alkyl, —N($C_{1-4}$alkyl)$_2$, —$C_{1-4}$alkyl-N($C_{1-4}$alkyl)$_2$, than $R^2$ is other than an optionally substituted 5 or 6-membered heterocycle.

In one embodiment if $R^1$ is —NHCONR$^4$R$^5$ wherein $R^4$ represents hydrogen and $R^5$ represents $C_{1-6}$alkyl or halo $C_{1-6}$alkyl and $R^a$ represents $C_{2-4}$alkoxy, halo$C_{2-4}$alkoxy, $C_{1-4}$alkoxy$C_{1-4}$alkyl, cyclobutoxy, cyclopropoxy, —NH—$C_{1-4}$alkyl, —N($C_{1-4}$alkyl)$_2$, —$C_{1-4}$alkyl-NH($C_{1-4}$alkyl), —$C_{1-4}$alkyl-N($C_{1-4}$alkyl)$_2$, then the optionally substituted 5 or 6-membered heterocycle in $R^2$ is other than:

(a) pyridazinyl optionally substituted by one or more (e.g. 1, 2 or 3) R$^{ee}$ groups, or two or more (e.g. 2, 3 or 4) R$^{bb}$ groups;

(b) N-linked imidazolyl optionally substituted on the nitrogen atom or the C-2 or C-5 atoms by one or more (e.g. 1, 2 or 3) R$^{bb}$ groups or at the C-4 atom by one R$^{ee}$ group;

(c) C-linked imidazolyl optionally substituted by one or two R$^{mm}$ groups on either or both of the nitrogen atoms or optionally substituted by one or two R$^{ee}$ groups on one or two carbon atoms;

(d) pyrazinyl optionally substituted by one or more (e.g. 1, 2 or 3) R$^{bb}$ groups;

(e) thiophenyl substituted by one or more (e.g. 1, 2 or 3) R$^{ee}$ groups;

(f) triazinyl optionally substituted by one or two R$^{bb}$ groups;

(g) pyrazolyl substituted by one or more (e.g. 1, 2 or 3) R$^{ff}$ groups;

(h) pyrimidin-2-yl optionally substituted by one or more (e.g. 1, 2 or 3) R$^{bb}$ groups;

(j) pyrimidin-4-yl optionally substituted by one or more (e.g. 1, 2 or 3) R$^{gg}$ groups or two or more (e.g. 2, 3 or 4) R$^{bb}$ groups;

(k) pyrimidin-5-yl optionally substituted by one or more (e.g. 1, 2 or 3) R$^{pp}$ groups or two or more (e.g. 2, 3 or 4) R$^{bb}$ groups;

(m) thiadiazolyl substituted by one R$^{hh}$ group;

(n) pyridin-2-yl optionally substituted by one or more (e.g. 1, 2 or 3) R$^{bb}$ groups;

(o) pyridin-3-yl substituted by one or more (e.g. 1, 2 or 3) R$^{jj}$ groups;

(p) pyridin-4-yl substituted by one or more (e.g. 1, 2 or 3) R$^{kk}$ groups or two or more (e.g. 2, 3 or 4) R$^b$ groups;

(q) oxo-dihydro-pyridin-3-yl substituted by one or more (e.g. 1, 2 or 3) R$^{jj}$ groups;

(r) N-methylpyrazolyl optionally substituted by one or more (e.g. 1, 2 or 3) R$^{qq}$ groups;

(x) N-unsubstituted pyridin-3-yl substituted on one of the carbon atoms with a substituent from the group $R^{bb}$ and substituted on another carbon atom with a substituent from the group $R^{aa}$;

$R^{aa}$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-COOR^{zz}$, $-(CR^{xx}R^{yy})_s-CONR^{ww}R^{zz}$, $-(CH_2)_s-CONR^{xx}R^{yy}$, $-(CH_2)_s-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_x-NR^{xx}CO_2R^{yy}$, $-O-(CH_2)_s-NR^{xx}R^{yy}$, $-O-(CH_2)_x-CR^{xx}R^{yy}-(CH_2)_t-OR^{zz}$ or $-(CH_2)_s-SO_2NR^{xx}R^{yy}$ groups;

$R^{bb}$ represents an $R^{aa}$ group or a —Y-heterocyclyl group wherein said heterocyclyl group may be optionally substituted by one or more (e.g. 1, 2 or 3) $R^{aa}$ groups;

Y represents a bond, $-CO-(CH_2)_s-$, $-(CR^{xx}R^{yy})_sCO-$, $-COO-$, $-(CH_2)_n-(CR^{xx}R^{yy})_s-$, $-NR^{xx}-(CH_2)_s-$, $-(CH_2)_s-NR^{xx}-$, $-CONR^{xx}-$, $-NR^{xx}CO-$, $-SO_2NR^{xx}-$, $-NR^{xx}SO_2-$, $-NR^{xx}CONR^{yy}-$, $-NR^{xx}CSNR^{yy}-O-(CH_2)_s-$, $-(CH_2)_s-O-$, $-S-$, $-SO-$ or $-(CH_2)_s-SO_2-$, $R^{ee}$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-COOR^{zz}$, $-(CR^{xx}R^{yy})_s-CONR^{ww}R^{zz}$, $-(CH_2)_s-CONR^{xx}R^{yy}$, $-(CH_2)_s-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups, or a —Y-heterocyclyl group wherein said heterocyclyl group may be optionally substituted by one or more (e.g. 1, 2 or 3) $R^{aa}$ groups;

$R^f$ represents halogen, $C_{4-6}$ alkyl, $C_{2-6}$ alkenyl, $C_{2-6}$ alkynyl, $C_{3-3}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{2-6}$ alkyl, monohalomethyl, dihalomethyl, halo$C_{1-6}$ alkoxy, $C_{3-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-COOR^{zz}$, $-(CR^{xx}R^{yy})_s-CONR^{ww}R^{zz}$, $-(CH_2)_s-CONR^{xx}R^{yy}$, $-CH_2-NR^{xx}R^{yy}$, $-(CH_2)_{3-4}-NR^{xx}R^{yy}$, $-(CH_2)_s-$NH$C_{1-6}$ alkyl, $-(CH_2)_s-N(C_{1-6}$ alkyl$)_2$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}-(CH_2)_n-SO_2NR^{xx}R^{yy}$ or $-(CH_2)_s-SO_2NHR^{yy}$ groups, or a —Y-heterocyclyl group wherein said heterocyclyl group may be optionally substituted by one or more (e.g. 1, 2 or 3) $R^{aa}$ groups;

$R^{hh}$ represents halogen, $C_{3-6}$ alkyl, $C_{2-6}$ alkenyl, $C_{2-6}$ alkynyl, $C_{4-43}$ cycloalkyl, $C_{3-8}$ cycloalkenyl, $-OR^{xx}$, $-(CH_2)_{2-4}-O-C_{1-6}$ alkyl, $-(CH_2)_n-O-C_{2-6}$ alkyl, $-O-(CH_2)_n-OR^{xx}$, halo$C_{1-6}$ alkyl, halo$C_{1-6}$ alkoxy, $C_{2-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-COOR^{zz}$, $-(CR^{xx}R^{yy})_s-CONR^{ww}R^{zz}$, $-(CH_2)_s-CONR^{xx}R^{yy}$, $-(CH_2)_s-NR^{xx}R^{yy}$, $-(CH_2)_sNR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups, or a —Y-heterocyclyl group wherein said heterocyclyl group may be optionally substituted by one or more (e.g. 1, 2 or 3) $R^{aa}$ groups;

$R^{jj}$ represents chlorine, ethyl, $C_{4-6}$ alkyl, $C_{2-6}$ alkenyl, $C_{2-6}$ alkynyl, $C_{3-8}$ cycloalkyl, $C_{3-8}$ cycloalkenyl, $-O-C_2$ alkyl, $-O-C_{4-6}$ alkyl, $-(CH_2)_n-O-C_{1-6}$ alkyl, $-O-(CH_2)_n-OR^{xx}$, halo$C_{2-6}$ alkyl, monohalomethyl, dihalomethyl, halo$C_{1-6}$ alkoxy, $C_{1-2}$ alkanol, $C_{4-6}$ alkanol, =S, nitro, Si$(R^{xx})_4$, $-(CH_2)_s-$CN, $-S-R^{xx}$, $-SO-R^{xx}$, $-SO_2-R^{xx}$, $-COR^x$, $-(CR^xR^{yy})_s-COOC_{1-6}$ alkyl, $-(CR^xR^{yy})$, $-CONR^{ww}R^{zz}$, $-(CH_2)_s-CONR^{xx}R^{yy}$, $-(CH_2)_s-$NH$C_{1-6}$ alkyl, $-(CH_2)_s-$NMe$(C_{2-6}$ alkyl), $-(CH_2)_s-N(C_{2-6}$ alkyl$)_2$, $-(CH_2)_n-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-O-(CH_2)_n-NR^{xx}R^{yy}$, $-O-(CH_2)_s-CR^{xx}R^{yy}-(CH_2)_t-OR^{zz}$, $-(CH_2)_s-SO_2NR^{xx}R^{yy}$, piperazine substituted by $R^{mm}$, or a piperidinyl, or a —O-piperidinyl group wherein said piperidinyl group is substituted by one or more (e.g. 1, 2 or 3) $R^{aa}$ groups;

$R^{kk}$ represents chlorine, $C_{2-6}$ alkyl, $C_{2-6}$ alkenyl, $C_{2-6}$ alkynyl, $C_{3-8}$ cycloalkyl, $C_{3-8}$ cycloalkenyl, $C_{2-6}$ alkoxy, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-2}$ alkanol. $C_{4-6}$ alkanol, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^xR^{yy})$, $-COOR^{zz}$, $-(CR^xR^{yy})$, $-CONR^{ww}R^{zz}$, $-(CH_2)_s-CONR^{xx}R^{yy}$, $-(CH_2)_s-$NH$C_{1-6}$ alkyl, $-(CH_2)_s-N(C_{1-6}$ alkyl$)_2$, $-(CH_2)_n-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups;

$R^{mm}$ represents halogen, $C_{3-6}$ alkyl, $C_{2-6}$ alkenyl, $C_{2-6}$ alkynyl, $C_{3-8}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-COOR^{zz}$, $-(CR^{xx}R^{yy})_s-CONR^{xx}R^{yy}$, $-(CH_2)_s-CONR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups, or a —Y-heterocyclyl group wherein said heterocyclyl group may be optionally substituted by one or more (e.g. 1, 2 or 3) $R^{aa}$ groups;

$R^{nn}$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-6}$ alkanol, =O, =S, nitro, Si$(R^{xx})_4$, $-(CH_2)_s-$CN, $-S-R^{xx}$, $-SO-R^{xx}$, $-SO_2-R^{xx}$, $-COR^{xx}$, $-(CR^{xx}R^{yy})_s-CONR^{ww}R^{zz}$, $-(CH_2)_s-CONR^{xx}R^{yy}$, $-(CH_2)_s-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}$, $-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups;

$R^{pp}$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^{xx}$, $-(CH_2)_n-O-C_{1-6}$ alkyl, $-O-(CH_2)_n-OR^{xx}$, halo$C_{1-6}$ alkyl, halo$C_{1-6}$ alkoxy, $C_{1-6}$ alkanol, =O, =S, nitro, Si$(R^{xx})_4$, $-(CH_2)_s-$CN, $-S-R^{xx}$, $-SO_2-R^{xx}$, $-COR^{xx}$, $-(CR^{xx}R^{yy})_s-COOR^{zz}$, $-(CR^{xx}R^{yy})_s-CONR^{xx}R^{yy}$, $-(CH_2)_s-CONR^{xx}R^{yy}$, $-(CH_2)_s-NR^{xx}R^{yy}$, $-(CH_2)_s-NR^{xx}COR^{yy}$, $-(CH_2)_s-NR^{xx}SO_2-R^{yy}$, $-(CH_2)_s-NH-SO_2-NR^{xx}R^{yy}$, $-OCONR^{xx}R^{yy}-(CH_2)_s-NR^{xx}CO_2R^{yy}$, $-O-(CH_2)_s-CR^{xx}R^{yy}-(CH_2)_t-OR^{zz}$ or $-(CH_2)_s-SO_2NR^{xx}R^{yy}$ groups; a —Y-(4-membered heterocyclyl group) wherein said 4-membered heterocyclyl group is substituted by one or more (e.g. 1, 2 or 3) $R^{aa}$ groups; or a —Y-(5-10 membered heterocyclyl group) wherein said 5-10 membered heterocyclyl group may be optionally substituted by one or more (e.g. 1, 2 or 3) $R^{aa}$ groups;

$R^{qq}$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, —$OR^{xx}$, —$(CH_2)_n$—O—$C_{1-6}$ alkyl, —O—$(CH_2)_n$—$OR^{xx}$, halo$C_{2-6}$ alkyl, monohalomethyl, dihalomethyl, halo$C_{1-6}$ alkoxy, $C_{2-6}$ alkanol, =O, =S, nitro, Si$(R^{xx})_4$, —$(CH_2)$, —CN, —S—$R^{xx}$, —SO—$R^{xx}$, —$SO_2$—$R^{xx}$, —$COR^{xx}$, —$(CR^{xx}R^{yy})_s$—$COOR^{zz}$, —$(CR^{xx}R^{yy})_s$—$CONR^{ww}R^{zz}$, —$(CH_2)_s$—$CONR^{xx}R^{yy}$, —NH($C_{1-6}$alkyl), —N($C_{1-6}$alkyl)$_2$, —$(CH_2)_n$—$NR^{xx}R^{yy}$, —$(CH_2)_s$—$NR^{xx}COR^{yy}$, —$(CH_2)_s$—$NR^{xx}SO_2$—$R^{yy}$, —$(CH_2)_s$—NH—$SO_2$—$NR^{xx}R^{yy}$, —$OCONR^{xx}R^{yy}$, —$(CH_2)_s$—$NR^{xx}CO_2R^{yy}$, —O—$(CH_2)_s$—$NR^{xx}R^{yy}$, —O—$(CH_2)_s$—$CR^{xx}R^{yy}$—$(CH_2)_t$—$OR^{zz}$ or —$(CH_2)_s$—$SO_2NR^{xx}R^{yy}$ groups, or a —Y-heterocyclyl group wherein said heterocyclyl group may be optionally substituted by one or more (e.g. 1, 2 or 3) $R^{aa}$ groups;

$R^{ww}$, $R^{xx}$, $R^{yy}$ and $R^{zz}$ independently represent hydrogen, $C_{1-6}$ alkyl, $C_{2-6}$ alkenyl, $C_{2-6}$ alkynyl, $C_{1-6}$ alkanol, —$COOC_{1-6}$ alkyl, hydroxy, $C_{1-6}$ alkoxy, halo$C_{1-6}$ alkyl, —$(CH_2)_n$—$OC_{1-6}$ alkyl, —CO—$(CH_2)_n$—$C_{1-6}$ alkoxy, $C_{1-6}$ alkylamino, alkyl-N($C_{1-6}$ alkyl)$_2$, —$C_{1-6}$ alkyl-NH($C_{1-6}$ alkyl), $C_{3-8}$ cycloalkyl or $C_{3-8}$ cycloalkenyl or when attached to a nitrogen atom, $R^{ww}$, $R^{xx}$, $R^{yy}$ and $R^{zz}$ may form a ring;

n and q independently represent an integer from 1-4;

s and t independently represent an integer from 0-4;

In one embodiment if $R^1$ is —$NHCONR^4R^5$ wherein $R^4$ represents hydrogen and $R^5$ represents $C_{1-6}$alkyl or halo $C_{1-6}$alkyl and $R^a$ represents $C_{2-4}$alkyloxy, halo$C_{2-4}$alkyloxy, cyclobutoxy, cyclopropoxy, —NH—$C_{1-4}$alkyl, —N($C_{1-4}$ alkyl)$_2$, —$C_{1-4}$alkyl-NH($C_{1-4}$alkyl), or —$C_{1-4}$alkyl-N($C_{1-4}$ alkyl)$_2$, then the optionally substituted 5 or 6-membered heterocycle in $R^2$ is:

(a) optionally substituted pyridazinyl;
(b) optionally substituted N-linked imidazolyl;
(c) optionally substituted C-linked imidazolyl;
(d) optionally substituted pyrazinyl;
(e) substituted thiophenyl;
(f) optionally substituted triazinyl;
(g) substituted pyrazolyl;
(h) optionally substituted pyrimidin-2-yl;
(j) optionally substituted pyrimidin-4-yl;
(k) optionally substituted pyrimidin-5-yl;
(m) substituted thiadiazolyl;
(n) optionally substituted pyridin-2-yl;
(o) substituted pyridin-3-yl;
(p) substituted pyridin-4-yl;
(q) substituted oxo-dihydro-pyridin-3-yl;
(r) optionally substituted N-methylpyrazolyl;
(x) substituted N-unsubstituted pyridin-3-yl.

Wherein references to "N-linked imidazolyl" refer to an imidazolyl group linked to the carbon atom of the imidazo[1,2-a]pyridin-3-yl ring system by one of the nitrogen atoms of the imidazolyl group and references to "C-linked imidazolyl" refer to an imidazolyl group linked to the carbon atom of the imidazo[1,2-a]pyridin-3-yl ring system by one of the carbon atoms of the imidazolyl group. Examples of N-linked imidazolyl groups include imidazol-1-yl.

In one embodiment if $R^1$ is —$NHCONR^4R^5$ wherein $R^4$ represents hydrogen and $R^5$ represents $C_{1-6}$alkyl or halo $C_{1-6}$alkyl and $R^a$ represents $C_{2-4}$alkoxy, halo$C_{2-4}$alkoxy, $C_{1-4}$alkoxy$C_{1-4}$alkyl, cyclobutoxy, cyclopropoxy, —N($C_{1-4}$alkyl)$_2$, —$C_{1-4}$alkyl-NH($C_{1-4}$alkyl), or —$C_{1-4}$alkyl-N($C_{1-4}$alkyl)$_2$, then $R^2$ represents —C(=O)—$R^x$, —O—$R^x$, or thiadiazolyl or oxadiazolyl optionally substituted by one or more, for example one or two, of —$CH_3$, —F, —$CF_3$ or —$NH_2$.

In one embodiment $R^1$ represents —$NHCONH_2$, —$NHCONHCH_2CF_3$, —$NHCONHCH(OH)CF_3$, —$NHCONHCH_2CH_3$ or $NHCONHCH_2CH(CH_3)_2$. In another embodiment $R^1$ represents —$NHCONHCH_2CF_3$, —$NHCONHCH_2CH_3$ or $NHCONHCH_2CH(CH_3)_2$.

in one embodiment if $R^1$ is —$NHCONR^4R^5$ wherein $R^4$ represents hydrogen and $R^5$ represents halo$C_{1-6}$alkyl and $R^a$ represents $C_{2-4}$alkoxy, halo$C_{2-4}$alkoxy, $C_{1-4}$alkoxy$C_{1-4}$alkyl, cyclobutoxy, cyclopropoxy, —N($C_{1-4}$alkyl)$_2$, —$C_{1-4}$alkyl-NH($C_{1-4}$alkyl), or —$C_{1-4}$alkyl-N($C_{1-4}$alkyl)$_2$, then the optionally substituted 6-membered heterocycle in $R^2$ is other than unsubstituted pyridine-3-yl or unsubstituted pyridine-4-yl.

In one embodiment $R^1$ represents $NHCONR^4R^5$ and $R^4$ represents hydrogen and $R^5$ represents halo$C_{1-6}$alkyl, for example —$CH_2CF_3$. In a further embodiment $R^a$ represents $C_{2-4}$alkoxy, for example i-propyloxy. In a still further embodiment $R^2$ represents pyrimidinyl, thiadiazolyl or oxadiazolyl, each of said rings being optionally substituted. In a still further embodiments the pyrimidinyl, thiadiazolyl or oxadiazolyl is substituted by one or more, for example one or two, of —$CH_3$, —F, —$CF_3$ and —$NH_2$. In a still further embodiments $R^2$ represents thiadiazolyl or oxadiazolyl optionally substituted by one or more, for example one or two, of —$CH_3$, —F, —$CF_3$ and —$NH_2$.

In one embodiment $R^1$ represents $NHCONR^4R^5$ and $R^4$ represents hydrogen and $R^5$ represents $C_{1-6}$alkyl substituted by one or more groups selected from fluorine and hydroxyl, for example $R^5$ may represent —$CHOHCF_3$. In a further embodiment $R^a$ represents $C_{2-4}$alkoxy, for example i-propyloxy. In a still further embodiment $R^2$ represents pyrimidinyl, thiadiazolyl or oxadiazolyl, each of said rings being optionally substituted. In a still further embodiments the pyrimidinyl, thiadiazolyl or oxadiazolyl is substituted by one or more, for example one or two, of —$CH_3$, —F, —$CF_3$ and —$NH_2$. In a still further embodiments $R^2$ represents oxadiazolyl optionally substituted by one or more, for example one or two, of —$CH_3$, —F, —$CF_3$ and —$NH_2$. In a still further embodiments $R^2$ represents oxadiazolyl optionally substituted by one of —$CH_3$, —F, —$CF_3$ and —$NH_2$.

In one embodiment $R^1$ represents $NHCONR^4R^5$ and $R^4$ represents hydrogen and $R^5$ represents halo$C_{1-6}$alkyl, for example —$CH_2CF_3$. In a further embodiment $R^a$ represents $C_{2-4}$alkoxy, for example i-propyloxy. In a still further embodiment $R^2$ represents pyrimidinyl, said pyrimidinyl being optionally substituted. In a still further embodiments the pyrimidinyl is substituted by one or more, for example one, of —N($CH_3$)$_2$, —CH($CH_3$)$_2$, —C($CH_3$)$_2$OH, —C($CH_3$)$_2$CH$_2$OH, —C($CH_3$)$_2$COOH or —C($CH_3$)$_2$COOCH$_2$CH$_3$. In a still further embodiments the pyrimidinyl is substituted by one or more, for example one, of —N($CH_3$)$_2$, —CH($CH_3$)$_2$, —C($CH_3$)$_2$CH$_2$OH, or —C($CH_3$)$_2$COOCH$_2$CH$_3$.

In one embodiment $R^1$ represents $NHCONR^4R^5$ and $R^4$ represents hydrogen and $R^5$ represents halo$C_{1-6}$alkyl, for example —$CH_2CF_3$. In a further embodiment $R^a$ represents $C_{2-4}$alkoxy, for example i-propyloxy. In a still further embodiment $R^2$ represents imidazoyl, said imidazoyl being optionally substituted. In a still further embodiments the imidazoyl is substituted by one or more, for example one, of —$CH_3$. In a still further embodiment $R^2$ represents N-linked imidazoyl substituted by one or more, for example one, of —$CH_3$.

In one embodiment $R^1$ represents $NHCONR^4R^5$ and $R^4$ represents hydrogen and $R^5$ represents $haloC_{1-6}alkyl$, for example $-CH_2CF_3$. In a further embodiment $R^a$ represents $C_{1-4}alkoxyC_{1-4}alkyl$, for example $-CH_2-O-CH_3$. In a still further embodiment $R^2$ represents pyrimidinyl, thiadiazolyl or oxadiazolyl, each of said rings being optionally substituted. In a still further embodiment the pyrimidinyl, thiadiazolyl or oxadiazolyl is substituted by one or more, for example one or two, of $-CH_3$, $-F$, $-CF_3$ and $-NH_2$. In a still further embodiments $R^2$ represents thiadiazolyl or oxadiazolyl optionally substituted by one or more, for example one or two, of $-CH_3$, $-F$, $-CF_3$ and $-NH_2$.

In one embodiment $R^1$ represents $NHCONR^4R^5$ and $R^4$ represents hydrogen and $R^5$ represents $haloC_{1-6}alkyl$, for example $-CH_2CF_3$. In a further embodiment $R^a$ represents cyclobutoxy. In a still further embodiment $R^2$ represents pyrimidinyl, thiadiazolyl or oxadiazolyl, each of said rings being optionally substituted. In a still further embodiment the pyrimidinyl, thiadiazolyl or oxadiazolyl is substituted by one or more, for example one or two, of $-CH_3$, $-F$, $-CF_3$ and $-NH_2$. In a still further embodiments $R^2$ represents thiadiazolyl or oxadiazolyl optionally substituted by one or more, for example one or two, of $-CH_3$, $-F$, $-CF_3$ and $-NH_2$.

In one embodiment, $R^1$ represents $NHCONR^4R^5$ wherein $R^4$ represents hydrogen and $R^5$ represents $haloC_{1-6}alkyl$. $R^a$ represents $C_{2-4}alkoxy$ and $R^2$ represents pyrimidinyl, pyridinyl, thiadiazolyl or oxadiazolyl, each of said rings being optionally substituted.

In one embodiment $R^1$ represents $NHCONR^4R^5$ and $R^4$ represents hydrogen and $R^5$ represents $C_{1-6}alkyl$, for example $-CH_2CH_3$. In a further embodiment $R^a$ represents $C_{2-4}alkoxy$, for example i-propyloxy. In a still further embodiment $R^2$ represents pyrimidinyl, thiadiazolyl or oxadiazolyl, each of said rings being optionally substituted. In a still further embodiments $R^2$ represents thiadiazolyl or oxadiazolyl optionally substituted by one or more, for example one or two, of $-CH_3$, $-F$, $-CF_3$ and $-NH_2$.

In one embodiment $R^1$ represents $NHCONR^4R^5$ and $R^4$ represents hydrogen and $R^5$ represents $C_{1-6}alkyl$, for example $-CH_2-CH(CH_3)_2$. In a further embodiment $R^a$ represents $C_2alkoxy$, for example i-propyloxy. In a still further embodiment $R^2$ represents a heterocyclyl selected from pyrimidinyl, thiadiazolyl or oxadiazolyl, each of said rings being optionally substituted. In a still further embodiment the pyrimidinyl, thiadiazolyl or oxadiazolyl groups are substituted by one or more, for example one or two, of $-CH_3$, $-F$, $-CF_3$ and $-NH_2$. In a still further embodiments $R^2$ represents heterocyclyl selected from thiadiazolyl or oxadiazolyl optionally substituted by one or more, for example one or two, of $-CH_3$, $-F$, $-CF_3$ and $-NH_2$.

In one embodiment $R^1$ represents $NHCONR^4R^5$ and $R^4$ and $R^5$ each represent hydrogen. In a further embodiment $R^a$ represents $C_{2-4}alkoxy$, for example i-propyloxy. In a still further embodiment $R^2$ represents oxadiazolyl, said oxadiazoyl being optionally substituted. In a still further embodiments the oxadiazolyl is substituted by one or more, for example one, of $-CH_3$.

In one embodiment:
$R^1$ is $-NHCONR^4R^5$ wherein $R^4$ represents hydrogen and $R^5$ represents $C_{1-6}alkyl$ or $haloC_{1-6}alkyl$;
$R^a$ represents $C_{2-4}alkoxy$, $C_{1-4}alkoxyC_{1-4}alkyl$ or cyclobutoxy; and
$R^2$ represents $-C(=O)-R^x$, $-O-R^x$, or a heterocyclyl selected from thiadiazolyl, oxadiazolyl, pyridinyl and pyrimidinyl wherein the heterocyclyl is optionally substituted by one or more, for example one or two, of $-CH_3$, $-F$, $-CF_3$ or $-NH_2$.

In one embodiment:
$R^1$ is $-NHCONR^4R^5$ wherein $R^4$ represents hydrogen and $R^5$ represents $C_{1-6}alkyl$ optionally substituted by one or more $R^p$ groups;
$R^a$ represents $C_{2-4}alkoxy$, $C_{1-4}alkoxyC_{1-4}alkyl$ or cyclobutoxy; and
$R^2$ represents $-C(=O)-R^x$, $-O-R^x$, or a heterocyclyl selected from thiadiazolyl, oxadiazolyl, imidazoyl, pyridinyl and pyrimidinyl wherein the heterocyclyl is optionally substituted by one or more, for example one or two, of $-CH_3$, $-F$, $-CF_3$ or $-NH_2$.

In one embodiment:
$R^1$ is $-NHCONR^4R^5$ wherein $R^4$ represents hydrogen and $R^5$ represents $C_{1-6}alkyl$ or $haloC_{1-6}alkyl$;
$R^a$ represents $C_{2-4}alkoxy$, $C_{1-4}alkoxyC_{1-4}alkyl$ or cyclobutoxy; and
$R^2$ represents $-C(=O)-R^x$, $-O-R^x$, or a heterocyclyl selected from thiadiazolyl, oxadiazolyl, imidazoyl, pyridinyl and pyrimidinyl wherein the heterocyclyl is optionally substituted by one or more, for example one or two, of $-CH_3$, $-F$, $-CF_3$ or $-NH_2$.

In one embodiment:
$R^1$ is $-NHCONR^4R^5$ wherein $R^4$ represents hydrogen and $R^5$ represents hydrogen, $C_{1-6}alkyl$ or $haloC_{1-6}alkyl$;
$R^a$ represents $C_{2-4}alkoxy$, $C_{1-4}alkoxyC_{1-4}alkyl$ or cyclobutoxy; and
$R^2$ represents $-C(=O)-R^x$, $-O-R^x$, or a heterocyclyl selected from thiadiazolyl, oxadiazolyl, pyridinyl and pyrimidinyl wherein the heterocyclyl is optionally substituted by one or more, for example one or two, of $-CH_3$, $-F$, $-CF_3$ or $-NH_2$.

In one embodiment:
$R^1$ is $-NHCONR^4R^5$ wherein $R^4$ represents hydrogen and $R^5$ represents $C_{1-6}alkyl$ or $haloC_{1-6}alkyl$;
$R^a$ represents $C_{2-4}alkoxy$, $C_{1-4}alkoxyC_{1-4}alkyl$, cyclobutoxy, $-NH-C_{1-4}alkyl$, $-C_{1-4}alkyl-N(C_{1-4}alkyl)_2$ or $-C_{1-4}alkyl-NH(C_{1-4}alkyl)$; and
$R^2$ represents $-C(=O)-R^x$, $-O-R^x$, or a heterocyclyl selected from thiadiazolyl, oxadiazolyl, pyridinyl and pyrimidinyl wherein the heterocyclyl is optionally substituted by one or more, for example one or two, of $-CH_3$, $-F$, $-CF_3$ or $-NH_2$.

In one embodiment:
$R^1$ is $-NHCONR^4R^5$ wherein $R^4$ represents hydrogen and $R^5$ represents $C_{1-6}alkyl$ or $haloC_{1-6}alkyl$;
$R^a$ represents $C_{2-4}alkoxy$, $C_{1-4}alkoxyC_{1-4}alkyl$, cyclobutoxy; and
$R^2$ represents $-C(=O)-R^x$, $-O-R^x$, or a heterocyclyl selected from thiadiazolyl, oxadiazolyl, pyridinyl and pyrimidinyl wherein the heterocyclyl is optionally substituted by one or more, for example one or two, of halogen, $C_{1-6}alkyl$, $haloC_{1-6}alkyl$, $-(CH_2)_s-NR^gR^h$, $C_{1-6}alkanol$ or $-(CR^gR^h)COOR^k$, e.g. $-CH_3$, $-C(CH_3)_2$, $-F$, $-CF_3$, $-NH_2$, $-N(CH_3)_2$, $-C_4alkanol$ or $-C(CH_3)_2COOCH_2CH_3$.

In one embodiment:
$R^1$ is $-NHCONR^4R^5$ wherein $R^4$ represents hydrogen and $R^5$ represents hydrogen. $C_{1-6}alkyl$ or $haloC_{1-6}alkyl$;
$R^a$ represents $C_{2-4}alkoxy$, $C_{1-4}alkoxyC_{1-4}alkyl$, cyclobutoxy, $-NH-C_{1-4}alkyl$, $-C_{1-4}alkyl-N(C_{1-4}alkyl)_2$ or $-C_{1-4}alkyl-NH(C_{1-4}alkyl)$; and
$R^2$ represents $-C(=O)-R^x$, $-O-R^x$, or a heterocyclyl selected from thiadiazolyl, oxadiazolyl, imidazoyl, pyridinyl and pyrimidinyl wherein the heterocyclyl is optionally substituted by one or more, for example one or two, of halogen, $C_{1-6}alkyl$, $haloC_{1-6}alkyl$, $-(CH_2)_s-NR^gR^h$, $C_{1-6}alkanol$ or —(CR$^g$R$^h$)COOR$^k$, e.g. —CH$_3$, —C(CH$_3$)$_2$, —F, —CF$_3$, —NH$_2$, —N(CH$_3$)$_2$, —C$_4$alkanol or —C(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, C$_{1-6}$alkyl optionally substituted with one or more R$^p$ group, or haloC$_{1-6}$alkyl;
R$^a$ represents C$_{2-4}$alkoxy, C$_{1-4}$alkoxyC$_{1-4}$alkyl, cyclobutoxy, —C$_{1-4}$alkyl-N(C$_{1-4}$alkyl)$_2$ or —C$_{1-4}$alkyl-NH(C$_{1-4}$alkyl); and
R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of halogen, C$_{1-6}$alkyl, haloC$_{1-6}$ alkyl, —(CH$_2$)$_s$—NR$^g$R$^h$, C$_{1-6}$alkanol or —(CR$^g$R$^h$)COOR$^k$, e.g. —CH$_3$, —C(CH$_3$)$_2$, —F, —CF$_3$, —NH$_2$, —N(CH$_3$)$_2$, —C$_4$alkanol or —C(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, C$_{1-6}$alkyl optionally substituted with one or more R$^p$ group;
R$^a$ represents C$_{2-4}$alkoxy, C$_{1-4}$alkoxyC$_{1-4}$alkyl, cyclobutoxy, —NH—C$_{1-4}$alkyl, —C$_{1-4}$alkyl-N(C$_{1-4}$alkyl)$_2$ or —C$_{1-4}$alkyl-NH(C$_{1-4}$alkyl); and
R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of halogen, C$_{1-6}$alkyl, haloC$_{1-6}$ alkyl, —(CH$_2$)$_s$—NR$^g$R$^h$, C$_{1-6}$alkanol or —(CR$^g$R$^h$)COOR$^k$;
R$^p$ represents halogen and —OR$^g$;
R$^g$ represents hydrogen;
R$^x$ is C$_{3-6}$cycloalkyl or R$^x$ is C$_{1-6}$alkyl substituted with hydroxyl, and
R$^g$, R$^h$ and R$^k$ are independently selected from hydrogen or C$_{1-6}$alkyl.

In one embodiment:
R$^1$ is —NHCONR$^4$R$^5$ wherein R$^4$ represents hydrogen and R$^5$ represents hydrogen, C$_{1-6}$alkyl optionally substituted with one or more R$^p$ group;
R$^a$ represents C$_{2-4}$alkoxy, C$_{1-4}$alkoxyC$_{1-4}$alkyl, cyclobutoxy, —NH—C$_{1-4}$alkyl, —C$_{1-4}$alkyl-N(C$_{1-4}$alkyl)$_2$ or —C$_{1-4}$alkyl-NH(C$_{1-4}$alkyl); and
R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of —CH$_3$, —F, —CF$_3$, —NH$_2$, —N(CH$_3$)$_2$, C$_{1-6}$alkyl, C$_{1-6}$alkanol or —(CR$^g$R$^h$)COOR$^k$;
R$^p$ represents halogen and —OR$^g$;
R$^g$ represents hydrogen;
R$^x$ is C$_{3-6}$cycloalkyl or R$^x$ is C$_{1-6}$alkyl substituted with hydroxyl, and
R$^g$, R$^h$ and R$^k$ are independently selected from hydrogen or C$_{1-6}$alkyl.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents —C(=O)—R$^x$, —O—R$^x$, or a heterocyclyl selected from thiadiazolyl, oxadiazolyl, pyridinyl or pyrimidinyl wherein the heterocyclyl is optionally substituted by one or more, for example one or two, of —CH$_3$, —F, —CF$_3$ or —NH$_2$.

In one embodiment:
R$^1$ is —NHCONR$^4$R$^5$ wherein R$^4$ represents hydrogen and R$^5$ represents —CHOHCF$_3$;
R$^a$ represents C$_{2-4}$alkoxy, C$_{1-4}$alkoxyC$_{1-4}$alkyl or cyclobutoxy; and
R$^2$ represents —C(=O)—R$^x$, —O—R$^x$, or a heterocyclyl selected from thiadiazolyl, oxadiazolyl, imidazoyl, pyridinyl and pyrimidinyl wherein the heterocyclyl is optionally substituted by one or more, for example one or two, of —CH$_3$, —F, —CF$_3$ or —NH$_2$.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents —C(=O)—R$^x$, —O—R$^x$, or a heterocyclyl selected from thiadiazolyl, oxadiazolyl, imidazoyl, pyridinyl or pyrimidinyl wherein the heterocyclyl is optionally substituted by one or more, for example one or two, of —CH$_3$, —F, —CF$_3$ or —NH$_2$.

In one embodiment:
R$^1$ is —NHCONR$^4$R$^5$ wherein R$^4$ represents hydrogen and R$^5$ represents hydrogen, —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents —C(=O)—R$^x$, —O—R$^x$, or a heterocyclyl selected from thiadiazolyl, oxadiazolyl, pyridinyl or pyrimidinyl wherein the heterocyclyl is optionally substituted by one or more, for example one or two, of —CH$_3$, —F, —CF$_3$ or —NH$_2$.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy, —C$_{1-2}$alkyl-N(C$_{1-2}$alkyl)$_2$ or —C$_{1-2}$alkyl-NH(C$_{1-2}$alkyl); and
R$^2$ represents —C(=O)—R$^x$, —O—R$^x$, or a heterocyclyl selected from thiadiazolyl, oxadiazolyl, pyridinyl and pyrimidinyl wherein the heterocyclyl is optionally substituted by one or more, for example one or two, of —CH$_3$, —F, —CF$_3$ or —NH$_2$.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents —C(=O)—R$^x$, —O—R$^x$, or a heterocyclyl selected from thiadiazolyl, oxadiazolyl, pyridinyl and pyrimidinyl wherein the heterocyclyl is optionally substituted by one or more, for example one or two, of —CH$_3$, —F, —CF$_3$, —NH$_2$ or —CH(CH$_3$)$_2$, —C(CH$_3$)$_2$OH, —C(CH$_3$)$_2$CH$_2$OH, —C(CH$_3$)$_2$COOH or —C(CH$_3$)$_2$COOCH$_2$CH$_3$.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents —C(=O)—R$^x$, —O—R$^x$, or a heterocyclyl selected from thiadiazolyl, oxadiazolyl, pyridinyl and pyrimidinyl wherein the heterocyclyl is optionally substituted by one or more, for example one or two, of —CH$_3$, —F, —CF$_3$, —NH$_2$ or —CH(CH$_3$)$_2$, —C(CH$_3$)$_2$CH$_2$OH or —C(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy, —NH—C$_{2-4}$alkyl, —C$_{1-2}$alkyl-N(C$_{1-2}$alkyl)$_2$ or —C$_{1-2}$alkyl-NH(C$_{1-2}$alkyl); and
R$^2$ represents —C(=O)—R$^x$, —O—R$^x$, or a heterocyclyl selected from thiadiazolyl, oxadiazolyl, imidazoyl, pyridinyl and pyrimidinyl wherein the heterocyclyl is optionally substituted by one or more, for example one or two, of —CH$_3$, —F, —CF$_3$, —NH$_2$ or —CH(CH$_3$)$_2$, —C(CH$_3$)$_2$OH, —C(CH$_3$)$_2$CH$_2$OH, —C(CH$_3$)$_2$COOH or —C(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy, —NH—C$_{2-4}$alkyl, —C$_{1-2}$alkyl-N(C$_{1-2}$alkyl)$_2$ or —C$_{1-2}$alkyl-NH(C$_{1-2}$alkyl); and
R$^2$ represents —C(=O)—R$^x$, —O—R$^x$, or a heterocyclyl selected from thiadiazolyl, oxadiazolyl, imidazoyl, pyridinyl and pyrimidinyl wherein the heterocyclyl is optionally substituted by one or more, for example one or two, of —CH$_3$, —F, —CF$_3$, —NH$_2$ or —CH(CH$_3$)$_2$, —C(CH$_3$)$_2$CH$_2$OH or —C(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, —CH$_2$CH$_3$, —CH$_2$—CH(CH$_3$)$_2$, —CHOHCF$_3$, or —CH$_2$CF$_3$;
R$^a$ represents C$_{2-3}$alkyloxy, —CH$_2$—O—CH$_3$, or cyclobutoxy, —NH—C$_{2-4}$alkyl, —C$_{1-2}$alkyl-N(C$_{1-2}$alkyl)$_2$ or —C$_{1-2}$alkyl-NH(C$_{1-2}$alkyl); and
R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of —CH$_3$, —F, —CF$_3$, —NH$_2$—N(CH$_3$)$_2$—CH(CH$_3$)$_2$, —C(CH$_3$)$_2$OH, —C(CH$_3$)$_2$CH$_2$OH, —CH(CH$_3$)$_2$COOH or —CH(CH$_3$)$_2$COOCH$_2$CH$_3$.

In one embodiment:
R$^1$ is —NHCONR$^4$R$^5$ wherein R$^4$ represents hydrogen and R$^5$ represents hydrogen, —CH$_2$CH$_3$, —CH$_2$—CH(CH$_3$)$_2$, —CHOHCF$_3$, or —CH$_2$CF$_3$;
R$^a$ represents C$_{2-3}$alkyloxy, —CH$_2$—O—CH$_3$, or cyclobutoxy, —C$_{1-2}$alkyl-N(C$_{1-2}$alkyl)$_2$ or —C$_{1-2}$alkyl-NH(C$_{1-2}$alkyl); and
R$^a$—C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more, for example one or two, of —CH$_3$, —F, —CF$_3$, —NH$_2$—N(CH$_3$)$_2$—CH(CH$_3$)$_2$, —C(CH$_3$)$_2$CH$_2$OH or —CH(CH$_3$)$_2$COOCH$_2$CH$_3$.

In one embodiment:
R$^1$ is —NHCONR$^4$R$^5$ wherein R$^4$ represents hydrogen and R$^5$ represents —CH$_2$CH$_3$, —CH$_2$—CH(CH$_3$)$_2$ or —CH$_2$CF$_3$;
R$^a$ represents C$_{2-3}$alkyloxy, —CH$_2$—O—CH$_3$, or cyclobutoxy; and
R$^2$ represents:
—C(=O)—R$^x$ or —O—R$^x$ wherein R$^x$ is C$_{3-6}$cycloalkyl or C$_{1-6}$alkyl substituted with hydroxyl; or
a heterocyclyl selected from thiadiazolyl, oxadiazolyl, pyridinyl or pyrimidinyl wherein the heterocyclyl is optionally substituted by one or two of —CH$_3$, —F, —CF$_3$ or —NH$_2$.

In one embodiment:
R$^1$ is —NHCONR$^4$R$^5$ wherein R$^4$ represents hydrogen and R$^5$ represents —CH$_2$CF$_3$;
R$^a$ represents C$_3$alkyloxy; and
R$^2$ represents —C(=O)—R$^x$ wherein R$^x$ is C$_{3-6}$cycloalkyl, or a heterocyclyl selected from thiadiazolyl, oxadiazolyl, or pyrimidinyl wherein the heterocyclyl is optionally substituted by methyl.

In one embodiment:
R$^1$ is —NHCONR$^4$R$^5$ wherein R$^4$ represents hydrogen and R$^5$ represents —CH$_2$CF$_3$;
R$^a$ represents propyloxy; and
R$^2$ represents —C(=O)—R$^x$ wherein R$^x$ is cyclopropyl, unsubstituted thiadiazolyl, unsubstituted pyrimidinyl or oxadiazolyl substituted by methyl.

In one embodiment, the compound of formula (I) is a compound selected from Examples F-1 to F-22. In particular, the compound is selected from F-2, F-5, F-6 and F-19, or a pharmaceutically acceptable salt or solvate thereof.

In one embodiment, the compound of formula (I) is a compound selected from Examples F-1 to F-22 or F-23 to F-32. In particular, the compound is selected from F-2, F-5, F-6 and F-19, or a pharmaceutically acceptable salt or solvate thereof.

In one embodiment, the compound of formula (I) is a compound selected from:
1-{3-[7-(4-Amino-5-fluoro-pyrimidin-2-yl)-imidazo[1,2-a]pyridin-3-yl]-5-isopropoxy-phenyl}-3-(2,2,2-trifluoro-ethyl)-urea;
1-[3-Isopropoxy-5-(7-pyrimidin-2-yl-imidazo[1,2-a]pyridin-3-yl)-phenyl]-3-(2,2,2-trifluoro-ethyl)-urea;
1-{3-Isopropoxy-5-[7-(5-methyl-[1,3,4]oxadiazol-2-yl)-imidazo[1,2-a]pyridin-3-yl]-phenyl}-3-(2,2,2-trifluoro-ethyl)-urea;
1-[3-Isopropoxy-5-(7-[1,3,4]thiadiazol-2-yl-imidazo[1,2-a]pyridin-3-yl)-phenyl]-3-(2,2,2-trifluoro-ethyl)-urea;
1-{3-Ethoxy-5-[7-(5-methyl-[1,3,4]oxadiazol-2-yl)-imidazo[1,2-a]pyridin-3-yl]-phenyl}-3-(2,2,2-trifluoro-ethyl)-urea;
1-{3-Methoxymethyl-5-[7-(5-methyl-[1,3,4]oxadiazol-2-yl)-imidazo[1,2-a]pyridin-3-yl]-phenyl}-3-(2,2,2-trifluoro-ethyl)-urea;
1-[3-(7-Cyclopropanecarbonyl-imidazo[1,2-a]pyridin-3-yl)-5-isopropoxy-phenyl]-3-(2,2,2-trifluoro-ethyl)-urea;
1-{3-Isopropoxy-5-[7-(2-trifluoromethyl-pyrimidin-4-yl)-imidazo[1,2-a]pyridin-3-yl]-phenyl}-3-(2,2,2-trifluoro-ethyl)-urea;
1-{3-[7-(4,4-Difluoro-piperidin-1-yl)-imidazo[1,2-a]pyridin-3-yl]-5-isopropoxy-phenyl}-3-(2,2,2-trifluoro-ethyl)-urea;
1-{3-[7-(2-Hydroxy-ethoxy)-imidazo[1,2-a]pyridin-3-yl]-5-isopropoxy-phenyl}-3-(2,2,2-trifluoro-ethyl)-urea;
1-{3-Ethoxy-5-[7-(2-trifluoromethyl-pyrimidin-4-yl)-imidazo[1,2-a]pyridin-3-yl]-phenyl}-3-(2,2,2-trifluoro-ethyl)-urea;
1-{3-Isopropoxy-5-[7-(5-methyl-[1,3,4]thiadiazol-2-yl)-imidazo[1,2-a]pyridin-3-yl]-phenyl}-3-(2,2,2-trifluoro-ethyl)-urea;
1-{3-[7-(3-Hydroxy-propoxy)-imidazo[1,2-a]pyridin-3-yl]-5-isopropoxy-phenyl}-3-(2,2,2-trifluoro-ethyl)-urea;
1-Ethyl-3-[3-isopropoxy-5-(7-[1,3,4]thiadiazol-2-yl-imidazo[1,2-a]pyridin-3-yl)-phenyl]-urea;

1-{3-Cyclobutoxy-5-[7-(5-methyl-[1,3,4]oxadiazol-2-yl)-imidazo[1,2-a]pyridin-3-yl]-phenyl}-3-(2,2,2-trifluoro-ethyl)-urea;
1-{3-Methoxymethyl-5-[7-(2-trifluormethyl-pyrimidin-4-yl)-imidazo[1,2-a]pyridin-3-yl]-phenyl}-3-(2,2,2-trifluoro-ethyl)-urea;
1-{3-Cyclobutoxy-5-[7-(2-trifluoromethyl-pyrimidin-4-yl)-imidazo[1,2-a]pyridin-3-yl]-phenyl}-3-(2,2,2-trifluoro-ethyl)-urea;
1-{3-[7-(5-Fluoro-6-methyl-pyridin-2-yl)-imidazo[1,2-a]pyridin-3-yl]-5-isopropoxy-phenyl}-3-(2,2,2-trifluoro-ethyl)-urea;
1-{3-[7-(6-Amino-2-methyl-pyrimidin-4-yl)-imidazo[1,2-a]pyridin-3-yl]-5-isopropoxy-phenyl}-3-(2,2,2-trifluoro-ethyl)-urea;
1-[3-Isopropoxy-5-(7-[1,3,4]oxadiazol-2-yl-imidazo[1,2-a]pyridin-3-yl)-phenyl]-3-(2,2,2-trifluoro-ethyl)-urea;
1-Isobutyl-3-{3-isopropoxy-5-[7-(5-methyl-[1,3,4]oxadia-zol-2-yl)-imidazo[1,2-a]pyridin-3-yl]-phenyl}-urea;
and
1-{3-[7-(6-Dimethylamino-pyrimidin-4-yl)-imidazo[1,2-a]pyridin-3-yl]-5-isopropoxy-phenyl}-3-(2,2,2-trifluoro-ethyl)-urea.

In one embodiment, the compound of formula (I) is a compound selected from:
1-{3-Isopropoxy-5-[7-(4-methylimidazol-1-yl)-imidazo[1,2-a]pyridin-3-yl]-phenyl}-3-(2,2,2-trifluoro-ethyl)-urea 1-(3-{7-[4-(2-Hydroxy-1,1-dimethylethyl)-pyrimidin-2-yl]-imidazo[1,2-a]pyridin-3-yl}-5-isopropoxy-phenyl)-3-(2,2,2-trifluoro-ethyl)-urea
1-Ethyl-3-{3-isopropoxy-5-[7-(5-methyl-[1,3,4]thiadiazol-2-yl)-imidazo[1,2-a]pyridin-3-yl]-phenyl}-urea
1-{3-Isopropoxy-5-[7-(5-methyl-[1,3,4]oxadiazol-2-yl)-imidazo[1,2-a]pyridin-3-yl]-phenyl}-3-(2,2,2-trifluoro-ethyl)-urea
1-{3-Isopropoxy-5-[7-(5-methyl-[1,3,4]oxadiazol-2-yl)-imidazo[1,2-a]pyridin-3-yl]-phenyl}-3-(2,2,2-trifluoro-1-hydroxyethyl)-urea
1-{3-Isopropoxy-5-[7-(4-isopropyl-pyrimidin-2-yl)-imidazo[1,2-a]pyridin-3-yl]-phenyl}-3-(2,2,2-trifluoroethyl)-urea
1-{3-Methylaminomethyl-5-[7-(5-methyl-[1,3,4]oxadiazol-2-yl)-imidazo[1,2-a]pyridin-3-yl]-phenyl}-3-(2,2,2-trifluoroethyl)-urea
1-{3-Dimethylaminomethyl-5-[7-(5-methyl-[1,3,4]oxadia-zol-2-yl)-imidazo[1,2-a]pyridin-3-yl]-phenyl}-3-(2,2,2-trifluoroethyl)-urea
{3-Isopropoxy-5-[7-(5-methyl-[1,3,4]oxadiazol-2-yl)-imidazo[1,2-a]pyridin-3-yl]-phenyl}-urea
2-[2-(3-{3-Isopropoxy-5-[3-(2,2,2-trifluoroethyl)-ureido]-phenyl}-imidazo[1,2-a]pyridin-7-yl)-pyrimidin-4-yl]-2-methyl-propionic acid ethyl ester Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person. In particular, compounds of formula (I) are readily prepared by palladium mediated coupling chemistries between aromatic chloro, bromo, iodo, or pseudo-halogens such as a trifluoromethanesulphonate (triflate) or tosylate compounds, and aromatic boronic acids or stannane derivatives. In particular, Suzuki coupling chemistry is broadly applicable to synthesis of these compounds. The Suzuki reaction can be carried out under typical conditions in the presence of a palladium catalyst such as bis(tri-t-butylphosphine)palladium, tetrakis(triphenyl-phosphine)-palladium or a palladacycle catalyst (e.g. the palladacycle catalyst described in Bedford, R. B. and Cazin, C. S. J. (2001) *Chem. Commun.*, 1540-1541 and a base (e.g. a carbonate such as potassium carbonate) as discussed in more detail below. The reaction may be carried out in polar solvent for example an aqueous solvent system, including aqueous ethanol, or an ether such as dimethoxyethane or dioxane, and the reaction mixture is typically subjected to heating, for example to a temperature of 80° C. or more, e.g. a temperature in excess of 100° C.

As illustrated in Scheme 1, the imidazo[1,2-a]pyridine core can be synthesised from commercially available starting materials using Route A (to give a 3,7 disubstituted ring) or Route B.

4-Chloro-pyridin-2-ylamine or 4-bromo-pyridin-2-ylamine in an appropriate solvent and base can be cyclised under reflux with chloroacetaldehyde to give the imidazopyridine ring. The 7-chloro-imidazo[1,2-a]pyridine in an appropriate solvent can then be iodinated, for example using N-iodosuccininnide at room temperature.

Appropriate functionality can then be added at the halogenated positions, for example using a range of metal-catalysed reactions. In particular, appropriately functionalised boronic acids or their boronate esters may react with the aryl halide. This transformation, commonly known as the Suzuki reaction, has been reviewed by Rossi et al (2004) Synthesis, 15, 2419.

The Suzuki reaction is often carried out in mixtures of water and organic solvents. Examples of suitable organic solvents include toluene, tetrahydrofuran, 1,4-dioxane, 1,2-dimethoxyethane, acetonitrile, N-methylpyrrolidinone, ethanol, methanol and dimethylformamide. The reaction mixture is typically subjected to heating, for example to a temperature in excess of 100° C. The reaction is carried out in the presence of a base. Examples of suitable bases include sodium carbonate, potassium carbonate, cesium carbonate and potassium phosphate. Examples of suitable catalysts include bis(tri-t-butylphosphine)palladium(0), tris(dibenzylideneacetone)di-palladium(0), bis(triphenylphosphine)palladium(II) chloride, palladium(II) acetate, tetrakis(triphenylphosphine)palladium(0), bis(tricyclohexylphosphine) palladium(0), [1,1'-bis(diphenylphosphino)ferrocene]-dichloropalladium (II), dichlorobis(tri-o-tolylphosphine)palladium(II), 2'-(dimethylamino)-2-biphenylyl-palladium(II) chloride dinorbornylphosphine complex and 2-(dimethylamino)ferrocen-1-yl-palladium(II) chloride dinorbornylphosphine complex. In some cases additional ligands may be added to facilitate the coupling reaction. Examples of suitable ligands include tri-t-butylphosphine, 2,2-bis(diphenylphosphino)-1,1-binaphthyl, triphenylphosphine, 1,2-bis(diphenylphosphino)ethane, 1,1'-bis(diphenylphosphino)ferrocene, tricyclohexylphosphine, 9,9-dimethyl-4,5-bis(diphenylphosphino)xanthene, 1,3-bis(diphenylphosphino)propane, 2-(di-t-butylphosphino)biphenyl, 2-dicyclohexylphosphino-2'-(n,n-dimethylamino)biphenyl, tri-o-tolylphosphine, 2-(dicyclohexylphosphino)biphenyl, 2-dicyclohexylphosphino-2',4',6'-triisopropylbiphenyl, tri(2-furyl)phosphine, 2-dicyclohexylphosphino-2',6'-dimethoxybiphenyl and 2-di-tert-butylphosphino-2',4',6'-triisopropylbiphenyl.

Scheme 1

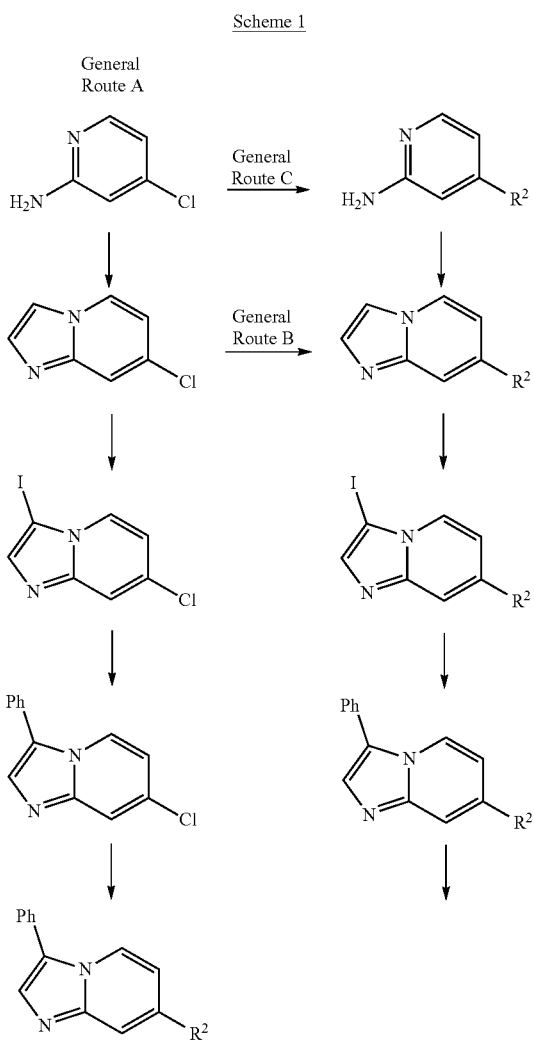

wherein Ph is a substituted phenyl as defined in Formula I

Other examples of possible metal catalysed functionalisations of the halide are reactions with organo-tin reagents (the Stille reaction), with Grignard reagents and reaction with nitrogen nucleophiles. A general overview, and further leading references, of these transformations is presented in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

A further reaction which can be utilised is the Buchwald-Hartwig type reaction (see *Review:* Hartwig, J. F. (1998) *Angew. Chem. Int. Ed.* 37, 2046-2067) which provides a means for palladium-catalyzed synthesis of aryl amines. The starting materials are aryl halides or pseudohalides (for example triflates) and primary or secondary amines, in the presence of a strong base such as sodium tert-butoxide and a palladium catalyst such as tris-(dibenzylideneacetone)-dipalladium ($Pd_2(dba)_3$), or 2,2'-bis(diphenylphosphino)-1'1-binaphthyl (BINAP).

The sequence of reactions outlined in Route A can be alternated as outlined in Route B. Alternatively the halogen functionality at the 7-position of the imidazo[1,2-a]pyridine can be converted to a boronic acid or ester and used to synthesise alternative motifs as outlined in Scheme 2. This can then be used directly in any of the metal catalysed reactions outlined herein. For example, for conversion of a halide to a boronate, the halide is reacted with a palladium catalyst and a phosphine ligand in an appropriate solvent e.g. dioxane and base e.g. KOAc, and the appropriate substituted boron compound.

Scheme 2

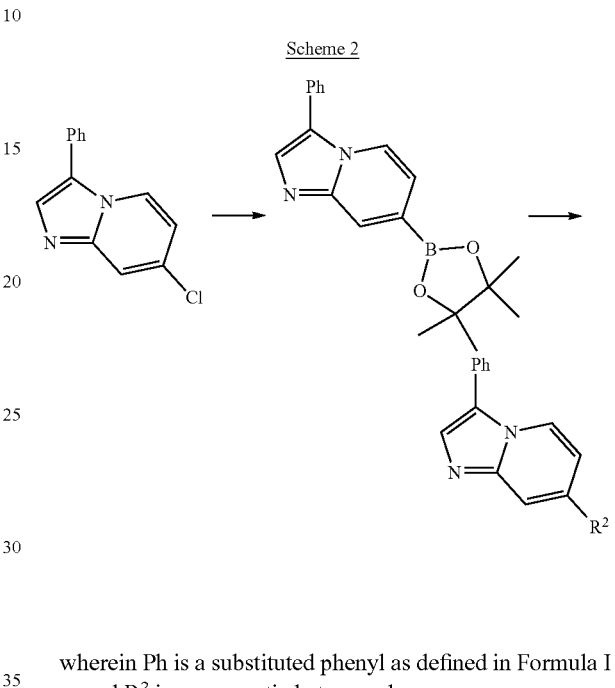

wherein Ph is a substituted phenyl as defined in Formula I and $R^2$ is an aromatic heterocycle Alternatively as illustrated in Scheme 1, the imidazo[1,2-a]pyridine core can also be synthesised from 4-chloro-pyridin-2-ylamine using Route C, wherein it is converted to a pyridin-2-ylamine substituted at the 4-position with the required $R^2$ group by heating in the presence of the appropriate nitrogen containing heterocycle. This is then used in the cyclisation reaction by heating with chloroacetaldehyde in an appropriate solvent and in the presence of base (e.g. sodium hydrocarbonate) to give the imidazopyridine ring. The 7-chloro-imidazo[1,2-a]pyridine compound in an appropriate solvent can then be iodinated, for example using N-iodosuccinimide at room temperature.

For synthesis of the $R^2$ of compounds of formula (I) wherein $R^2$ is a ketone, the carboxylic ester can be converted to the ketone as outlined in Scheme 3 below. Ketones can be synthesized from the corresponding carboxylic acid via the N,O-dimethylhydroxamic acid (Weinreb Amide) or the N-methyl, O-t-butyl hydroxamic acid (Weinreb type Amide). Derivatisation to the corresponding Weinreb Amide uses N,O-dimethylhydroxylamine hydrochloride as described in L. De Luca, G. Giacomelli, M. Taddei, J. Org. Chem., 2001, 66, 2534-2537. Conversion of the standard aromatic Weireb Amide to a methyl ketone can be achieved directly using alkylidenetriphenylphosphoranes or methylene-triphenyl-lambda*5*-phosphane in a solvent such at tetrahydrofuran as reported in Murphy, J. A. et al Org Lett 2005, 7 (7), 1427-1429. Alternatively this can be achieved stepwise by addition of a Grignard reagent (Labeeuw, O. et, al. Tetrahedron Letters 2004, 45(38), 7107-7110) and by oxidation of the resulting alcohol.

Scheme 3

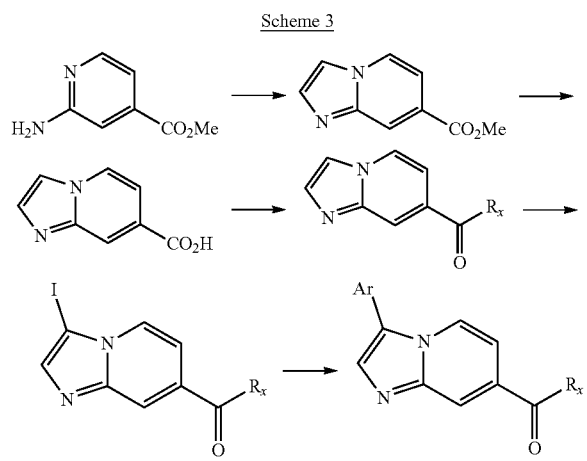

Alternatively ketones can be prepared from the chloride using vinylethertin (Stille type) coupling with haloaromatic or haloheteroaromatic. As an example the acetyl ketone can be prepared by heating tributyl-(1-ethoxy-vinyl)-stannane, lithium chloride and tetrakis(triphenylphosphine)-palladium (0) in solvent such as acetonitrile or via a Heck type reaction reported in Mo, J. Angew Chem, Int Ed, 2006, 45(25), 4152.

Ketone compounds can also be prepared using cross-coupling reactions, for example palladium mediated (Tetrahedron Lett., 1997, 38 (11), 1927-1930) or copper mediated (Org. Lett., 2003, 5 (8), 1229-1231) reaction can be performed with the appropriate acid chloride with the appropriate 7-chloroimidazopyridinyl compound.

Alternatively an aldehyde intermediate can be converted to the desired ketone.

The aldehyde intermediate in THF dry can be converted to a ketone using Grignard reagent e.g. cyclopropylmagnesium bromide under an inert atmosphere and than oxidation e.g. using manganese oxide to the ketone. For example, to imidazo[1,2-a]pyridine-7-carboxaldehyde in aprotic solvent THF can be added to cyclopropylmagnesium bromide in THF under an inert atmosphere, and the resulting hydroxyl compound can then be oxidized to the cyclopropyl ketone.

Compounds where $R^2$ is $OR^x$, can be synthesised from imidazo[1,2-a]pyridin-7-olusing protected bromo-alkoxy compounds e.g. bromo-ethoxyTHP in the presence of base e.g. $K_2CO_3$. The reagents are heated e.g in DMF. The resulting compound can be iodinated for example using 1-iodo-2,5-pyrrolidinedione. Suzuki coupling and deprotection result in the desired compound.

Once synthesised, a range of functional group conversions can be employed on di-aryl or alkynynl substituted imidazopyridine compounds to produce further compounds of formula (I). For example, some of the following reactions can be used hydrogenation e.g. using Raney nickel catalyst, hydrolysis, deprotection, and oxidation.

In particular for synthesis compounds of formula (I), the imidazopyridine halide can be reacted with 3-aminobenzeneboronic acid using an appropriate metal catalyst e.g. bis(triphenylphosphine)palladium(II) chloride, to form the amino precursor for urea bond formations. As outlined Scheme 4, the amine functionality introduced can be used to synthesise ureas.

Scheme 4

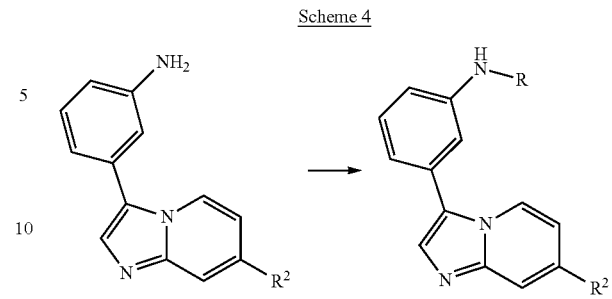

Ureas can be prepared using standard methods. For example, such compounds can be prepared by reacting an amino compound with a suitably substituted isocyanate in a polar solvent such as DMF. The reaction is conveniently carried out at room temperature.

Alternatively, ureas of the formula (I) can be prepared by reacting an amine with an appropriately substituted amine in the presence of carbonyl diimidazole (CDI). The reaction is typically carried out in a polar solvent such as THF with heating (for example using a microwave heater) to a temperature of up to about 150° C. Instead of using CDI, the coupling of the two amines to form the urea can be effected using triphosgene (bis(trichloromethyl)carbonate) in the presence of a non-interfering base such as triethylamine, in a solvent such as dichloromethane at room temperature or below. As a further alternative to CDI, phosgene may be used instead of triphosgene.

A further method for synthesising the urea functionality is by reacting the amine compound with p-nitrophenol chloroformate under conditions well known to the skilled person. The resulting carbamate compound is then reacted with the appropriate amine for example trifluoroethylamine or cyclopropylamine.

In addition the urea compounds can be synthesised by use of the appropriate substituted boronic acid in the Suzuki reaction e.g. 1-methyl-3-[3-(4,4,5,5-tetramethyl-[1,3,2]dioxaborolan-2-yl)-phenyl]-urea or 3-methoxy-5-nitro-phenyl boronic acid pinacol ester. These can be synthesised as described herein.

Ureas can also be synthesised from the amine intermediate using a range of well known functional group interconversions as described in *Advanced Organic Chemistry* by Jerry March, 4th Edition, John Wiley & Sons, 1992.

Appropriate starting material and reagents for these reactions can be obtained commercially or by any of a large number of standard synthetic methods well known those skilled in the art, for example see *Advanced Organic Chemistry* by Jerry March, 4th Edition, John Wiley & Sons, 1992, and *Organic Syntheses*, Volumes 1-8, John Wiley, edited by Jeremiah P. Freeman (ISSN: 0-471-31192-8), 1995, and see also the methods described in the experimental section below. For example, a range of appropriate functionalized aniline and amino pyridine starting materials, and metal catalysts are commercially available.

In particular, heterocyclic halide or pseudo-halide precursors are commercially available or can be prepared from an appropriately functionalised heterocyclic compound. Alternatively the $R^2$ rings can be formed on the imidazopyridine scaffold using intramolecular or radical cyclisation reactions under standard conditions. For example the imidazo[1,2-a]pyridine-7-carboximidic acid methyl ester or imidazo[1,2-a]pyridine-7-methyl ester are reacted with hydrazine hydrate to generate the hydrazide. Triazines can then be synthesized by reacting the hydrazide with the appropriate aldehyde in the presence or absence of ammonia (e.g. the carboxylic acid hydrazide, pyruvic aldehyde and ammonia to create methyltriazine or the carboximidic acid hydrazide and glyoxal to give triazine) or with the appropriate ketone (e.g. diacetyl to create dimethyltriazine). Alternatively the carboxylic acid hydrazide is reacted with triethyl orthoacetate to give methyloxadiazole, or an isothiocyanato group to give substituted thiadiazole (e.g. isothiocyanatocyclopropane to give cyclopropyl-thiadiazol-2-yl-amine).

Many boronates, for example boronic acids or esters or trifluoroborates, suitable for use in preparing compounds of the invention are commercially available, for example from Boron Molecular Limited of Noble Park, Australia, or from Combi-Blocks Inc. of San Diego, USA. Where the appropriately substituted boronate is not commercially available, they can be prepared by methods known in the art, for example as described in the review article by Miyaura, N. and Suzuki, A. (1995) *Chem. Rev.*, 95, 2457. Thus, boronates can be prepared by reacting the corresponding bromo-compound with an alkyl lithium such as butyl lithium and then reacting with a borate ester e.g. ($^{i}$PrO)$_3$B. The reaction is typically carried out in a dry polar solvent such as tetrahydrofuran at a reduced temperature (for example −78° C.). Boronate esters (for example a pinacolatoboronate) can also be prepared from a bromo-compound by reaction with a diboronate ester such as bis(pinacolato)diboron in the presence of a phosphine such as tricyclohexyl-phosphine and a palladium (0) reagent such as tris(dibenzylideneacetone)-dipalladium (0). The formation of the boronate ester is typically carried out in a dry polar aprotic solvent such as dioxane or DMSO with heating to a temperature of up to about 100° C., for example around 80° C. The resulting boronate ester derivative can, if desired, be hydrolysed to give the corresponding boronic acid or converted into the trifluoroborate.

Trisubstituted boronates of formula (V) below can be synthesised from the appropriately substituted 3-urea halogenated compound as described above. In one method, the halide compound is reacted with 4,4,4',4',5,5,5',5'-octamethyl-2,2'-bi-1,3,2-dioxaborolane, 1,1'bis(diphenylphosphino)ferrocenedichloro palladium and potassium acetate in dimethyl sulfoxide to form the compound of formula (V).

The R$^a$ group can be synthesised by known functional group interconversions. For example R$^a$ groups containing amines can be synthesised by unmasking of a dioxolane to reveal the aldehyde using acid (e.g. HCl) and then reductive amination of the aldehyde using the appropriate amine (e.g. dimethylamine hydrochloride) and sodium cyanoborohydride, or by amination of a haloalkyl group using the appropriate amine (e.g. methylamine), or by use of the Curtius rearrangement by reacting the carboxylic acid with azide. The amine can then be further functionalised using reductive amination for example using the appropriate ketone and sodium cyanoborohydride. Intermediates of formula (V) can be synthesised where R$^a$ is alkoxy by using alkylation of a hydroxyl group for example using haloalkyl groups (e.g. iodoethane, bromocyclobutane, 2-bromopropane) in the presence of base (e.g. K$_2$CO$_3$).

The appropriately substituted 3-urea 5-halide compound can be synthesised using amine to urea conversions as described herein. In one particular method the appropriately functionalised amine compound can be reacted with 4-nitrophenyl carbonochloridic acid, ester followed by addition of N,N-diethylethanamine and 2,2,2-trifluoroethanamine 5%.

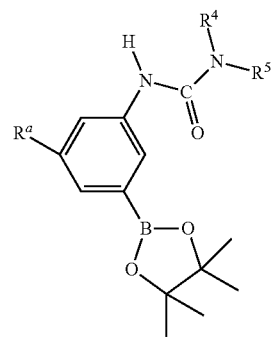

(V)

The appropriately substituted 3-amino halogenated compound can be synthesised by a range of functional groups conversions well know to a person skilled in the art. These transformations can be performed in any order as required based on the availability of required starting materials.

For example, from 3-bromo-5-nitrophenol using 2-iodopropane in the presence of base e.g. K$_2$CO$_3$, in solvent such as DMF at room temperature the 3-bromo-5-nitro alkoxy compound can be synthesised. The nitro group is then reduced to the amine using well known techniques for example TiCl$_3$ in THF at room temperature.

Alternatively appropriately functionalized trisubstituted compounds can be synthesized from 3-bromo-5-hydroxylbenzoic acid using bromocyclobutane and base e.g. potassium carbonate in DMF stirring at 60° C. overnight. The carboxylic acid and the phenol are alkylated in this reaction and the carboxylic acid can be hydrolysed using saponification. This acid can then be reacted with diphenylphosphoryl azide and triethylamine in 2-methyl-2-propanol to generate the carbamate which can then be deprotected with TFA to reveal the amine.

Reduction of the nitro group of 3-bromo-5-nitro-benzenemethanol can also be preformed using hydrogenation in the presence of Raney nickel. The alcohol can then be alkylated using iodomethane in the presence of base such as sodium hydride in dry THF 2-amino-5-nitro-phenol can be alkylated as described above and then iodinated using iodine monochloride. The 2-amino can then be removed and the nitro groups reduced as described above.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, —OAc). An aldehyde or ketone group may be protected, for example, as an acetal (R—CH(OR)$_2$) or ketal (R$_2$C(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$alkyl ester (e.g., a methyl ester; a t-butyl ester); a C$_{1-7}$ haloalkyl ester (e.g., a C$_{1-7}$ trihaloalkyl ester); a triC$_{1-7}$alkylsilyl-C$_{1-7}$alkyl ester; or a C$_{5-20}$ aryl-C$_{1-7}$alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Key intermediates in the preparation of the compounds of formula (I) are the compounds of formula (XX) below. Novel chemical intermediates of the formula (XX) form a further aspect of the invention. The novel chemical intermediates may be protected and a protected form of the novel chemical intermediates of the formula (XX) form a further aspect of the invention.

A further aspect of the invention is a process for the preparation of a compound of formula (I) as defined herein, which process comprises:
(I) the reaction of a compound of the formula (XX):

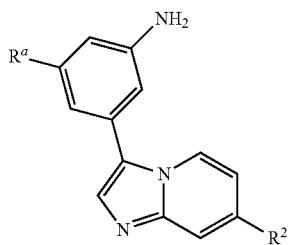

(XX)

or a protected form thereof, wherein R$^a$ and R$^2$ are as defined hereinbefore, with an appropriately substituted isocyanate or an appropriately substituted amine in the presence of carbonyl diimidazole (CDI) and thereafter removing any protecting group present; or
(ii) reacting a compound of formula (V) and (VI):

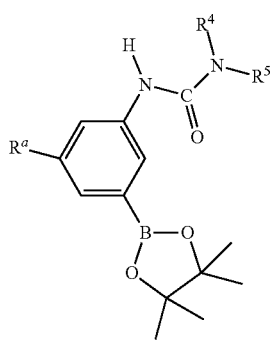

(V)

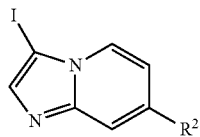

(VI)

wherein R$^a$, R$^2$, R$^4$ and R$^5$ are as defined above for compounds of formula (I) for example, using a Suzuki reaction;
and optionally thereafter converting one compound of the formula (I) into another compound of the formula (I).

In one embodiment, R$^4$ represents hydrogen and R$^5$ represents ethyl or CH$_2$CF$_3$. In an alternative embodiment, R$^4$ represents hydrogen and R$^5$ represents cyclopropyl. In an alternative embodiment, R$^4$ and R$^5$ both represent hydrogen.

According to a further aspect of the invention there is provided a novel intermediate as described herein.
Pharmaceutically Acceptable Salts, Solvates or Derivatives Thereof.

In this section, as in all other sections of this application, unless the context indicates otherwise, references to formula (I) include references to all other sub-groups, preferences and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wernnuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic. D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic. L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric. DL-Lactic, fumaric, gluconic, glucuronic, hippuric, hydrochloric, glutamic. DL-malic, methanesulphonic, sebacic, stearic, succinic and tartaric acids.

The compounds of the invention may exist as mono- or di-salts depending upon the pKa of the acid from which the salt is formed.

If the compound is anionic, or has a functional group which may be anionic (e.g., —COOH may be —COM, then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertian/amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds on the invention in combination with water, isopropanol, ethanol, methanol. DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation using crystallisation conditions that include an amount of the solvent required for the particular solvate. Thereafter the standard methods described above, can be used to establish whether solvates had formed.

Furthermore, the compounds of the present invention may have one or more polymorph, amorphous or crystalline forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Other examples of tautomeric forms include, for example, keto-, enol-, and enolate-forms, as in, for example, the following tautomeric pairs: keto/enol (illustrated below), imine/enamine, amide/imino alcohol, amidine/enediamine, nitroso/oxime, thioketone/enethiol, and nitro/aci-nitro.

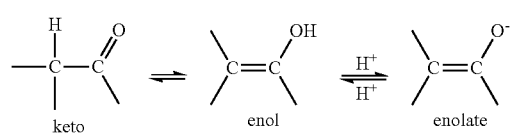

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog (1966) *Angew. Chem. Int. Ed. Engl.*, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and prodrugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonyloxyethyl; 1-(benzoyloxy)ethyl; isopropoxy-carbonyloxymethyl;
1-isopropoxy-carbonyloxyethyl; cyclohexyl-carbonyloxymethyl; 1-cyclohexyl-carbonyloxyethyl; cyclohexyloxy-carbonyloxymethyl;
1-cyclohexyloxy-carbonyloxyethyl; (4-tetrahydropyranyloxy)carbonyloxymethyl; 1-(4-tetrahydropyranyloxy)carbonyloxyethyl;
(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof.

According to a further aspect of the invention there is provided a compound as defined herein or a salt or solvate thereof.

References to compounds of the formula (I) and subgroups thereof as defined herein include within their scope the salts or solvates or tautomers or N-oxides of the compounds.

Protein Tyrosine Kinases (PTK)

The compounds of the invention described herein inhibit or modulate the activity of certain tyrosine kinases, and thus the compounds will be useful in the treatment or prophylaxis of disease states or conditions mediated by those tyrosine kinases in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Ozawa, et al. (2001), Teratog. Carcinog. Mutagen., 21, 27-44).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or transphosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The overexpression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2 (Lemonnier, et al. (2001), J. Bone Miner. Res., 16, 832-845). In addition, mutation screening in patients with syndromic craniosynostoses indicates that a number of recurrent FGFR2 mutations accounts for severe forms of Pfeiffer syndrome (Lajeunie et al, European Journal of Human Genetics (2006) 14, 289-298). Particular mutations of FGFR2 include W290C, D321A, Y3400, C342R C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al. (1996) Am. J. Hum. Genet., 58, 491-498; Plomp, et al. (1998) Am. J. Med. Genet., 75, 245-251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2 (Yu, et al. (2000), Proc. Natl. Acad. Sci. U.S.A., 97, 14536-14541).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J. (2000), et al., Endocr. Rel. Cancer, 7, 165; Qiu, W. et. al. (2005), World Journal Gastroenterol, 11(34)). Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC) (Journal of Pathology (2007), 213 (1), 91-98). Increased expression was associated with mutation (85% of mutant tumors showed high-level expression) but also 42% of tumors with no detectable mutation showed over-expression, including many muscle-invasive tumors.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat. S., et al. (2002) The Journal of Clinical Investigation, 109, 1; Wang et al. (2004) Clinical Cancer Research, 10). In addition a germline polymorphism (Gly388Arg) is associated with increased incidence of lung, breast, colon and prostate cancers (Wang et al., (2004) Clinical Cancer Research, 10). In addition, a truncated form of FGFR4 (including the kinase domain) has also been found to present in 40% of pituitary tumours but not present in normal tissue. FGFR4 overexpression has been observed in liver, colon and lung tumours (Desnoyers et al. (2008) Oncogene, 27; Ho et al. (2009) Journal of Hepatology, 50). These studies described targeting of either FGFR4 kinase activity or its ligand FGF 19 with an antibody antagonist inhibited proliferation and induced apoptosis in cell line models. Ho et al showed that one third of patients with a common polymorphism in the FGFR4 gene expressed high levels of mRNA and these tumours were associated with high secreted levels of the hepatocellular carcinoma marker alpha-fetoprotein.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006) Clin Cancer Res. 12(22): 6652-6662.

Rhabdomyosarcoma (RMS), the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes (Genes, Chromosomes & Cancer (2007), 46(11), 1028-1038).

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al. (1997 & 2002); Barrios, et al. (1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman (1997), 79, 1-81; Folkman (1995), *Nature Medicine*, 1, 27-31; Folkman and Shing (1992) *J. Biol. Chem.*, 267, 10931).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott (1992), *Ann. Rhum. Dis.*, 51, 919).

In diabetes (and in many different eye diseases), new vessels invade the macula or retina or other ocular structures, and may cause blindness (Brooks, et al. (1994) *Cell*, 79, 1157). The process of atherosclerosis has been linked to angiogenesis (Kahlon, et al. (1992) *Can. J. Cardiol.*, 8, 60). Tumor growth and metastasis have been found to be angiogenesis-dependent (Folkman (1992), *Cancer Biol*, 3, 65; Denekamp, (1993) *Br. J. Rad.*, 66, 181; Fidler and Ellis (1994), *Cell*, 79, 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial ells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al. (1994) *Cell*, 79, 315; Ingber, et al. (1990) *Nature*, 348, 555), ocular diseases (Friedlander, et al. (1995) *Science*, 270, 1500), arthritis (Peacock, et al. (1992), *J. Exp. Med.*, 175, 1135; Peacock et al. (1995), *Cell. Immun.*, 160, 178) and hemangioma (Taraboletti, et al. (1995) *J. Natl. Cancer Inst.*, 87, 293).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo. H. M., et al. (2000), *The Oncologist*, 5(90001), 1-2). VEGFR(s) are protein tyrosine kinases (PTKs). PTKs catalyze the phosphorylation of specific tyrosine residues in proteins involved in cell function thus regulating cell growth, survival and differentiation. (Wilks, A. F. (1990), *Progress in Growth Factor Research*, 2, 97-111; Courtneidge, S. A. (1993) *Dev. Supp.l*, 57-64; Cooper, J. A. (1994), *Semin. Cell Biol.*, 5(6), 377-387; Paulson, R. F. (1995), *Semin. Immunol.*, 7(4), 267-277; Chan, A. C. (1996), *Curr. Opin. Immunol.*, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. (1995), et al., *J. Cell Biol.*, 129, 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G. (2000), *The Oncologist*, 5(90001), 3-10).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition. Inhibition of VEGFR2 but not VEGFR1 markedly disrupted angiogenic switching, persistent angiogenesis, and initial tumor growth. In late-stage tumours, phenotypic resistance to VEGFR2 blockade emerged, as tumours regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

A FGF-trap adenovirus has been previously reported to bind and block various ligands of the FGF family, including FGF1, FGF3, FGF7, and FGF10, thereby effectively inhibiting angiogenesis in vitro and in vivo. Indeed, adding the FGF-trap treatment in the regrowth phase of a mouse model produced a significant decrease in tumor growth compared to anti-VEGFR2 alone. This decrease in tumor burden was accompanied by a decrease in angiogenesis that was observed as decreased intratumoral vessel density.

Batchelor et al, (Batchelor et al, 2007, *Cancer Cell*, 11(1), 83-95) provide evidence for normalization of glioblastoma blood vessels in patients treated with a pan-VEGF receptor tyrosine kinase inhibitor. AZD2171, in a phase 2 study. The rationale for using AZD2171 was based partially on results showing a decrease in perfusion and vessel density in an in vivo breast cancer model (Miller et al., 2006, *Clin. Cancer Res.* 12, 281-288). Furthermore, using an orthotopic glioma model, it had previously been identified that the optimal window of time to deliver anti-VEGFR2 antibody to achieve a synergistic effect with radiation. During the window of normalization, there was improved oxygenation, increased pericyte coverage, and upregulation of angiopoietin-1 leading to a decrease in interstitial pressure and permeability within the tumour (Winkler et al., 2004, *Cancer Cell* 6, 553-563). The window of normalization can be quantified using magnetic resonance imaging (MRI) using MRI gradient echo, spin echo, and contrast enhancement to measure blood volume, relative vessel size, and vascular permeability.

The authors showed that progression on treatment with AZD2171 was associated with an increase in CECs. SDF1, and FGF2, while progression after drug interruptions correlated with increases in circulating progenitor cells (CFCs) and plasma FGF2 levels. The increase in plasma levels of SDF1 and FGF2 correlated with MRI measurements, demonstrated an increase in the relative vessel density and size. Thus, MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3 (trifluoromethyl)phenyl)ureido)phenoxy)-N2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper-(or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactoral aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, it is envisaged that the compounds of the invention will be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3.

Preferred compounds are compounds that inhibit one or more FGFR selected from FGFR1. FGFR2 and FGFR3, and also FGFR4. Preferred compounds of the invention are those having $IC_{50}$ values of less than 0.1 μM.

Compounds of the invention also have activity against VEGFR.

Compounds of the invention also have activity against PDGFR kinases. In particular, the compounds are inhibitors of PDGFR and, for example, inhibit PDGFR A and/or PDGFR B.

In addition many of the compounds of the invention exhibit selectivity for the FGFR 1, 2, and/or 3 kinase, and/or FGFR4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or FGFR4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, VEGFR and/or PDGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1. FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma; hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis.

Thus, in the pharmaceutical compositions, uses or methods of this invention for treating a disease or condition comprising abnormal cell growth, the disease or condition comprising abnormal cell growth in one embodiment is a cancer.

Further T-cell lymphoproliferative diseases include those derived from natural Killer cells. The term B-cell lymphoma includes diffuse large B-cell lymphoma.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

A further example of a tumour of mesenchymal origin is Ewing's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

It is further envisaged that the compound of the invention having FGFR such as FGFR1 inhibitory activity, will be particularly useful in the treatment or prevention of breast cancer in particular Classic Lobular Carcinomas (CLC).

As the compounds of the invention have FGFR4 activity they will also be useful in the treatment of prostate or pituitary cancers.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful for the treatment of lobular carcinomas such as CLC (Classic lobular carcinoma).

As the compounds have activity against FGFR3 they will be useful in the treatment of multiple myeloma and bladder.

In particular the compounds are useful for the treatment of g(4;14) translocation positive multiple myeloma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR, VEGFR or PDGFR signalling may be determined by means of a cell growth assay as set out below or by a method as set out in the section headed "Methods of Diagnosis".

It is further envisaged that the compounds of the invention, and in particular those compounds having FGFR, VEGFR or PDGFR inhibitory activity, will be particularly useful in the treatment or prevention of cancers of a type associated with or characterised by the presence of elevated levels of FGFR, VEGFR or PDGFR, for example the cancers referred to in this context in the introductory section of this application.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

It is also envisaged that the compounds of the invention will be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of inflammatory diseases, cardiovascular diseases and wound healing.

FGFR. VEGFR and PDGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

It is further envisaged that the compound of the invention having FGFR such as FGFR2 or FGFR3 inhibitory activity, will be particularly useful in the treatment or prevention of the skeletal diseases. Particular skeletal diseases are achondroplasia or thanatophoric dwarfism (also known as thanatophoric dysplasia).

It is further envisaged that the compound of the invention having FGFR such as FGFR1. FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which it is envisaged will be useful in preventing or treating disease states or conditions mediated by FGFR kinases.

In one embodiment, there is provided a compound as defined herein for use in therapy. In a further embodiment, there is provided a compound as defined herein for use in the prophylaxis or treatment of a disease state or condition mediated by a FGFR kinase. In one embodiment disease state or condition mediated by a FGFR kinase is cancer.

Thus, for example, it is envisaged that the compounds of the invention will be useful in alleviating or reducing the incidence of cancer. Therefore, in a further embodiment, there is provided a compound as defined herein for use in the prophylaxis or treatment of cancer.

Accordingly, in one aspect, the invention provides the use of a compound for the manufacture of a medicament for the prophylaxis or treatment of a disease state or condition mediated by a FGFR kinase, the compound having the formula (I) as defined herein.

In one embodiment, there is provided the use of a compound as defined herein for the manufacture of a medicament for the prophylaxis or treatment of a disease state or condition as described herein.

In a further embodiment, there is provided the use of a compound as defined herein for the manufacture of a medicament for the prophylaxis or treatment of cancer.

Accordingly, the invention provides inter alia:

A method for the prophylaxis or treatment of a disease state or condition mediated by a FGFR kinase, which method comprises administering to a subject in need thereof a compound of the formula (I) as defined herein.

In one embodiment, there is provided a method for the prophylaxis or treatment of a disease state or condition as described herein, which method comprises administering to a subject in need thereof a compound of the formula (I) as defined herein.

In a further embodiment, there is provided a method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use as a modulator (e.g. inhibitor) of FGFR.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Aped (AP) syndrome, Crouzon syndrome, Jackson-Weiss syndrome, Beare-Stevenson cutis gyrate syndrome. Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme (Carter et al (2005), PNAS, 102(31), 11011-110116).

A study in gastric cancer patient samples showed the presence of two mutations in FGFR2, Ser167Pro in exon 111a and a splice site mutation 940-2A-G in exon 111c. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group (Jang et. al. (2001) Cancer Research 61 3541-3543.

There are mutations that have been observed in PDGFR in imatinib-treated patients, in particular the T674I mutation. The clinical importance of these mutations may grow considerably, as to date it appears to represent the primary mechanism of resistance to src/Abl inhibitors in patients.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR or PDGFR including PDGFR-beta and PDGFR-alpha in particular the T674I mutation of PDGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1V561M showed that this mutation conferred resistance to a tyrosine kinase inhibitor compared to that of the wild type.

Advantages of the Compositions of the Invention

The compounds of the formula (I) have a number of advantages over prior art compounds.

For example, the compounds of formula (I) have advantageous ADMET and physiochemical properties over prior art compounds.

In addition the compounds may have improved selectivity in particular with regard to VEGFR2 and Flt3. The compounds may also have reduced tubulin binding.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions. The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly (2004), Solubilizing Excipients in oral and injectable formulations, Pharmaceutical Research, Vol 21(2), p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman (1971), J. Pharm. Sci., 60, 1281-1300) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

The skilled person will have the expertise to select the appropriate amounts of ingredients for use in the formulations. For example tablets and capsules typically contain 0-20% disintegrants, 0-5% lubricants, 0-5% flow aids and/or 0-100% fillers/or bulking agents (depending on drug dose). They may also contain 0-10% polymer binders, 0-5% antioxidants, 0-5% Pigments. Slow release tablets would in addition contain 0-100% polymers (depending on dose). The film coats of the tablet or capsule typically contain 0-10% polymers, 0-3% pigments, and/or 0-2% plasticizers.

Parenteral formulations typically contain 0-20% buffers, 0-50% cosolvents, and/or 0-100% Water for Injection (WFI) (depending on dose and if freeze dried). Formulations for intramuscular depots may also contain 0-100% oils.

Examples of Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at ($-45°$ C.). The temperature is raised to $-10°$ C. for annealing, then lowered to freezing at $-45°$ C., followed by primary drying at $+25°$ C. for approximately 3400 minutes, followed by a secondary drying with increased steps if temperature to $50°$ C. The pressure during primary and secondary drying is set at 80 millitor.

Methods of Treatment

It is envisaged that the compounds of the formula (I) and sub-groups thereof as defined herein will be useful in the prophylaxis or treatment of a range of disease states or conditions mediated by FGFR. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic.

However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and, Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromboembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against FGFR, VEGFR and/or PDGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, VEGFR and/or PDGFR or to sensitisation of a pathway to normal FGFR. VEGFR and for PDGFR activity, or to upregulation of these growth factor signalling pathways such as growth factor ligand levels or growth factor ligand activity or to upregulation of a biochemical pathway downstream of FGFR, VEGFR and/or PDGFR activation.

Examples of such abnormalities that result in activation or sensitisation of the FGFR, VEGFR and/or PDGFR signal include loss of, or inhibition of apoptotic pathways, up-regulation of the receptors or ligands, or presence of mutant variants of the receptors or ligands e.g PTK variants. Tumours with mutants of FGFR1. FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al. (2001), J. Bone Miner. Res., 16, 832-845). In particular activating mutations in FGFR2 have been identified in 10% of endometrial tumours (Pollock et al, Oncogene, 2007, 26, 7158-7162).

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al. (2000), Endocr. Rel. Cancer, 7, 165). A particular mutation T674I of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006), Clin Cancer Res. 12(22), 6652-6662).

Alternatively, a biological sample taken from a patient may be analysed for loss of a negative regulator or suppressor of FGFR, VEGFR or PDGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, VEGFR and/or PDGFR. The term diagnosis includes screening. By marker we include genetic markers including, for example, the measurement of DNA composition to identify mutations of FGFR, VEGFR and/or PDGFR. The term marker also includes markers which are characteristic of up regulation of FGFR, VEGFR and/or PDGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH). Identification of an individual carrying a mutation in FGFR. VEGFR and/or PDGFR may mean that the patient would be particularly suitable for treatment with a FGFR, VEGFR and/or PDGFR inhibitor. Tumours may preferentially be screened for presence of a FGFR, VEGFR and/or PDGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel. F. M. et al., eds. (2004) Current Protocols in Molecular Biology, John Wiley & Sons Inc., or Innis. M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel. F. M. et al., eds. (2004) Current Protocols in Molecular Biology, John Wiley & Sons Inc and Fluorescence In Situ Hybridization Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT) 24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR. VEGFR and/or PDGFR, or detection of FGFR. VEGFR and/or PDGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105 (Mineo et al. (2004) J Clin Pathol. 57(6), 591-7).

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevalence: R248C, S249C, G372C, S373C, Y375C, K652Q. In addition, a Gly388Arg polymorphism in FGFR4 has been found to be associated with increased incidence and aggressiveness of prostate, colon, lung and breast cancer.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S2490, G372C, S373C, Y375C, K652Q mutations in FGFR3 and Gly388Arg polymorphism in FGFR4.

In another aspect of the inventions includes a compound of the invention for use in the prophylaxis or treatment of cancer in a patient selected from a sub-population possessing a variant of the FGFR gene (for example G6970 mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

General Synthetic Routes

The following examples illustrate the present invention but are examples only and are not intended to limit the scope of the claims in any way.

EXPERIMENTAL PART

Hereinafter, "DCM" is defined as dichloromethane, "DMF" is defined as N,N-dimethylformamide, "Et$_2$O" is defined as diethylether, 'DMSO' is defined as dimethylsulfoxide, "AcOEt" is defined as ethyl acetate, "EtOH" is defined as ethanol, "MeOH" is defined as methanol, "TFA" is defined as trifluoroacetic acid, "THF" is defined as tetrahydrofuran and "DIPE" is defined as diisopropyl ether.

A. Preparation of the Intermediate Compounds

Example A1

A1.a) Preparation of Intermediate

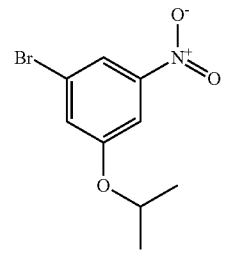

A solution of 3-bromo-5-nitrophenol (16 g, 73.39 mmol), 2-iodopropane (14.68 ml, 146.79 mmol) and K$_2$CO$_3$ (20.29 g, 146.79 mmol) in DMF (80 ml) was stirred overnight at room temperature. The reaction mixture was poured into water and AcOEt. The organic layer was washed with water then brine, dried over MgSO$_4$, filtered and the solvent was evaporated to give 18.3 g (95.9%) of intermediate shown.

A1.b) Preparation of Intermediate

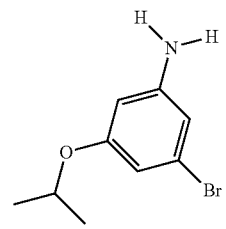

TiCl$_3$ (474.53 ml, 553.66 mmol) was added dropwise to a solution of intermediate of example A1.a (16 g, 61.52 mmol) in THF (240 ml) at room temperature. The mixture was stirred at room temperature for 2 days. Water and AcOEt were added. K$_2$CO$_3$ powder was added until basic pH. The mixture was filtered over celite. Celite was washed with AcOEt. The organic layer was separated, dried over MgSO$_4$, filtered and evaporated, yielding 14 g (98.9%) of intermediate shown.

A1.c) Preparation of Intermediate

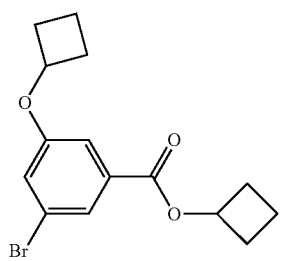 [SMILES: O=C(OC1CCC1)c1cc(Br)cc(OC2CCC2)c1]

A mixture of 3-bromo-5-hydroxylbenzoic acid (5 g, 23 mmol), bromocyclobutane (6.5 ml, 69 mmol) and potassium carbonate (12.7 g, 92 mmol) in DMF (50 ml) was stirred at 60° C. overnight. Water was added and the mixture was extracted twice with diethyl ether. The combined organic layers were washed with water, dried over MgSO₄, filtered and evaporated, yielding 3.9 g of intermediate shown.

A1.d) Preparation of Intermediate

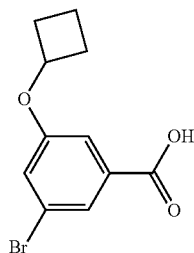 [SMILES: O=C(O)c1cc(Br)cc(OC2CCC2)c1]

Intermediate of example A1.c (3.9 g, 12 mmol) in sodium hydroxide (12 ml, 36 mmol) and ethanol (10 ml) was stirred at 60° C. overnight. After cooling down to room temperature, ethanol was evaporated. The residue was taken up into water and washed with EtOAc. The aqueous layer was made acid with hydrochloric acid 3N and extracted twice with DCM. The organic layer was dried over MgSO₄, filtered and evaporated, yielding 3.09 g of intermediate shown.

A1.e) Preparation of Intermediate

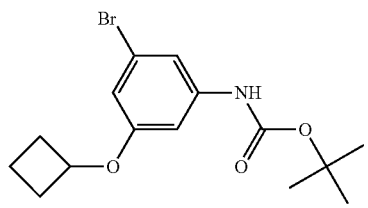 [SMILES: CC(C)(C)OC(=O)Nc1cc(Br)cc(OC2CCC2)c1]

Diphenylphosphoryl azide (2.6 ml, 12 mmol) was added to a solution of intermediate of example A1.d (3.1 g, 11.4 mmol) and triethylamine (1.75 ml, 12.5 mmol) in 2-methyl-2-propanol (20 ml) at room temperature. The mixture was stirred at reflux for 24 hours. After cooling down to room temperature, the solvent was evaporated. The residue was taken up into diethyl ether, washed successively with NaOH 3N (twice) and water. The organic layer was dried over MgSO₄, filtered and evaporated. The residue (3.8 g) was purified by Normal phase on (Spherical SiOH 10 μm 60 g PharmPrep MERCK). Mobile phase (90% Heptane, 10% ethyl acetate). The pure fractions were collected and the solvent was evaporated, yielding 2.18 g of intermediate shown.

A1.f) Preparation of Intermediate

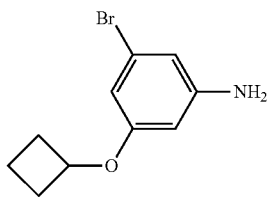 [SMILES: Nc1cc(Br)cc(OC2CCC2)c1]

Intermediate of example A1.e (2.18 g, 6.37 mmol) and TFA (3.9 ml, 51 mmol) in DCM (30 L) were stirred at room temperature. The solvent was evaporated. AcOEt and 3N NaOH solution were added and the mixture was stirred for 30 minutes. The organic layer was decanted, dried over MgSO₄, filtered and evaporated, yielding 1.5 g of intermediate shown.

A1.g) Preparation of Intermediate

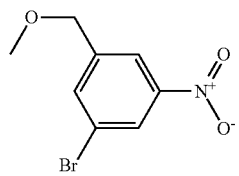

Sodium hydride (128.085 mmol) was suspended in THF (dry, 220 ml). A solution of 3-bromo-5-nitro-benzenemethanol (32.021 mmol) in THF (dry) was added dropwise at 0° C. The mixture was stirred for 15 min at 0° C. Iodomethane (76.851 mmol) was added dropwise and the mixture was stirred at room temperature for 3 hours. The mixture was poured out into ice and extracted with AcOEt. The organic layer was dried over MgSO₄, filtered and evaporated till dryness. The residue was purified by HPLC over 200 g of silica gel 15-40 μm (eluent: DCM 100%). The pure fractions were evaporated till dryness, yielding 4.23 g (54%) of intermediate shown.

A1.h) Preparation of Intermediate

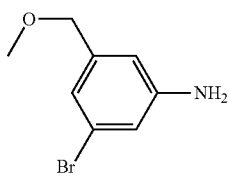

Intermediate of example A1.g (0.0165 mol) in methanol (40 ml) and THF (40 ml) with Raney nickel (0.00682 mol) as a catalyst was hydrogenated at room temperature for 30 minutes under a 1.5 bar pressure of H₂. The mixture was filtered over celite. The filtrate was evaporated till dryness. The residue (3.55 g) was purified by HPLC over 90 g of silica gel 15-40 μm (eluent: DCM/CH₃OH: 100/0 to 97/3). The pure fractions were evaporated till dryness, yielding 0.78 g (22%) of intermediate shown.

A1.i) Preparation of Intermediate

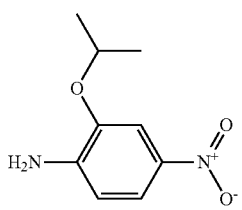

2-amino-5-nitro-phenol (5 g, 32.4 mmol), 2-bromopropane (3 ml, 32.44 mmol) and potassium carbonate (9 g, 64.9 mmol) in acetone (250 ml) were stirred at reflux for 8 hours. 2-bromopropane (1.5 ml, 16.2 mmol) was added. The reaction mixture was refluxed for 24 hours. 2-bromopropane (1.5 ml, 16.2 mmol) was added. The reaction mixture was refluxed for 24 hours. After cooling down to room temperature, the mixture was filtered over celite. Celite was washed with acetone. The filtrate was evaporated. The residue was taken up into petroleum ether. The supernatant was decanted and the oily residue was taken up into DCM and the solvent was evaporated, yielding 5.9 g of intermediate shown.

A1.j) Preparation of Intermediate

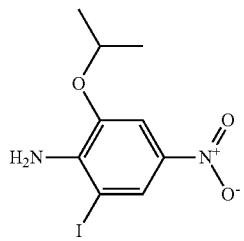

Iodine monochloride (150.352 mmol) was added portion-wise to a stirred solution of intermediate of example A1.i. (30.07 mmol) in THF at room temperature. The reaction mixture was stirred at reflux for 2 hours. After cooling down to room temperature, water, ice and $Na_2S_2O_3$ powder were added. The solvent was evaporated. The aqueous layer was extracted twice with DCM, dried over $MgSO_4$, filtered and evaporated. The residue was taken up into DIPE, filtered and evaporated. The residue (15 g) was purified by flash chromatography over silica gel (15-40 μm, 200 g, from DCM/cyclohexane: 50/50 to DCM/cyclohexane: 70/30). The pure fractions were collected and evaporated to dryness, yielding 10 g of intermediate shown.

A1.k) Preparation of Intermediate

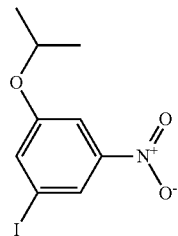

Intermediate of example A1.j (10 g, 31 mmol), sulfuric acid (2 mL) in ethanol (80 mL) were stirred 30 minutes at reflux. Sodium nitrite (5.4 g, 77.6 mmol) was added portionwise and the reaction mixture was stirred 2 hours at reflux. The reaction mixture was cooled down to room temperature. Ethanol was evaporated than water and AcOEt were added. The organic layer was washed with water and brine. The organic layer was dried over $MgSO_4$, filtered, and the solvent was evaporated. The residue was purified by flash chromatography over silica gel (15-40 μm, 90 g, from DCM/cyclohexane: 30/70 to DCM/cyclohexane: 50/50) The pure fractions were collected and evaporated to dryness, yielding 3.22 g of intermediate shown.

A1.l) Preparation of Intermediate

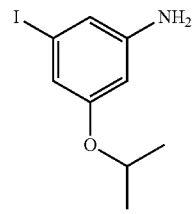

Titanium (III) chloride (78 mL, 90.854 mmol) was added dropwise to a solution of intermediate of example A1.k (3.1 g, 10.095 mmol) in THF (40 mL) at 10° C. The mixture was stirred at room temperature for 48 hours. The reaction mixture was extracted twice with DCM. The organic layer was decanted, washed with brine then with a 10% solution of potassium carbonate, dried over $MgSO_4$, filtered and evaporated to dryness, yielding 2.3 g (82%) of intermediate shown.

A1.m) Preparation of Intermediate

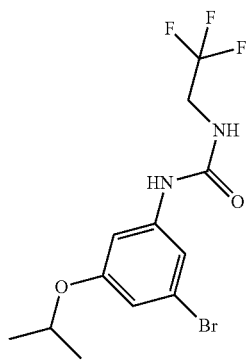 [SMILES: CC(C)Oc1cc(Br)cc(NC(=O)NCC(F)(F)F)c1]

A mixture of intermediate of example A1.b (16 g, 69.53 mmol) and 4-nitrophenyl carbonochloridic acid, ester (15.42 g, 76.49 mmol) in THF (400 ml) was heated at 60° C. for 1 hour, then allowed to cool down to room temperature. N,N-Diethylethanamine (9.68 m, 69.53 mmol) then 2,2,2-trifluoroethanamine 5% (6.11 ml, 76.49 mmol) were added dropwise at room temperature. The mixture was heated at 60° C. for 12 hours. After cooling down to room temperature, THF was evaporated. The mixture was poured out into ice/water and AcOEt was added. The organic layer was washed successively with 10% $K_2CO_3$ aqueous solution, 3N HCl aqueous solution and water. The organic layer was separated, dried ($MgSO_4$).filtered and the solvent was evaporated. The residue was taken up into diethyl ether, filtered and dried to give 11.6 g of fraction 1.

The filtrate was evaporated and taken up into $Et_2O$. The precipitate was filtered off and dried to afford 5.5 g of fraction 2.

The fraction 1 and fraction 2 were combined to give 17.1 g (69.2%) of intermediate shown.

A1.n) Preparation of Intermediate

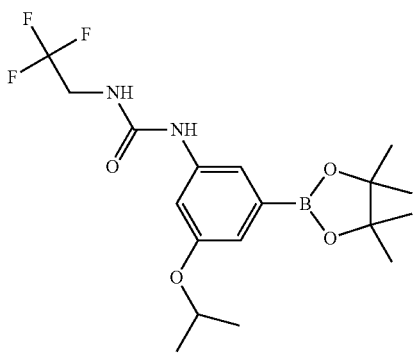 [SMILES: CC(C)Oc1cc(NC(=O)NCC(F)(F)F)cc(B2OC(C)(C)C(C)(C)O2)c1]

A mixture of intermediate of example A1.m (6.5 g, 18.30 mmol), octamethyl-2,2'-bi-1,3,2-dioxaborolane, (6.3 g, 24.7 mmol) and potassium acetate (5.39 g, 54.91 mmol) in dimethyl sulfoxide (100 ml) was stirred and degassed with $N_2$ for 15 minutes. 1,1'bis(diphenylphosphino)ferrocenedichloro palladium (401.75 mg, 0.55 mmol) was added. The mixture was heated at 100° C. for 6 hours. More 4,4,4',4',5,5,5',5'-octamethyl-2,2'-bi-1,3,2-dioxaborolane (900 mg, 3.55 mmol) was added and the mixture was stirred at 100° C. for another 4 hours.

The mixture was poured into water, AcOEt was added and the mixture was filtered through a layer of celite. The organic layer was separated, the organic layer was washed with water then brine, dried over $MgSO_4$, filtered and evaporated to dryness. The crude product was taken-up into DIPE, stirred at room temperature for one hour, the precipitated was filtered, washed with DIPE and the filtrate was evaporated to give 5.6 g (76.0%) of intermediate shown.

Example A2-1

A2-1.a) Preparation of Intermediate

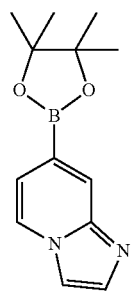 [SMILES: CC1(C)OB(c2ccn3ccnc3c2)OC1(C)C]

7-Chloro-imidazo[1,2-a]pyridine (10 g; 65.54 mmol), 4,4,4',4',5,5,5',5'-octamethyl-2,2'-bi-1,3,2-dioxaborolane (19.93 g; 78.65 mmol), $K_2CO_3$ (13.59 g; 98.31 mmol), tricyclohexylphosphine (1.84 g; 6.55 mmol), Palladium acetate (47% Pd) (0.74 g; 3.28 mmol) in 2-methoxyethylether (100 ml) and water (0.13 ml) were heated to 100° C. for 15 hours under $N_2$. The reaction mixture was cooled to room temperature. The mixture was cooled to 5° C., filtered, washed the cake with 2×10 ml of water and poured into in 50 ml of water then filtered and the insoluble was washed with 2×20 ml of water, dried to give 11.25 g (70.396) of intermediate shown.

A2-1.b) Preparation of Intermediate

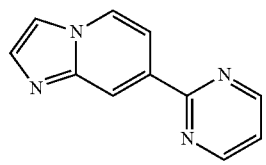 [SMILES: c1cnc(-c2ccn3ccnc3c2)nc1]

A solution of intermediate of example A2-1.a (11.2 g; 0.45.88 mmol) and 2-bromo-pyrimidine (10.95 g; 68.8 mmol) in dioxane (440 ml) was degazed under $N_2$ for 30 minutes at room temperature. $Na_2CO_3$ (229.5 ml; 458.83 mmol) and 1,1'bis(diphenylphosphino)ferrocenedichloro palladium (3.36 g; 4.59 mmol) were added and the solution was heated at 100° C. overnight. The solution was poured into cooled water, filtered on celite, the product was extracted with DCM, the organic layer was dried over $MgSO_4$ and evaporated to dryness. The residue was purified by Normal phase on (Irregular SiOH 15-40 µm 300 g MERCK). Mobile phase (0.5% $NH_4OH$, 97% DCM, 3% MeOH) to give 8.6 g (95.5%) of intermediate shown.

A2-1.c) Preparation of Intermediate

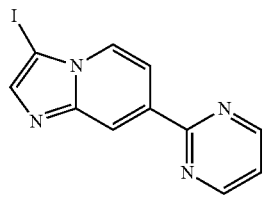 [SMILES: Ic1cnc2cc(-c3ncccn3)ccn12]

1-Iodo-2,5-pyrrolidinedione (3.94 g, 17.49 mmol) was added in one portion to a solution of intermediate of example A2-1.b (2.86 g, 14.58 mmol) in acetonitrile (80 ml). The mixture was stirred at room temperature for 1 night. The precipitate was filtered off, washed with $CH_3CN$ and dried, yielding 4.49 g (95.6%) of intermediate shown.

Example A2-2

A2-2a) Preparation of Intermediate

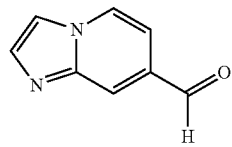 [SMILES: O=Cc1ccn2ccnc2c1]

To a suspension of imidazo[1,2-a]pyridine-7-methanol (409.815 mmol) in DCM (2 L) was added manganese oxide (819.631 mmol) under vigourous stirring. After 2 hours 2 more eq of manganese oxide (71.3 g) were added and the reaction was left overnight. 1 more eq of manganese oxide (36 g) was added and the reaction was left for 4 hours. The reaction was stopped. The reaction mixture was filtered over dicalite and the filtrate was evaporated under reduced pressure at 40° C. and dried in vacuo at 50° C. overnight, yielding 45 g of intermediate shown.

A2-2.b) Preparation of Intermediate

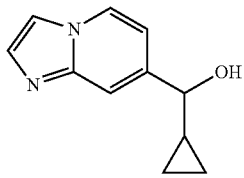 [SMILES: OC(c1ccn2ccnc2c1)C1CC1]

To a solution of intermediate of example A2-2a (27.369 mmol) in THF dry (120 ml) was added at 0° C. cyclopropylmagnesium bromide in THF 0.5 M (41.053 mmol) under nitrogen atmosphere. The reaction was stirred at 0° C. for 2 hours. Then the reaction mixture was concentrated to dryness. The residue was diluted with ethyl acetate (80 ml) and a aqueous solution of ammonium chloride (40 ml). An extraction was performed with brine (40 ml). The water layer was again extracted with AcOEt (80 ml). The organic layers were collected, dried over $Na_2SO_4$, filtered and concentrated to dryness, yielding 5.5 g of intermediate shown used crude in the next step.

A2-2.c) Preparation of Intermediate

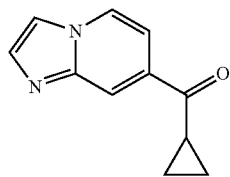 [SMILES: O=C(c1ccn2ccnc2c1)C1CC1]

To a suspension of intermediate of example A2-2.b (27.36 mmol) in DCM (132 ml) was added manganese oxide (54.721 mmol) under vigourous stirring. After 2 hours, 4 hours and 6 hours 2 eq of manganese oxide (3×4.8 g) were added and the reaction was left overnight. 2 more eq of manganese oxide (4.8 g) were added and the reaction was left for 4 hours. The reaction was stopped. The reaction mixture was filtered over dicalite and the filtrate was evaporated under reduced pressure at 40° C. and dried in vacuo at 50° C., yielding 3.7 g of intermediate shown. The product was used as such in the next reaction.

A2-2.d) Preparation of Intermediate

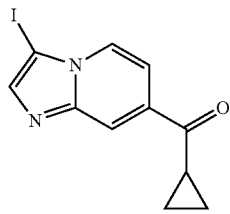 [SMILES: O=C(c1ccn2c(I)cnc2c1)C1CC1]

To a mixture of intermediate of example A2-2.c (23.057 mmol) in DMF (25 ml), 0.6 eq (3.1 g) of N-iodosuccinimide was added and the reaction mixture was stirred at room temperature for 1 hour. 0.7 eq (3.6 g) of N-iodosuccinimide was added and the reaction was left 1 hour. The reaction was stopped. The solution was slowly dropped into 200 ml of distilled water and 20 ml of a 20% solution of sodium bisulfite. After stirring for 10 minutes at room temperature, the slurry was filtered, washed with diethyl ether and the resulting solid was dried in vacuo at 50° C., yielding 3.14 g of intermediate shown.

Example A3

A3.a) Preparation of Intermediate

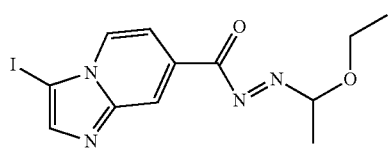 [SMILES: CCOC(C)/N=N/C(=O)c1ccn2c(I)cnc2c1]

3-Iodo-imidazo[1,2-a]pyridine-7-carboxylic acid, hydrazide (13.27 g, 43.93 mmol) and $H_2SO_4$ (0.4 ml) in 1,1,1-triethoxyethane (195 ml) were refluxed (80° C.) for 6 hours. After cooling down to room temperature, the precipitate was filtered off, washed with EtOH and dried (vacuum, 60° C., 4 h) to give 14.66 g of intermediate shown.

A3.b) Preparation of Intermediate

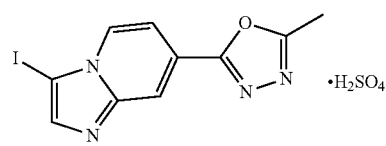

Intermediate of example A3.a (14.66 g, 39.391 mmol) and $H_2SO_4$ (430 µl) in EtOH (142 ml) were refluxed (80° C.) overnight. The reaction mixture was cooled down to room temperature. The resulting precipitate was filtered and washed with diethylether to give 10.63 g (64%) of intermediate shown.

Example A4

A4.a) Preparation of Intermediate

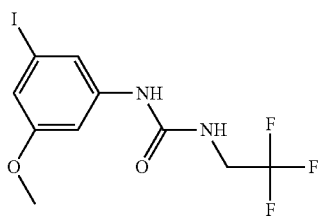 [SMILES: COc1cc(I)cc(NC(=O)NCC(F)(F)F)c1]

A mixture of 3-iodo-5-methoxybenzenamine (10 g, 40.15 mmol) and 4-nitrophenyl carbonochloridic acid, ester (8.093 g, 40.152 mmol) in THF (200 ml) was heated at 60° C. for 1 hour, then allowed to cool down to room temperature. N-Ethyl-N-(1-methylethyl)-2-propanamine (6.636 ml, 40.15 mmol) then 2,2,2-trifluoroethanamine (3.53 ml, 44.17 mmol) were added dropwise at room temperature. The mixture was heated at 60° C. for 2 hours. The mixture was poured out into ice water and AcOEt was added. The organic layer was washed successively with 10% K₂CO₃ aqueous solution, 3N HCl aqueous solution and water. The organic layer was separated, dried (MgSO₄), filtered and the solvent was evaporated to give 15 g (99.9%) of intermediate shown.

A4.b) Preparation of Intermediate

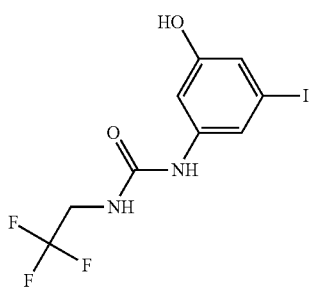 [SMILES: O=C(NCC(F)(F)F)Nc1cc(O)cc(I)c1]

Intermediate of example A4.a (3 g, 8 mmol) in methanesulfonic acid (15 ml) was stirred at 160° C. for 25 minutes. The mixture was poured out ice water and extracted twice with AcOEt. The aqueous layer was extracted again with AcOEt. The organic layers were combined, washed with water, dried over MgSO₄, filtered and evaporated. The residue was purified by Normal phase on (Irregular SiOH 15-40 μm 300 g MERCK). Mobile phase (60% HEPTANE, 40% AcOEt) to give 1.5 g (25%) of intermediate of example A4.a and 0.45 g (7.8%) of intermediate shown.

A4.c) Preparation of Intermediate

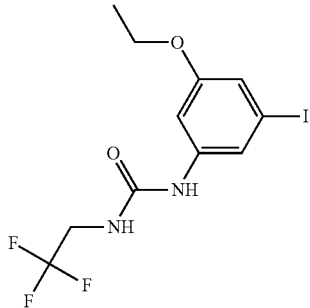 [SMILES: CCOc1cc(I)cc(NC(=O)NCC(F)(F)F)c1]

A solution of intermediate of example A4.b (683 mg, 1.90 mmol), iodoethane (167 μl, 2.09 mmol) and K₂CO₃ (288.4 mg, 2.09 mmol) in DMF (14 ml) was stirred at room temperature overnight. The reaction mixture was diluted with AcOEt. The organic layer was washed with water then brine, dried over MgSO₄, filtered and the solvent was evaporated. The residue was taken up with pentane and the supernatant (pentane) was removed. CH₂Cl₂ was added in the residue. The solvent was evaporated to give 736 mg (99.9%) of intermediate shown.

A4.d) Preparation of Intermediate

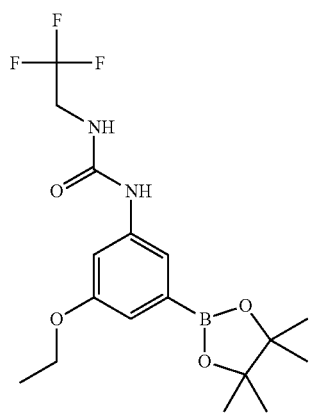 [SMILES: CCOc1cc(NC(=O)NCC(F)(F)F)cc(B2OC(C)(C)C(C)(C)O2)c1]

Intermediate of example A4.c (736 mg, 1.90 mmol), 4,4,4',4',5,5,5',5'-octamethyl-2,2'-bi-1,3,2-dioxaborolane (530 mg, 2.09 mmol) and potassium acetate (558 mg, 5.69 mmol) in dimethyl sulfoxide (4.2 ml) was stirred and degassed with N₂ for 15 minutes. 1,1'Bis(diphenylphosphino)ferrocene-dichloro palladium (42 mg, 0.057 mmol) was added. The mixture was stirred at 100° C. for 3 hours. The mixture was poured into water and filtered over a pad of celite. Celite was washed with water then extracted with Et₂O. The organic layer was washed with water, dried over MgSO₄, filtered and evaporated. The residue was taken up with pentane and the supernatant (pentane) was removed. CH₂Cl₂ was added in the residue. The solvent was evaporated to give 686 mg (93.19%) of intermediate shown.

Example A5

A5.a) Preparation of Intermediate

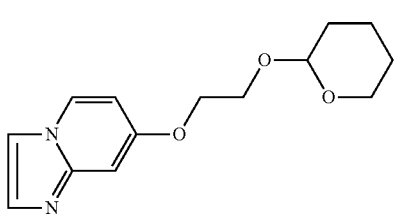 [SMILES: c1cn2ccc(OCCOC3CCCCO3)cc2n1]

Imidazo[1,2-a]pyridin-7-ol (3 g, 0.023 mol), 2-(2-bromoethoxy)tetrahydro-2H-Pyran (3.6 mL, 0.023 mol) and K₂CO₃ (6.32 g, 0.05 mol) were heated in DMF (100 ml) for 3 hours. The solution was cooled and evaporated to dryness. The residue was taken up with DCM+MeOH, the solution was filtered through a celite layer and the filtrate was evaporated to dryness. The residue was purified by Normal phase on E 5424 (Irregular SiOH 15-40 μm 300 g MERCK). Mobile phase (0.3% NH₄OH, 97% DCM, 3% MeOH), yielding 1.49 g (24.8%) of intermediate shown.

A5.b) Preparation of Intermediate

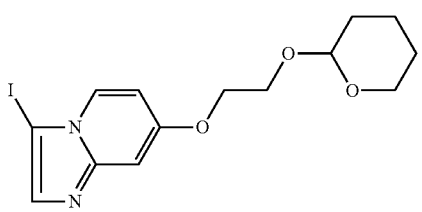 [SMILES: Ic1cnc2cc(OCCOC3CCCCO3)ccn12]

Intermediate of example A5.a (1.49 g, 5.68 mmol) and 1-iodo-2,5-pyrrolidinedione (1.53 g, 6.82 mmol) were stirred at room temperature for 1 hour in acetonitrile (50 ml). The residue was taken up with DCM, the organic layer was washed with NaHCO$_3$ saturated solution and Na$_2$S$_2$O$_3$ saturated solution, dried over MgSO$_4$ and evaporated, yielding 2.04 g (92.5%) of intermediate shown.

A5.c) Preparation of Intermediate

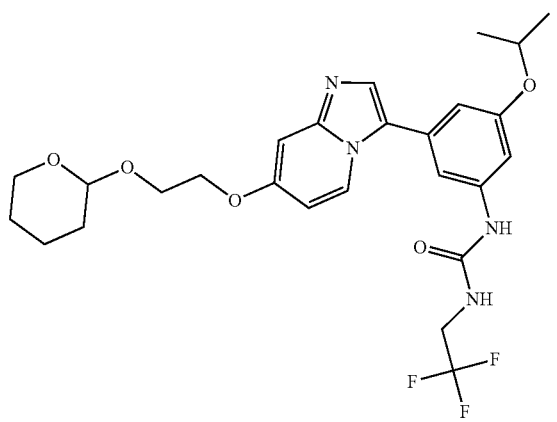 [SMILES: CC(C)Oc1cc(NC(=O)NCC(F)(F)F)cc(-c2cnc3cc(OCCOC4CCCCO4)ccn23)c1]

Potassium phosphate (0.51 g, 2.40 mmol) was added to intermediate of example A1.n (0.58 g, 1.44 mmol) and intermediate of example A5.b (0.47 g, 1.20 mmol) in dioxane (16 ml) and water (1 ml) under N$_2$ flow and was degassed for 30 minutes. After adding 1,1'bis(diphenylphosphino)ferrocenedichloro palladium (44 mg, 0.06 mmol). The reaction was heated at 80° C. for 3 hours. The mixture was poured into ice and extracted with AcOEt. The organic layer was dried over MgSO$_4$, filtered and evaporated till dryness. The residue was purified by Normal phase on (Stability Silica 5 μm 150×30.0 mm) E5525. Mobile phase (Gradient from 0.2% NH$_4$OH, 98% DCM, 2% MeOH to 1% NH$_4$OH, 90% DCM, 10% MeOH), yielding 207 mg (32%) of intermediate shown.

Example A6

A6.a) Suzuki Coupling

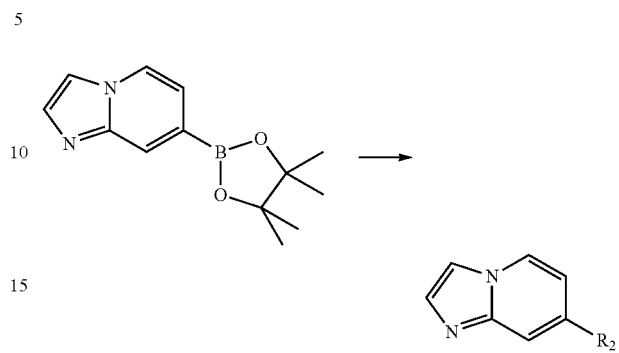

To a solution of in a mixture of toluene (3.6 ml), n-butanol (3.6 ml), water (0.9 ml), cesium carbonate (424 mg, 1.3 mmol), was added appropriate halo compound (250 mg, 1.08 mmol). The reaction mixture was deoxygenated and tetrakis (triphenylphosphine)palladium (0) (70 mg, 60 μmol) added. The reaction mixture was again degassed and heated at 80° C. for 2.5 h. The mixture was cooled, partitioned between EtOAc and H2O, the organic layer separated, dried (MgSO4), filtered and the solvent remove in vacuo. The crude product was purified by preparative HPLC to give the 20 mg of product.

A6.b) Iodination

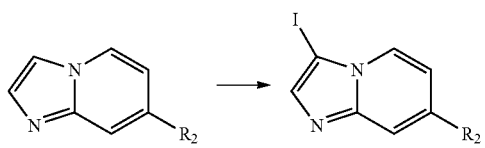

To a solution of 7-substituted-imidazo[1,2-a]pyridine prepared as described above (1.0 equiv) in DMF (280 ml) was added N-iodosuccinimide (1.05 equiv) and the resulting mixture was stirred overnight at RT. The thin brown slurry was diluted with water (840 ml), brine (280 ml) and extracted with EtOAc (560 ml). The aqueous layer was further extracted with EtOAc (3×280 ml). The combined organic phases were washed with water (2×280 ml), 10% w/v sodium thiosulfate (280 ml), brine (280 ml), dried (MgSO4), filtered and concentrated in vacuo to give a brown residue. The residue was triturated with ether (200 ml), filtered and the solid was washed with ether (2×50 ml) and dried on the filter to give iodinated product.

Example A7

A7.a) Preparation of Intermediate

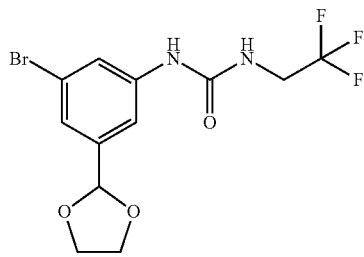 [SMILES: O=C(NCC(F)(F)F)Nc1cc(Br)cc(C2OCCO2)c1]

A solution of 2-(3-amino-5-bromophenyl)-1,3-dioxolane (CAS:936844-19-8) (5.2 g, 21.3 mmol) and 4-nitrophenyl chloroformate (4.3 g, 21.3 mmol) in THF (140 ml) was heated at 60° C. for 1 hour. Then, it was cooled to room temperature and N,N-diisopropylamine (3.5 ml, 21.3 mmol) followed by 2,2,2-trifluoroethylamine (1.87 ml, 23.4 mmol) were added dropwise. The resulting mixture was heating at 60° C. for 2 hours, then cooled down to room temperature and poured onto ice-water. The aqueous layer was extracted with EtOAc. The organic layer was washed successively with aqueous $K_2CO_3$ 10% solution, aqueous HCl 3N and water. Then, the organic layer was dried over $MgSO_4$, filtered and concentrated to afford 8.7 g (quantitative) of intermediate shown.

A7.b) Preparation of Intermediate

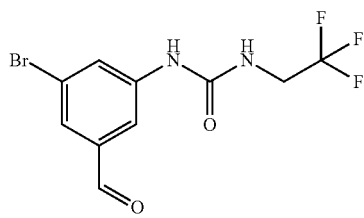 [SMILES: O=Cc1cc(Br)cc(NC(=O)NCC(F)(F)F)c1]

Intermediate of example A7.a (7.2 g, 19.5 mmol) was diluted in a mixture of THF (40 ml) and HCl 3N (20 ml). The resulting solution was stirred at room temperature overnight. The reaction mixture was carefully neutralized with $K_2CO_3$. The aqueous layer was extracted with DCM. The organic layer was washed with saturated aqueous NaCl solution, dried over $MgSO_4$ filtered and concentrated to afford 6.7 g (quantitative) of intermediate shown.

A7.c) Preparation of Intermediate

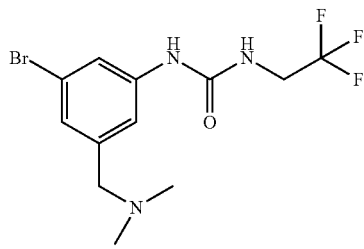 [SMILES: CN(C)Cc1cc(Br)cc(NC(=O)NCC(F)(F)F)c1]

Intermediate of example A7.b (6 g, 18.45 mmol), dimethylamine hydrochloride (3.33 g, 73.82 mmol) and triethylamine (10.3 ml, 73.83 mmol) were diluted in ethanol (30 ml). The resulting solution was stirred at 50° C. for 2 hours, then cooled down to 0° C. Sodium cyanoborohydride (2.32 g, 36.91 mmol) was added and the resulting mixture was stirred overnight allowing the temperature to rise to room temperature. The reaction mixture was then neutralized with water. Ethanol was concentrated and the aqueous layer was extracted with DCM. The organic layer was dried over $MgSO_4$, filtered and concentrated to afford a residue (8.7 g) which was purified by Normal phase on (Irregular SiOH 15-40 μm 300 g MERCK). Mobile phase (0.1% $NH_4OH$, 92% DCM, 8% MeOH). The pure fractions were collected and the solvent was evaporated, yielding 2.6 g (39%) of intermediate shown.

A7.d) Preparation of Intermediate

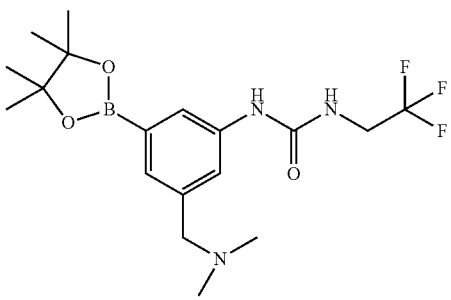 [SMILES: CN(C)Cc1cc(NC(=O)NCC(F)(F)F)cc(B2OC(C)(C)C(C)(C)O2)c1]

Intermediate of example A7.c (2.5 g, 7.06 mmol), 4,4,4',4',5,5,5',5'-octamethyl-2,2'-bi-1,3,2-dioxaborolane (1.97 g, 7.7 mmol) and potassium acetate (2.08 g, 21.17 mmol) were diluted in ethyleneglycol dimethylether (10 ml). The resulting mixture was stirred and degassed with $N_2$ for 15 minutes. Then, 1,1'bis(diphenylphosphino)ferrocenedichloro palladium (155 mg, 0.21 mmol) was added and the mixture was stirred at 100° C. for 2 hours. The reaction mixture was cooled down to room temperature, poured onto ice water. The aqueous layer was extracted with AcOEt. The organic layer was dried over $MgSO_4$, filtered and concentrated to afford a residue (3.6 g) which was precipitated with pentane to afford after filtration 3.1 g (99%) of intermediate shown.

Example A8

A8.a) Preparation of Intermediate

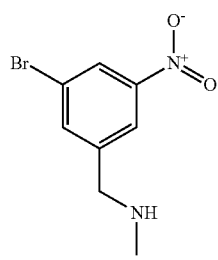

1-bromo-3-(bromomethyl)-5-nitrobenzene (5 g, 16.9 mmol) and methylamine 2M in THF (33.9 ml, 67.8 mmol) were diluted in THF (30 ml) and the solution was stirred overnight at room temperature. The reaction mixture was partitioned between DCM and water. The organic layer was separated, dried over $MgSO_4$, filtered and concentrated to afford 4.6 g (quantitative) of intermediate shown.

A8.b) Preparation of Intermediate

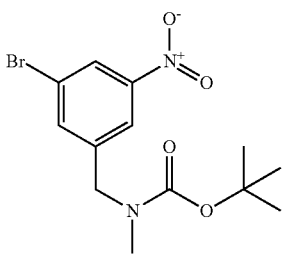 [SMILES: CN(Cc1cc(Br)cc([N+](=O)[O-])c1)C(=O)OC(C)(C)C]

Intermediate of example A8.a (4.6 g, 18.77 mmol) and di-tertbutyldicarbonate (4.09 g, 18.77 mmol) were diluted in DCM (15 ml). The resulting solution was stirred at room temperature for 4 hours, then, hydrolyzed with water. The aqueous layer was extracted with DCM. The organic layer was dried with $MgSO_4$, filtered and concentrated yielding 6.6 g (quantitative) of intermediate shown.

A8.c) Preparation of Intermediate

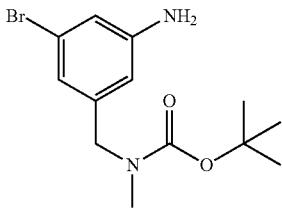 [SMILES: CN(Cc1cc(N)cc(Br)c1)C(=O)OC(C)(C)C]

Iron (10.67 g, 191.2 mmol) and iron (II) sulphate pentahydrate (11.62 g, 76.48 mmol) were added to a solution of intermediate of example A8.b (6.6 g, 19.12 mmol) previously solubilised in a mixture of dioxane (66 ml) and water (13 ml). The resulting mixture was refluxed for 3 hours, cooled down to room temperature, filtered through a pad of celite. The filtrate was concentrated and the resulting residue was partitioned between DCM and brine. The organic layer was separated, filtered through a pad of celite, dried over $MgSO_4$ and concentrated to afford a residue (7 g). The residue was purified by Normal phase on (Irregular SiOH 15-40 µm 300 g MERCK). Mobile phase (gradient from 0% $NH_4OH$, 99% DCM, 1% MeOH to 0.1% $NH_4OH$, 97% DCM, 3% MeOH). The pure fractions were collected and the solvent was evaporated, yielding 3.96 g (65%) of intermediate shown.

A8.d) Preparation of Intermediate

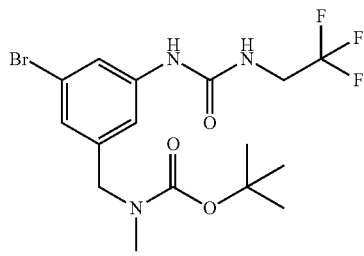 [SMILES: CN(Cc1cc(Br)cc(NC(=O)NCC(F)(F)F)c1)C(=O)OC(C)(C)C]

A solution of intermediate of example A8.c (3.69 g, 11.24 mmol) and 4-nitrophenyl chloroformate (2.49 g, 12.36 mmol) in THF (60 ml) was heated at 60° C. for 1 hour. Then, it was cooled to room temperature and triethylamine (1.56 ml, 11.24 mmol) followed by 2,2,2-trifluoroethylamine (0.99 ml, 12.36 mmol) were added dropwise. The resulting mixture was heating at 60° C. for 2 hours, then cooled down to room temperature. The solvent was concentrated and the mixture was poured onto ice-water. The aqueous layer was extracted with EtOAc. The organic layer was washed successively with aqueous $K_2CO_3$ 10% solution, aqueous HCl 3N and water. Then, the organic layer was separated, dried over $MgSO_4$, filtered and concentrated to afford a residue (5.6 g) which was purified by Normal phase on (Irregular SiOH 15-40 µm 300 g). Mobile phase (gradient from 80% heptane, 20% AcOEt to 60% heptane, 40% AcOEt). The pure fractions were collected and the solvent was evaporated, yielding 2.95 g (59%) of intermediate shown.

A8.e) Preparation of Intermediate

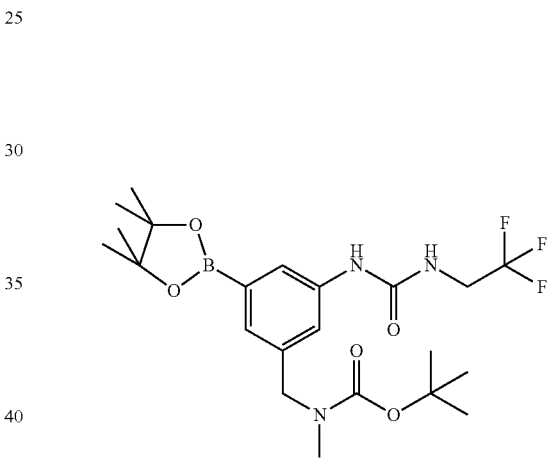

Intermediate of example A8.d (2.7 g, 6.13 mmol), 4,4,4', 4',5,5,5',5'-octamethyl-2,2'-bi-1,3,2-dioxaborolane (4.67 g, 18.4 mmol), potassium acetate (2.65 g, 26.98 mmol) and tricyclohexylphosphine (860 mg, 3.06 mmol) were diluted in dioxane (50 ml). The resulting mixture was stirred and degassed with $N_2$ for 15 minutes. Then, tris(dibenzylideneacetone) dipalladium (0) (842.4 mg, 0.92 mmol) was added and the mixture was stirred at 100° C. for 1 hour. The reaction mixture was cooled down to room temperature and water was added. Then, the dioxane was concentrated and DCM was added. The resulting mixture was filtrated over a pad of celite. The organic layer was separated, washed with water (twice), dried over $MgSO_4$ filtered and concentrated yielding the intermediate shown which was directly used in the next step without any further purification.

A8.f) Preparation of Intermediate

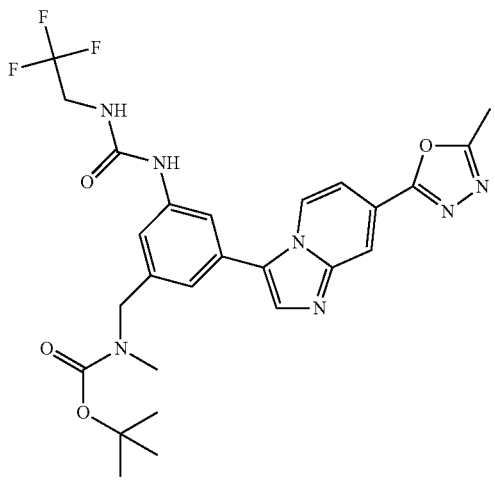 [SMILES: Cc1nnc(-c2ccn3c(-c4cc(CN(C)C(=O)OC(C)(C)C)cc(NC(=O)NCC(F)(F)F)c4)cnc3c2)o1]

Intermediate of example A3.b as free base (600 mg, 1.84 mmol), intermediate of example A8.e (986.3 mg, 2.02 mmol) and potassium phosphate (859 mg, 4.05 mmol) were diluted in dioxane (6.6 ml) and water (1.7 ml). The resulting mixture was stirred at room temperature and degassed with $N_2$ for 10 minutes. Then, 1,1'bis(diphenylphosphino)ferrocenedichloro palladium (134.6 mg, 0.184 mmol) was added and the mixture was stirred at 65° C. for 5 hours. The reaction mixture was cooled down to room temperature and filtrated over a pad of celite which was washed with DCM. The organic layer was then separated, dried over $MgSO_4$, filtered and concentrated to afford a residue (1.2 g) which was purified by Normal phase on (Irregular SiOH 15-40 μm 300 g Merck). Mobile phase (0.5% $NH_4OH$, 94% DCM, 6% MeOH). The pure fractions were collected and the solvent was evaporated, yielding 410 mg (40%) of intermediate shown.

Example A9

A9.a) Preparation of the Mixture of Intermediates

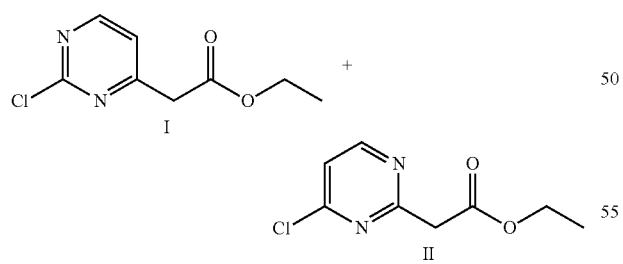

At a temperature between 0 and 5° C., sodium hydride (4.9 g, 122 mmol) was added portionwise to ethylacetoacetate (12.7 ml, 101 mmol) in solution in THF (350 ml). The reaction mixture was stirred allowing the temperature to rise to room temperature. Then, 2,4-dichloropyrimidine (10 g, 67.12 mmol) was added portionwise and the reaction was stirred overnight at 60° C. After cooling to room temperature, the reaction mixture was poured onto ice-water. The aqueous layer was extracted twice with AcOEt. The organic layer was dried over $MgSO_4$, filtered and concentrated to afford a residue (21 g) which was purified by Normal phase on (Irregular SiOH 20-45 μm 1000 g MATREX). Mobile phase (80% cyclohexane, 20% AcOEt). The pure fractions were collected and the solvent was evaporated, yielding 4.7 g (35%) of the mixture of intermediates shown (ratio I/II==85/15).

A9.b) Preparation of Intermediate

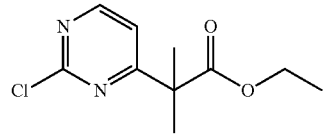

At −20° C., sodium hydride (2.34 g, 58.6 mmol) was added portionwise to a solution of the mixture of intermediates of example A9.a (4.7 g, 23.43 mmol) and iodomethane (4.37 ml, 70.28 mmol) in THF (60 ml). The reaction mixture was stirred 1 hour allowing the temperature to rise to room temperature. Then, it was poured onto ice water and the aqueous layer was extracted twice with $Et_2O$. The organic layer was dried over $MgSO_4$, filtered and concentrated to afford a residue (4.35 g) which was purified by Normal phase on (Irregular SiOH 20-45 μm 450 g MATREX). Mobile phase (gradient from 90% cyclohexane, 10% AcOEt to 70% cyclohexane, 30% AcOEt). The pure fractions were collected and the solvent was evaporated, yielding 2.26 g (42%) of intermediate shown.

The regio-isomer

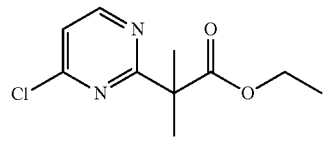

was also obtained by this procedure.

Example A10

A10.a) Preparation of Intermediate

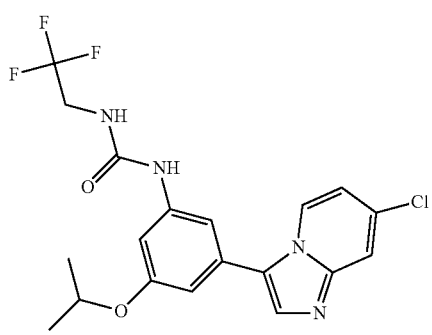 [SMILES: CC(C)Oc1cc(NC(=O)NCC(F)(F)F)cc(-c2cnc3cc(Cl)ccn23)c1]

7-chloroimidazo[1,2-a]pyridine (CAS:4532-25-6) (837.7 mg, 5.5 mmol), intermediate of example A1.m (1.5 g, 4.22 mmol), triphenylphosphine (132 mg, 0.5 mmol), cesium carbonate (1.63 g, 5 mmol) and palladium (II) acetate (56.1 mg, 0.25 mmol) were solubilised in dry DMF. The mixture was degassed 5 times using vacuum/nitrogen cycle. Then, it was heated at 100° C. for 2 hours. Additional 7-chloroimidazo[1,2-a]pyridine (194 mg, 1.27 mmol) was added and the reaction was heated at 100° C. for another hour. The reaction mixture was poured onto ice-water. The aqueous layer was extracted with AcOEt. The organic layer was filtered through a pad of celite, then washed twice with saturated aqueous NaCl solution and water, dried over MgSO$_4$, filtered and concentrated to afford a residue (2.55 g) which was purified by Normal phase on (Irregular SiOH 20-45 µm 450 g MATREX). Mobile phase (0.5% NH$_4$OH, 95% DCM, 5% MeOH). The pure fractions were collected and the solvent was evaporated, yielding 545 mg (30%) of intermediate shown (MP=231° C., köfler).

A10.b) Preparation of Intermediate

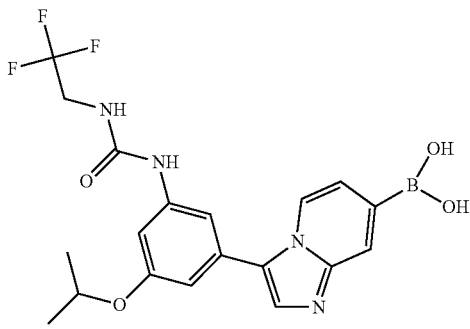 [SMILES: CC(C)Oc1cc(NC(=O)NCC(F)(F)F)cc(-c2cnc3cc(B(O)O)ccn23)c1]

Intermediate of example A10.a (4.81 g, 11.27 mmol), 4,4,4',4',5,5,5',5'-octamethyl-2,2'-bi-1,3,2-dioxaborolane (9.16 g, 36.062 mmol), potassium acetate (4.86 g, 49.58 mmol) and tricyclohexylphosphine (1.52 g, 5.41 mmol) were diluted in dioxane (64 ml). The resulting mixture was stirred and degassed with N$_2$ for 10 minutes. Then, tris(dibenzylideneacetone) dipalladium (0) (1.55 g, 1.69 mmol) was added and the mixture was refluxed overnight. The reaction mixture was cooled down to room temperature. Water and AcOEt were added and the resulting mixture was filtered over a pad of celite. The aqueous layer was extracted twice with AcOEt. The organic layers were combined, washed with saturated aqueous NaCl solution, dried over MgSO$_4$, filtered and concentrated. The crude residue was solubilised at 60° C. in toluene (80 ml). Then pentane (200 ml) was added dropwise and the mixture was allowed to stir overnight at room temperature. Filtration of the precipitate yielded 4.34 g (88%) of intermediate shown.

Example A11

A11.a) Preparation of Intermediate

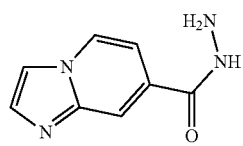 [SMILES: NNC(=O)c1ccn2ccnc2c1]

Hydrazine monohydrate (10 ml, 636 mmol) was added to methyl imidazo[1,2-a]pyridine-7-carboxylate (CAS: 86718-01-6) (11.2 g, 63.57 mmol) in solution in MeOH (300 ml). The reaction mixture was refluxed for 3 hours, then additional hydrazine monohydrate (10 ml, 636 mmol) was added and the mixture was refluxed overnight. After cooling to room temperature, the precipitate was filtered, washed with EtOH and dried yielding 13 g (quantitative) of intermediate shown.

A11.b) Preparation of Intermediate

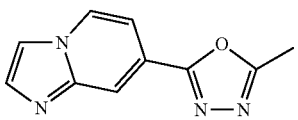

Intermediate of example A11.a (7.2 g, 40.86 mmol) and concentrated sulphuric acid (0.23 ml) were diluted in triethyl orthoacetate (202.3 ml). The reaction mixture was heated at 80° C. overnight, then cooled down to room temperature. The precipitate was filtered and solubilised with DCM. The organic layer was washed with water, dried over MgSO$_4$, filtered and concentrated yielding 7.2 g (88%) of intermediate shown.

A11.c) Preparation of Intermediate

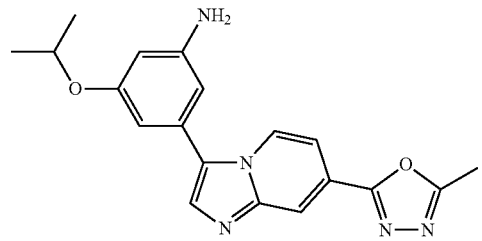 [SMILES: Cc1nnc(-c2ccn3c(-c4cc(N)cc(OC(C)C)c4)cnc3c2)o1]

Intermediate of example A11.b (2 g, 8.19 mmol), intermediate of example A1.b (1.89 g, 8.19 mmol), triphenylphosphine (4297 mg, 1.64 mmol), cesium carbonate (10.67 g, 19.38 mmol) and palladium (II) acetate (184 mg, 0.819 mmol) were solubilised in dry DMSO (18.7 ml). The mixture was degassed 5 times using vacuum/nitrogen cycle. Then, it was heated at 100° C. for 2 hours.

The procedure above was repeated another time on the same quantity of intermediate of example A11.b Both of the reaction mixtures were cooled down to room temperature, mixed and poured onto ice-water. AcOEt was added and the mixture was filtered through a pad of celite. The aqueous layer was extracted with AcOEt. The organic layer was separated, dried over MgSO$_4$, filtered and concentrated to afford a residue (9 g) which was purified by Normal phase on (Irregular SiOH 20-45 µm 450 g MATREX). Mobile phase (0.5% NH$_4$OH, 95% DCM, 5% MeOH). The pure fractions were collected and the solvent was evaporated, yielding 5.55 g of an intermediate compound which was taken up with acetonitrile. The precipitate was filtered yielding 1.85 g (25%, 80% of purity based on $^1$H NMR) of intermediate shown.

Example A12

A12.a) Preparation of Intermediate

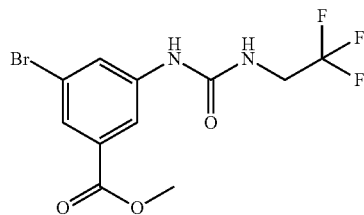 [SMILES: COC(=O)c1cc(Br)cc(NC(=O)NCC(F)(F)F)c1]

A solution of methyl-3-amino-5-bromobenzoate (CAS: 706791-83-5) (10.9 g, 47.4 mmol) and 4-nitrophenyl chloroformate (9.55 g, 47.4 mmol) in THF (300 ml) was heated at 60° C. for 1 hour. Then, it was cooled to room temperature and N,N-diisopropylamine (7.83 ml, 47.4 mmol) followed by 2,2,2-trifluoroethylamine (4.16 ml, 47.4 mmol) were added dropwise. The resulting mixture was heating at 60° C. for 2 hours, then cooled down to room temperature and poured onto ice-water. The aqueous layer was extracted with EtOAc. The organic layer was washed successively with aqueous $K_2CO_3$ 10% solution, aqueous HCl 3N and water. Then, the organic layer was dried over $MgSO_4$, filtered and concentrated to afford 17 g (quantitative) of intermediate shown.

A12.b) Preparation of Intermediate

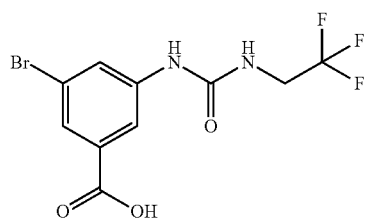 [SMILES: O=C(NCC(F)(F)F)Nc1cc(Br)cc(C(=O)O)c1]

A solution of intermediate of example A12.a (5.6 g, 15.77 mmol) in sodium hydroxide 3N (15.8 ml, 47.3 mmol) and EtOH (35 ml) was stirred at 60° C. overnight. After cooling to room temperature, water followed by HCl 3N were added until reaching acidic pH. The precipitate was filtered, washed with water and dried yielding 5.07 g (94%) of intermediate shown.

A12.c) Preparation of Intermediate

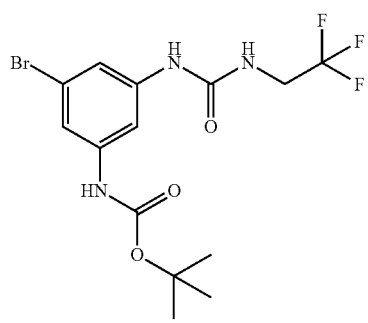 [SMILES: CC(C)(C)OC(=O)Nc1cc(Br)cc(NC(=O)NCC(F)(F)F)c1]

At room temperature, diphenylphosphoryl azide (3.36 ml, 15.6 mmol) was added to a solution of intermediate of example A12.b (5.07 g, 14.86 mmol) and triethylamine (2.48 ml, 17.83 mmol) in 2-methyl-2-propanol (90 ml). The mixture was refluxed for 24 hours and, then cooled down to 0° C. 2-methyl-2-propanol was evaporated and AcOEt was added. The organic layer was washed twice with a cold solution of 2N NaOH, then, dried over $MgSO_4$, filtered and concentrated yielding 6.4 g (quantitative) of intermediate shown.

A12.d) Preparation of Intermediate

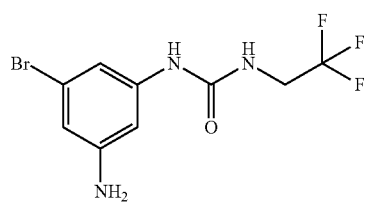 [SMILES: Nc1cc(Br)cc(NC(=O)NCC(F)(F)F)c1]

A solution of intermediate of example A12.c (6.4 g, 15.5 mmol) and trifluoroacetic acid (9.57 ml, 12421 mmol) in DCM (70 ml) was stirred at room temperature for 48 hours. The solvents were removed under vacuum. AcOEt and 10% aqueous $K_2CO_3$ solution were added to the crude residue and the resulting mixture was stirred for 30 minutes at room temperature. The organic layer was separated, dried over $MgSO_4$, filtered and concentrated to afford a residue (12.6 g) which was purified by Normal phase on (Irregular SiOH 15-40 μm 200 g). Mobile phase (gradient from 0.1% $NH_4OH$, 98% DCM, 2% MeOH to 0.1% $NH_4OH$, 90% DCM, 10% MeOH). The pure fractions were collected and the solvent was evaporated, yielding 3.8 g (78%) of intermediate shown.

A12.e) Preparation of Intermediate

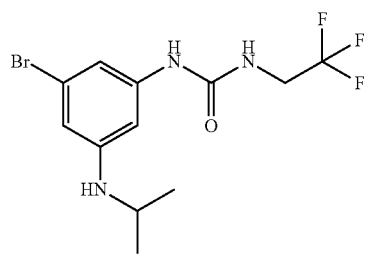 [SMILES: CC(C)Nc1cc(Br)cc(NC(=O)NCC(F)(F)F)c1]

Sodium cyanoborohydride (4.47 g, 71.13 mmol) was added to a solution of intermediate of example A12.d (3.7 g, 11.9 mmol), acetone (17.43 ml, 237.11 mmol) and acetic acid (2.71 ml, 47.4 mmol) in acetonitrile (40 ml). The reaction mixture was stirred at room temperature for 48 hours. Then, saturated aqueous $NaHCO_3$ solution was added. The aqueous layer was extracted twice with AcOEt. The organic layers were combined, washed with saturated aqueous NaCl solution, dried over $MgSO_4$, filtered and concentrated. The crude residue (6.6 g) was purified by Normal phase on (Irregular SiOH 15-40 μm 90 g). Mobile phase (gradient from 0% $NH_4OH$, 100% DCM, 0% MeOH to 0.1% $NH_4OH$, 95% DCM, 5% MeOH). The pure fractions were collected and the solvent was evaporated, yielding 2.4 g (57%) of intermediate shown.

A12.f) Preparation of Intermediate

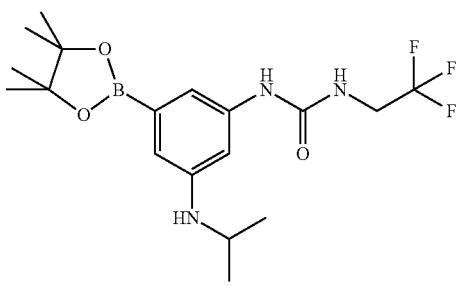 [SMILES: CC(C)Nc1cc(NC(=O)NCC(F)(F)F)cc(B2OC(C)(C)C(C)(C)O2)c1]

Intermediate of example A12.e (1 g, 2.8 mmol), 4,4,4',4', 5,5,5',5'-octamethyl-2,2'-bi-1,3,2-dioxaborolane (1.4 g, 5.6 mmol) and potassium acetate (831 mg, 8.5 mmol) were diluted in ethyleneglycol dimethylether (7 ml). The resulting mixture was stirred and degassed with $N_2$ for 15 minutes. Then, 1,1'bis(diphenylphosphino)ferrocenedichloro palladium (62 mg, 0.08 mmol) was added and the mixture was stirred at 100° C. for 4 hours. The reaction mixture was cooled down to room temperature, poured onto ice water. The aqueous layer was extracted twice with AcOEt. The organic layers were combined, dried over $MgSO_4$, filtered and concentrated to afford a residue (2 g) which was crystallized with an acetonitrile/DIPE mixture yielding after filtration 0.726 g (64%) of intermediate shown.

Example A13

A13.a) Preparation of a Mixture of Intermediates

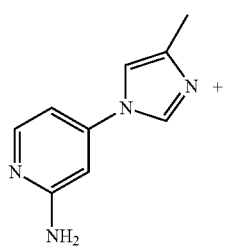   I

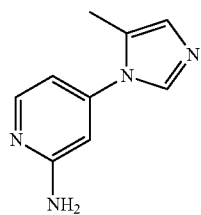   II

A mixture of 2-amino-4-chloropyridine (CAS: 19798-80-2) (2 g, 15.5 mmol) and 4-methylimidazole (CAS: 822-36-6) (2.56 g, 31.11 mmol) was heated for 30 minutes at 190° C. in a microwave biotage device. Then, the reaction mixture was cooled down, partitioned between water and DCM. The layers were separated and the aqueous layer was extracted twice with DCM. The organic layers were mixed, dried over $MgSO_4$, filtered and concentrated yielding 1.75 g (65%) of the mixture of intermediates shown (I/II: 8/2 based on the $^1$H NMR).

A13.6) Preparation of a Mixture of Intermediates

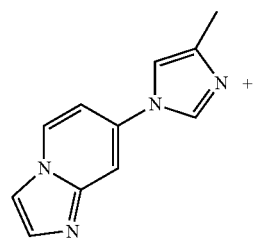   I

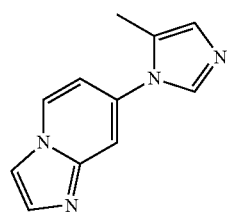   II

A mixture of intermediate of example 13.a (1.75 g, 10.05 mmol) and sodium hydrogenocarbonate (1.69 g, 20.09 mmol) in ethanol (14 ml) was heated at 60° C. Then, chloroacetaldehyde, 50% wt solution in water (1.94 ml, 15.07 mmol) was added dropwise and the resulting mixture was heated at 80° C. for 1 hour. Then, it was cooled down to room temperature and the solvent was evaporated. The residue was poured onto a mixture of water and HCl 3N and the aqueous layer was extracted with AcOEt. The aqueous layer was basified with $K_2CO_3$ and extracted again with AcOEt. The organic layers were combined, dried over $MgSO_4$, filtered and concentrated. The experimental procedure above was repeated one time on 3.04 g of intermediate of example 13.a The crude material from each reaction were mixed. The residue (3.39 g) was purified by Normal phase on (Irregular SiOH 20-45 μm 90 g). Mobile phase (gradient from 0.1% $NH_4OH$, 98% DCM, 2% MeOH to 0.1% $NH_4OH$, 95% DCM, 5% MeOH). The pure fractions were collected and the solvent was evaporated, yielding 1.87 g (57%) of the mixture of intermediates shown (I/II: 8/2 based on the $^1$H NMR).

A13.c) Preparation of a Mixture of Intermediates

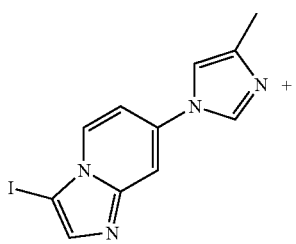   I

-continued

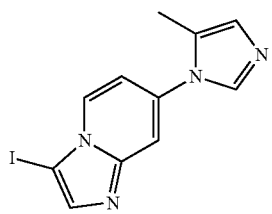

II

At room temperature, N-iodosuccinimide (681 mg, 3.03 mmol) was added to a solution of the mixture of intermediates of example A13.b (500 mg, 2.52 mmol) in DMF (4 ml). The reaction mixture was stirred for 1.5 hour at room temperature. Then, it was poured onto ice-water and stirred for 30 minutes. The precipitate was filtered, washed with Et₂O and dried to afford 790 mg (96%) of the mixture of intermediates shown.

B. Preparation of the Final Compounds

Example B1

Preparation of Compound

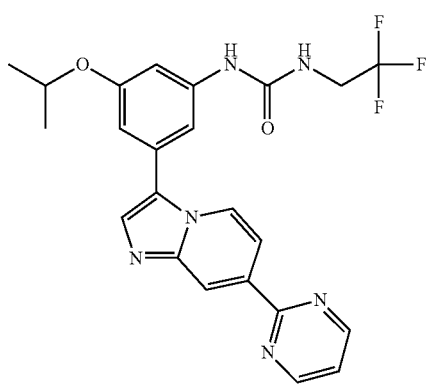 [SMILES: CC(C)Oc1cc(NC(=O)NCC(F)(F)F)cc(-c2cnc3cc(-c4ncccn4)ccn23)c1]

A mixture of intermediate of example A2-1.c (2.05 g, 6.364 mmol), intermediate A1.n (3.84 g, 9.547 mmol), potassium phosphate (2.97 g, 14.002 mmol) in dioxane (32 ml) and water (16 ml) was stirred at room temperature under N₂ flow. After 10 minutes, 1,1'bis(diphenyllphosphino)ferrocene-dichloro palladium (465 mg, 0.636 mmol) was added at room temperature under N₂ flow. The reaction mixture was heated at 90° C. for 3.30 hours. The reaction mixture was cooled to room temperature and poured out into ice water. CH₂Cl₂ was added. The mixture was filtered over celite. The organic layer was washed twice with water, dried over MgSO₄, filtered and evaporated. The residue was purified by Normal phase on (Irregular SiOH 20-45 µm 450 g MATREX). Mobile phase (Gradient from 0.2% NH₄OH, 93% DCM, 7% MeOH to 0.5% NH₄OH, 95% DCM, 5% MeOH). The residue was taken up from acetone, the residue was filtered and dried (vacuum, 40° C., 5 h) to give 3.55 g (29.6%) of compound shown.

Example B2a

Preparation of Compound

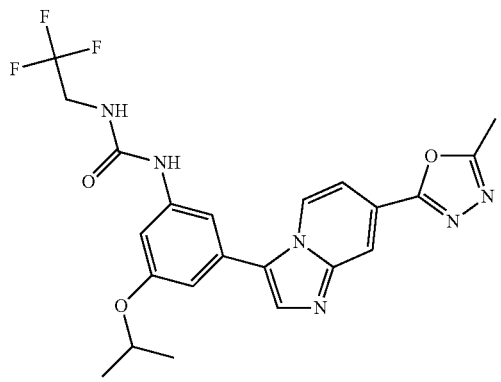 [SMILES: Cc1nnc(-c2ccn3c(-c4cc(NC(=O)NCC(F)(F)F)cc(OC(C)C)c4)cnc3c2)o1]

A mixture of intermediate of example A3.b-free base (9.7 g, 29.74 mmol), intermediate A1.n (13.16 g, 32.72 mmol) and potassium phosphate (13.89 g, 65.44 mmol) in dioxane (200 ml) and water (96 ml) was degassed at room temperature for 10 minutes then 1,1'bis(diphenyllphosphino)ferrocene-dichloro palladium (2.18 g, 2.98 mmol) was added. The reaction mixture was heated at 90° C. for 3.30 hours. The reaction mixture was cooled to room temperature, diluted with AcOEt and quenched with cold water. The suspension was filtered over a pad of celite. The organic layer was decanted, dried over MgSO₄, filtered and evaporated to dryness. The residue was purified by HPLC and Normal phase on (Irregular SiOH 20-45 µm 450 g MATREX). Mobile phase (0.5% NH₄OH, 96% DCM, 4% MeOH). The pure fractions were collected and evaporated to dryness yielding 8.2 g (58%) of compound shown.

Example B2b

B2b.1) Preparation of Compound

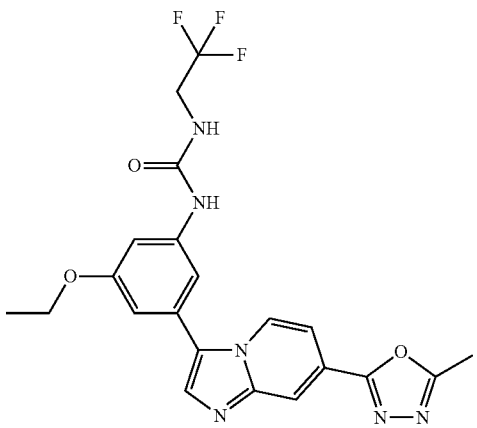 [SMILES: CCOc1cc(NC(=O)NCC(F)(F)F)cc(-c2cnc3cc(-c4nnc(C)o4)ccn23)c1]

A mixture of intermediate of example A4.d (345 mg, 0.889 mmol) and intermediate of example A3.b (435 mg, 1.333 mmol) in Na₂CO₃ 2M (3 ml) and 1,2-dimethoxyethane (9 ml) was degassed by bubbling nitrogen through for 20 minutes. Tetrakis(triphenylphosphine) palladium (51.4 mg, 0.0444 mmol) was added and the mixture was heated at 80° C. for 1 night. AcOEt and water were added. The mixture was filtered over celite. The aqueous layer was extracted with AcOEt. The organic layer was washed with brine, dried, filtered and evaporated. The residue was purified by Normal phase on (Irregular SiOH 15-40 μm 300 g MERCK). Mobile phase (Gradient from 0.2% NH$_4$OH, 98% DCM, 2% MeOH to 0.9% NH$_4$OH, 91% DCM, 9% MeOH), yielding 80 mg (19.6%) of compound shown.

B2b.2) Preparation of Compound

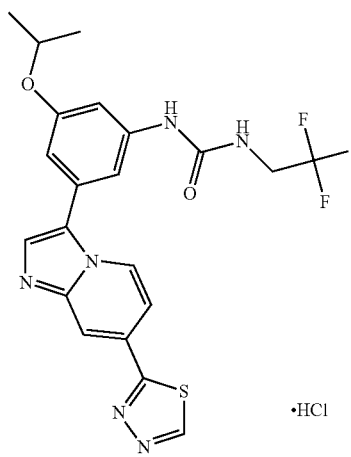

·HCl

To a solution of 1-[3-isopropoxy-5-(4,4,5,5-tetramethyl-[1,3,2]dioxaborolan-2-yl)-phenyl]-3-(2,2,2-trifluoro-ethyl)-urea (265 mg, 0.66 mmol, 1.1 equiv) and 3-iodo-7-[1,3,4]thiadiazol-2-yl-imidazo[1,2-a]pyridine (prepared according to Example A6; 197 mg, 0.60 mmol, 1.0 equiv) in DME (1,2-dimethoxyethane) (3 ml) and 2M Na$_2$CO$_3$ (3 ml) was added tetrakistriphenylphosphine palladium (0) (30 mg, 5 mol %) under an inert atmosphere. The reaction mixture was heated to 80° C. overnight. The solvents were removed and the crude mixture was partitioned between AcOEt and water. The organic layer was separated, washed with brine, dried (MgSO$_4$) and concentrated under reduced pressure. The crude material was purified by preparatory HPLC. The salt was prepared by dissolution in MeOH and DCM and saturated HCl in AcOEt was added. The solvents were removed to afford 127 mg of compound shown.

Example B3

Preparation of Compound

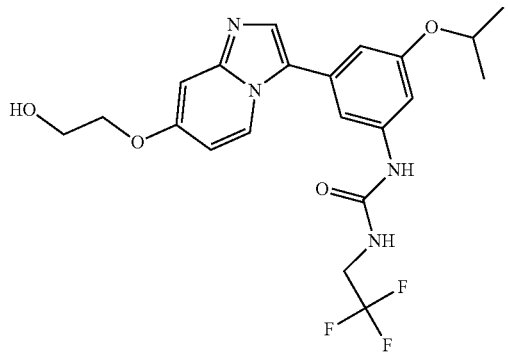 [SMILES: CC(C)Oc1cc(NC(=O)NCC(F)(F)F)cc(-c2cnc3cc(OCCO)ccn23)c1]

TFA (0.5 ml) was added dropwise to a solution of Intermediate of example A5.c (0.207 g, 0.39 mmol) in DCM (5 ml). The mixture was stirred 24 hours. DCM and K$_2$CO$_3$ 10% were added to the solution. The organic layer was extracted, washed several times with K$_2$CO$_3$ 10%, dried over MgSO$_4$ and evaporated to dryness. The residue was crystallized from acetonitrile and Et$_2$O, yielding 98 mg (56%) of compound shown.

Table F lists compounds that were prepared according to reaction protocols of one of the above Examples using alternative starting materials as appropriate.

Example B4

Preparation of Compound

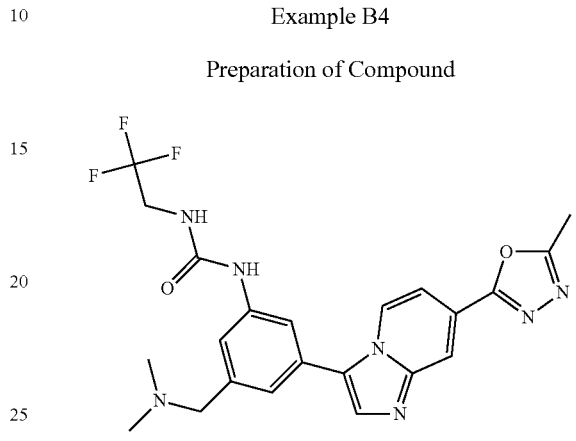

A mixture of intermediate of example A3.b as free base (0.96 g, 2.94 mmol), intermediate of example A7.d (1.3 g, 3.24 mmol), potassium phosphate (1.37 g, 6.48 mmol) in dioxane (28 ml) and water (7 ml) was stirred at room temperature under N$_2$ flow. After 10 minutes, 1,1'bis(diphenyllphosphino)ferrocenedichloropalladium (11) (215.5 mg, 0.295 mmol) was added at room temperature under N$_2$ flow. The reaction mixture was heated at 65° C. overnight. The reaction mixture was cooled to room temperature and filtered through a pad of celite which was rinsed with DCM. The organic layer was washed with saturated aqueous NaCl solution, dried over MgSO$_4$, filtered and concentrated. The residue (1.25 g) was purified by Normal phase on (Irregular SiOH 15-40 μm 300 g MERCK). Mobile phase (0.5% NH$_4$OH, 93% DCM, 7% MeOH). The pure fractions were collected and the solvent was evaporated to afford an intermediate compound which was crystallized from acetonitrile. The precipitate was filtered, yielding 307 mg (22%) of compound shown (MP=208° C., DSC). F-24

Example B5

Preparation of Compound

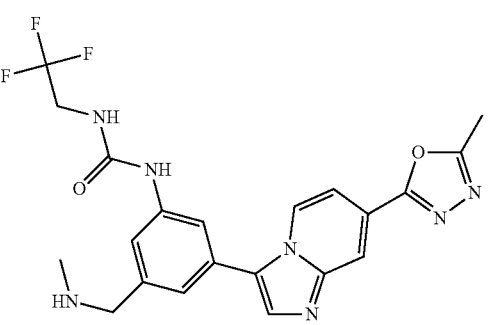 [SMILES: CNCc1cc(NC(=O)NCC(F)(F)F)cc(-c2cnc3cc(-c4nnc(C)o4)ccn23)c1]

At room temperature, trifluoroacetic acid (1.015 ml, 13.18 mmol) was added to a solution of intermediate of example A8.f (300 mg, 0.536 mmol) in DCM (4 ml). The resulting solution was stirred overnight at room temperature. The reaction mixture was neutralized with saturated aqueous NaHCO$_3$ solution. The aqueous layer was extracted with DCM. The organic layer was dried over MgSO$_4$, filtered and concentrated. The crude residue was purified by Normal phase on (Irregular SiOH 15-40 μm 300 g MERCK). Mobile phase (gradient from 1% NH$_4$OH, 87% DCM, 13% MeOH to 1% NH$_4$OH, 85% DCM, 15% MeOH). The pure fractions were collected and the solvent was evaporated, yielding 98 mg (40%) of compound shown (MP=186° C., DSC). F-25

Example B6

Preparation of Compound

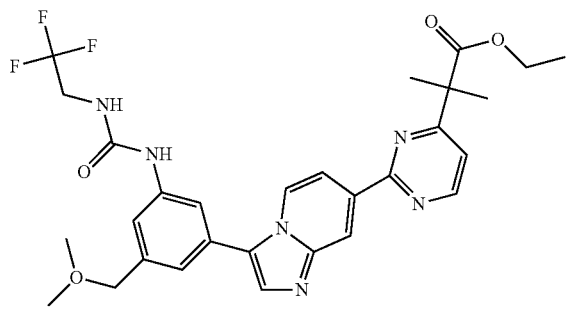

A mixture of intermediate of example A9.b (655 mg, 2.86 mmol), intermediate of example A10.b (1.5 g, 3.44 mmol), potassium phosphate (1.21 g, 573 mmol) in dioxane (66 ml) and water (15 ml) was degassed 3 times using the cycle vacuum/nitrogen. Then, 1,1'bis(diphenyllphosphino)ferrocenedichloropalladium (II) (104.8 mg, 0.143 mmol) was added at room temperature and the mixture was degassed again 3 times using the cycle vacuum/nitrogen. The reaction mixture was heated at 80° C. for 3 hours. The reaction mixture was cooled to room temperature and diluted with AcOEt. The organic layer was successively washed with aqueous 10% NaHCO$_3$ solution and saturated aqueous NaCl solution, dried over MgSO$_4$, filtered and concentrated. The residue (1.6 g) was purified by Normal phase on (Irregular SiOH 20-45 μm 450 g MATREX). Mobile phase (0.5% NH$_4$OH, 95% DCM, 5% MeOH). The pure fractions were collected and the solvent was evaporated yielding 700 mg (42%) of compound shown. F-26.

Example B7

Preparation of Compound

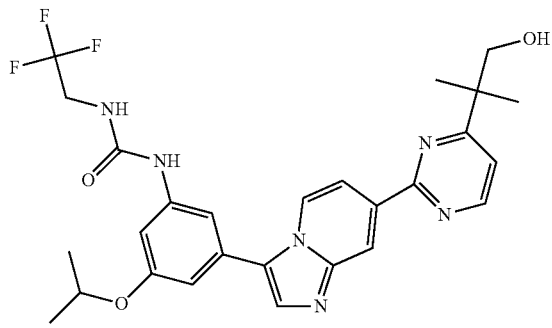 [SMILES: CC(C)Oc1cc(NC(=O)NCC(F)(F)F)cc(-c2cnc3cc(-c4nccc(C(C)(C)CO)n4)ccn23)c1]

A solution of compound of example B6 (F-26) (150 mg, 0.257 mmol) in THF (4 ml) was added dropwise to a suspension of lithium aluminium hydride (29.2 mg, 0.77 mmol) in THF (6 ml) previously cooled to 0° C. The reaction mixture was stirred for 3 hours allowing the temperature to reach room temperature. Then, it was hydrolysed successively with water (29 μl). NaOH 3N (58 μl) and water (29 μl). The mixture was partitioned between water and DCM. The organic layer was separated, dried over MgSO$_4$, filtered and concentrated. The residue (170 mg) was purified by Normal phase on (Sunfire Silica 5 μm 150×30.0 mm). Mobile phase (gradient from 0.2% NH$_4$OH, 98% DCM, 2% MeOH to 1.3% NH$_4$OH, 87% DCM, 13% MeOH). The pure fractions were collected and the solvent was evaporated, yielding 22 mg (15%) of compound shown. F-27

Example B8

Preparation of Compound

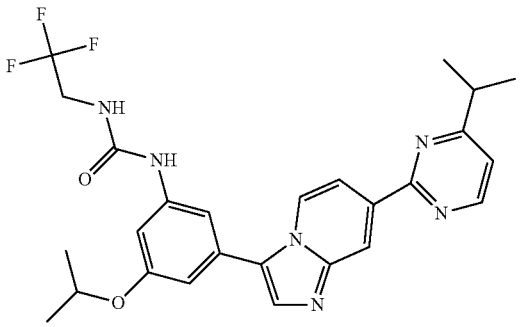 [SMILES: CC(C)Oc1cc(NC(=O)NCC(F)(F)F)cc(-c2cnc3cc(-c4nccc(C(C)C)n4)ccn23)c1]

A mixture of compound of example B6 (F-26) (440 mg, 0.753 mmol) and lithium hydroxide monohydrate (158 mg, 3.76 mmol) in dioxane (23.8 ml) and water (2.7 ml) was stirred at room temperature overnight. Then, additional lithium hydroxide monohydrate (158 mg, 3.76 mmo) was added and the mixture was stirred for 72 hours at room temperature. The reaction mixture was then acidified with HCl 3N and the solvent was evaporated, yielding 700 mg of a compound which was used in the next step.

To a solution of this compound (350 mg, 0.377 mmol) and triethylamine (63 μl, 0.453 mmol) in 2-methyl-2-propanol (7 ml), was added diphenylphosphorylazide (85 μl, 0.396 mmol) at room temperature. The reaction mixture was refluxed for 24 hours. Then, it was cooled down to room temperature, and the solvent 2-methyl-2-propanol was evaporated under vacuum. The residue was diluted with Et$_2$O. The organic layer was successively washed with NaOH 3N (twice) and water, dried over MgSO$_4$, filtered and concentrated. The residue (760 mg) was purified by Normal phase on (Irregular SiOH 15-40 μm 30 g). Mobile phase (gradient from 0% NH$_4$OH, 98% DCM, 2% MeOH to 0.5% NH$_4$OH, 94% DCM, 6% MeOH). The pure fractions were collected and the solvent was evaporated yielding 159 mg of an impure fraction. This fraction was than purified again by Normal phase on (Sunfire Silica 5 μm 150×30.0 mm). Mobile phase (gradient from 0.2% NH$_4$OH, 98% DCM, 2% MeOH to 0.9% NH$_4$OH, 91% DCM, 9% MeOH). The pure fractions were collected and the solvent was evaporated yielding 72 mg (37%) of compound shown (MP=159° C., DSC). F-29

Example B9a

Preparation of Compound

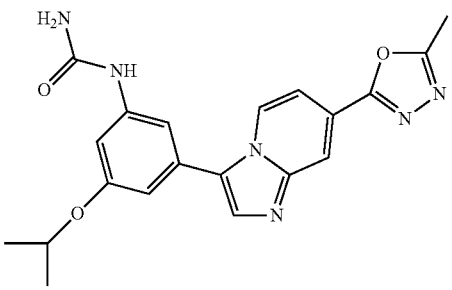 [SMILES: Cc1nnc(-c2ccn3c(-c4cc(NC(N)=O)cc(OC(C)C)c4)cnc3c2)o1]

At room temperature, to a solution of intermediate of example A11.c (1.45 g, 2.9 mmol, purity 70%) in THF (25 ml) was added 4-nitrophenyl chloroformate (0.65 g, 3.19 mmol). The reaction mixture was then heated at 60° C. for 5 hours. Then, it was cooled to room temperature and ammonia (0.5N in dioxane) (58.1 ml, 29.05 mmol) was added. The resulting mixture was stirred at room temperature overnight.

The experimental procedure above was repeated another time on the some quantity of intermediate of example A11.c. Then, the reaction mixtures were mixed for the work-up.

The resulting mixture was partitioned between water and DCM. The organic layer was separated, washed with water, dried over MgSO$_4$, filtered and concentrated. The residue was purified by Normal phase on (Irregular SiOH 15-40 μm 300 g MERCK). Mobile phase (gradient from 0% NH$_4$OH, 96% DCM, 4% MeOH to 0.5% NH$_4$OH, 94% DCM, 6% MeOH). The pure fractions were collected and the solvent was evaporated yielding 1.4 g (61%) of compound shown. F-31

Example B9b

Preparation of Compound

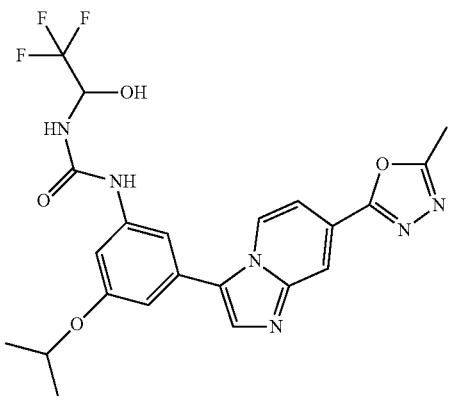 [SMILES: Cc1nnc(-c2ccn3c(-c4cc(NC(=O)NC(O)C(F)(F)F)cc(OC(C)C)c4)cnc3c2)o1]

At room temperature, to a solution of compound of example B9.a (F-31) (0.325 g, 0.828 mmol) in dioxane (10 ml) was added trifluoroacetaldehyde ethyl hemiacetal (CAS: 433-27-2)(0.9 ml, 6.93 mmol), trifluoroacetaldehyde hydrate (75% in water) (0.97 ml) and molecular sieves 3 Å (0.97 g). Then, the resulting mixture was heated at 100° C. for 3 hours in a microwave Biotage device. The experimental procedure above was repeated four times on the some quantities. Then, the reaction mixtures were mixed for the work-up.

The resulting mixture was filtered and concentrated. The residue (5.8 g) was purified by Normal phase on (Irregular SiOH 15-40 μm 300 g MERCK). Mobile phase (0.5% NH$_4$OH, 92% DCM, 8% MeOH). The pure fractions were collected and the solvent was evaporated yielding an intermediate fraction (2 g) which was crystallized with acetonitrile to afford 764 mg (47%) of compound shown (MP=186° C., DSC). F-32

Example B10

Preparation of Compound

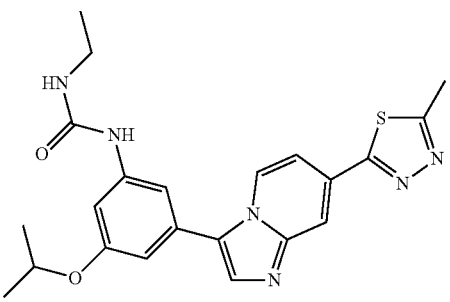 [SMILES: CCNC(=O)Nc1cc(OC(C)C)cc(-c2cnc3cc(-c4nnc(C)s4)ccn23)c1]

A mixture of 1-[3-isopropoxy-5-(4,4,5,5-tetramethyl-[1,3,2]dioxaborolan-2-yl)-phenyl]-3-ethylurea (prepared according to intermediate of example A1.n; 500 mg, 1.43 mmol), 3-iodo-7-[5-methyl-[1,3,4]thiadiazol-2-yl]-imidazo[1,2-a] pyridine (prepared according to Example A6; 442 mg, 1.29 mmol) and potassium phosphate in dioxane (20 ml) and water (5 ml) was degassed for 15 minutes at room temperature with nitrogen. Then, 1,1'bis(diphenyllphosphino)ferrocenedichloropalladium (II) (117 mg, 0.144 mmol) was added and the reaction mixture was heated to 80° C. for 3 hours. The mixture was cooled down to room temperature and partitioned between water and AcOEt. Then, it was filtered through a pad of celite. The organic layer was separated, washed with saturated aqueous NaCl solution, dried over MgSO$_4$, filtered and concentrated. The crude material (0.7 g) was purified by Normal phase on (Sunfire Silica 5 μm 150×30.0 mm). Mobile phase (gradient from 0.2% NH$_4$OH, 98% DCM, 2% MeOH to 0.8% NH$_4$OH, 92% DCM, 8% MeOH). The pure fractions were collected and the solvent was evaporated yielding 84 mg of an intermediate fraction which was crystallized with Et$_2$O to afford after filtration 54 mg (8%) of the compound shown (MP=206° C., DSC). F-23

Example B11

Preparation of Compound

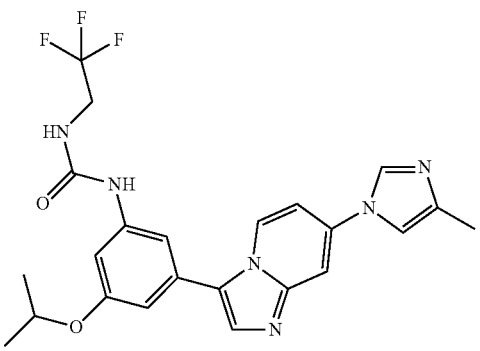 [SMILES: Cc1cn(-c2ccn3c(-c4cc(NC(=O)NCC(F)(F)F)cc(OC(C)C)c4)cnc3c2)cn1]

A mixture of intermediate of example A13.c (350 mg, 1.08 mmol), intermediate of example A1.n (478 mg, 1.18 mmol), potassium phosphate (504 mg, 2.37 mmol) in dioxane (6.8 ml) and water (3.3 ml) was stirred at room temperature under N₂ flow. After 10 minutes 1,1'bis(diphenyllphosphino) ferrocenedichloropalladium (II) (79 mg, 0.108 mmol) was added at room temperature under N₂ flow. The reaction mixture was heated at 90° C. for 3.5 hours. The reaction mixture was cooled to room temperature and poured onto ice-water. Then. AcOEt was added and the mixture was filtered through a pad of celite. The organic layer was separated, dried over MgSO₄, filtered and concentrated. The residue (503 mg) was purified by Normal phase on (Stability Silica 5 μm 150×30.0 mm). Mobile phase (Gradient from 0.4% NH₄OH, 96% DCM, 4% MeOH to 1.4% NH₄OH, 86% DCM, 14% MeOH). The pure fractions were collected and the solvent was evaporated to afford an intermediate fraction (200 mg) which was not pure enough (even after recrystallisation). So, this fraction was purified again by achiral Super critical fluid chromatography on (CYANO 6 μm 150×21.2 mm). Mobile phase (0.3% Isopropylamine, 88% CO₂, 12% MeOH). The pure fractions were collected and the solvent was evaporated to afford 101 mg (19%) of the compound shown (MP=243° C., DSC). F-28

Example B12

Preparation of Compound

A mixture of intermediate of example A3.b (487 mg, 1.5 mmol), intermediate of example A12.f (600 mg, 1.5 mmol), potassium phosphate (636 mg, 3 mmol) in dioxane (36 ml) and water (18 ml) was stirred at room temperature under N₂ flow. After 10 minutes 1,1'bis(diphenyllphosphino) ferrocenedichloropalladium (11) (122 mg, 0.15 mmol) was added at room temperature under N₂ flow. The reaction mixture was heated at 90° C. for 3 hours. The reaction mixture was cooled to room temperature and poured onto ice-water. Then. AcOEt was added and the mixture was filtered through a pad of celite. The organic layer was separated, dried over MgSO₄, filtered and concentrated. The residue (940 mg) was purified by Normal phase on (Spherical SiOH 10 μm 60 g PharmPrep MERCK). Mobile phase (0.6% NH₄OH, 94% DCM, 6% MeOH). The pure fractions were collected and the solvent was evaporated to afford an intermediate fraction (404 mg) which was not pure enough. So, this fraction was purified again by Reverse phase on (X-Bridge-C18 5 μm 30*150 mm). Mobile phase (Gradient from 50% NH₄HCO₃ (0.5%), 50% MeOH to 0% NH₄HCO₃ (0.5%), 100% MeOH). The pure fractions were collected and the solvent was evaporated to afford an intermediate fraction (404 mg) which was crystallized with acetonitrile to afford, after filtration, 251 mg (35%) of the compound shown (MP=178° C., DSC). F-30

TABLE F

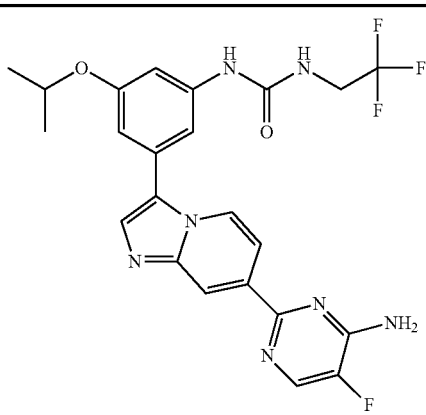

Compound F-1, example B1

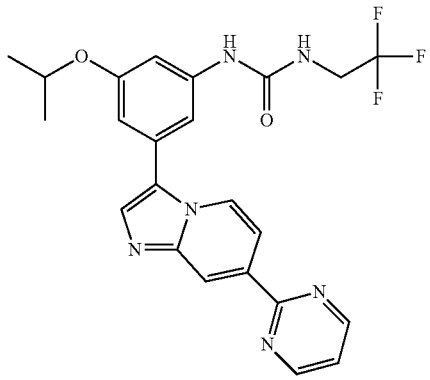 [SMILES: CC(C)Oc1cc(NC(=O)NCC(F)(F)F)cc(-c2cnc3cc(-c4ncccn4)ccn23)c1]

Compound F-2, example B1
mp. 219.08° C.

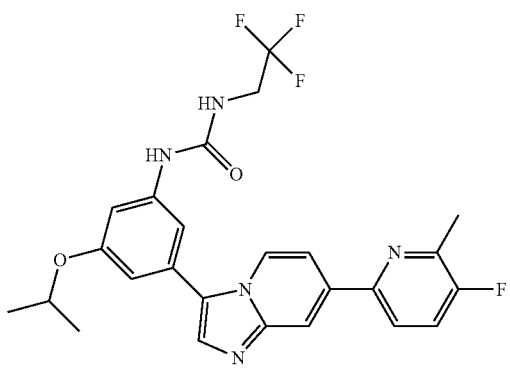 [SMILES: Cc1nc(-c2ccn3c(-c4cc(NC(=O)NCC(F)(F)F)cc(OC(C)C)c4)cnc3c2)ccc1F]

Compound F-3, example B1

TABLE F-continued
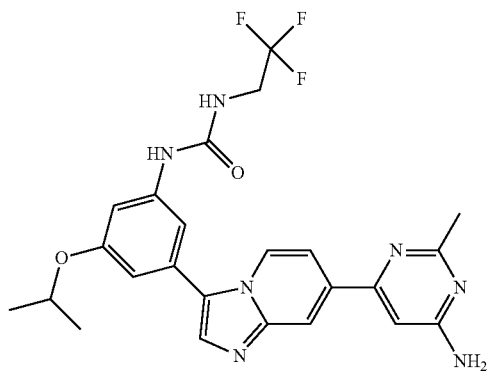 [SMILES: Cc1nc(N)cc(-c2ccn3c(-c4cc(NC(=O)NCC(F)(F)F)cc(OC(C)C)c4)cnc3c2)n1]
Compound F-4, example B1
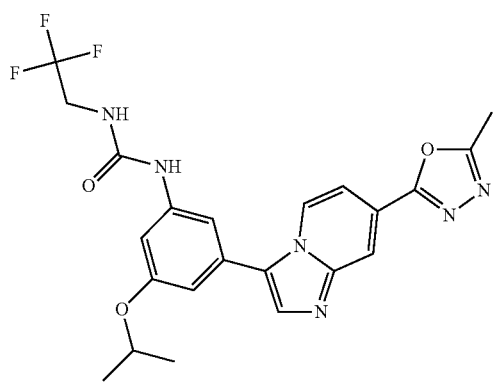 [SMILES: Cc1nnc(-c2ccn3c(-c4cc(NC(=O)NCC(F)(F)F)cc(OC(C)C)c4)cnc3c2)o1]
Compound F-5, example B2a
mp. 223.73° C.
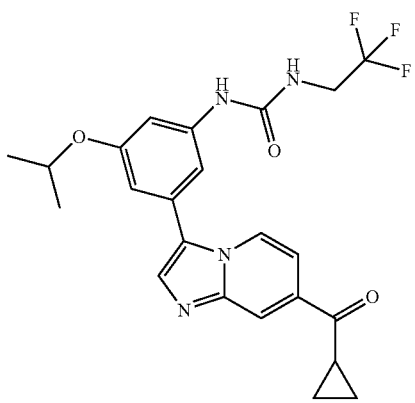 [SMILES: CC(C)Oc1cc(NC(=O)NCC(F)(F)F)cc(-c2cnc3cc(C(=O)C4CC4)ccn23)c1]
Compound F-6, example B2a
mp. 190.61° C.
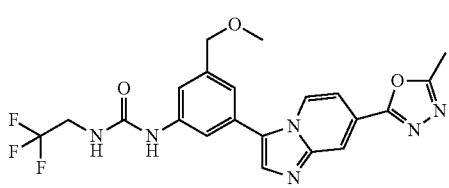 [SMILES: COCc1cc(NC(=O)NCC(F)(F)F)cc(-c2cnc3cc(-c4nnc(C)o4)ccn23)c1]
Compound F-7, example B2a
mp. 232° C.
TABLE F-continued
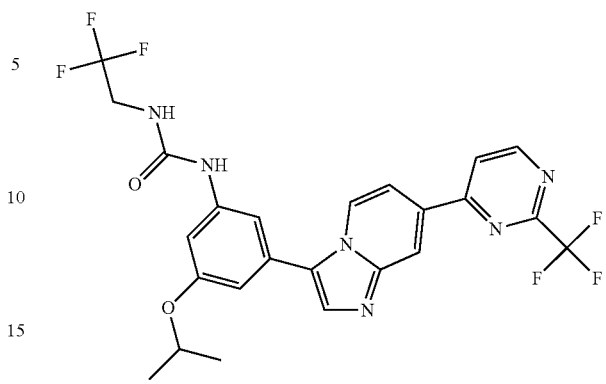
Compound F-8, example B2a
mp. 211.08° C.
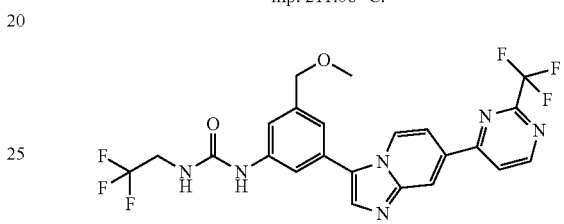
Compound F-9, example B2a
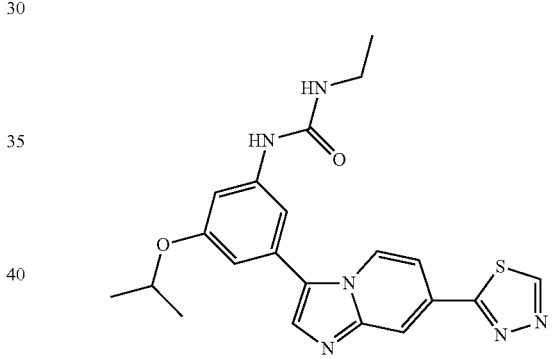
Compound F-10, example B2a
mp. 120.98° C.
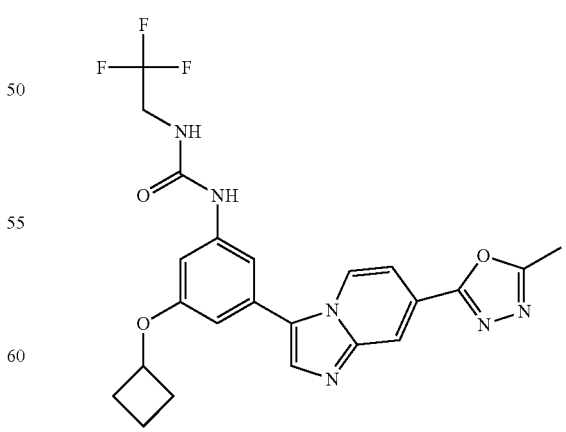
Compound F-11, example B2a
mp. 217.32° C.

TABLE F-continued
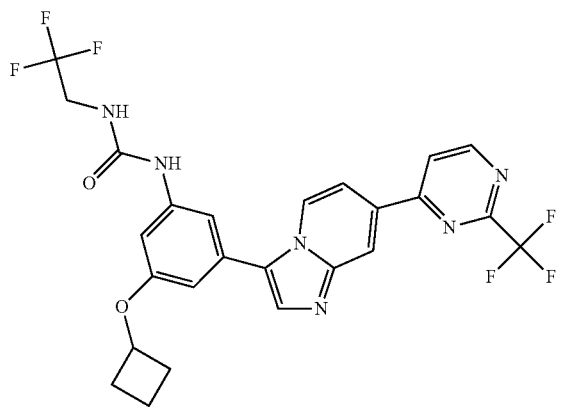 [SMILES: O=C(NCC(F)(F)F)Nc1cc(OC2CCC2)cc(-c2cnc3cc(-c4ccnc(C(F)(F)F)n4)ccn23)c1]
Compound F-12, example B2a
mp. 216.89° C.
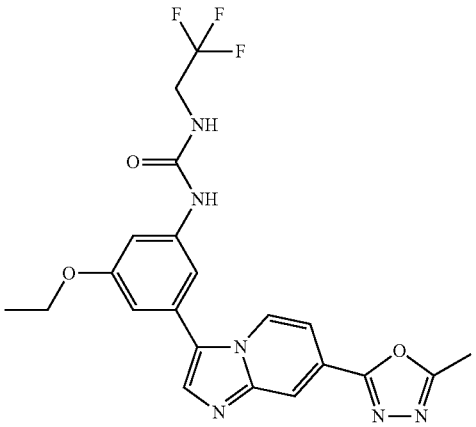
Compound F-15, example B2b.1
mp. 234.76° C.
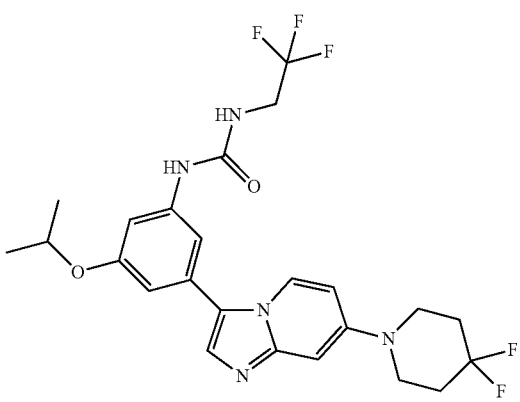 [SMILES: CC(C)Oc1cc(NC(=O)NCC(F)(F)F)cc(-c2cnc3cc(N4CCC(F)(F)CC4)ccn23)c1]
Compound F-13, example B2a
mp. 218.75° C.
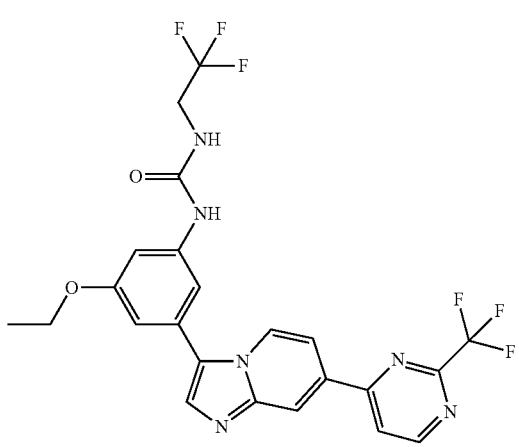
Compound F-16, example B2b.1
mp. 241.43° C.
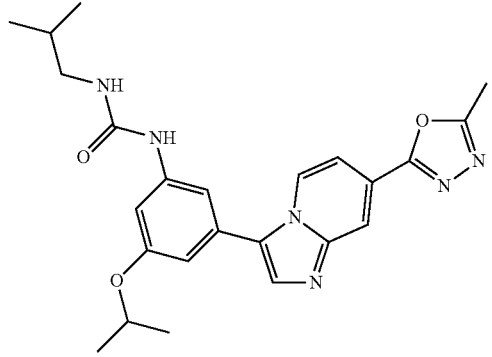 [SMILES: Cc1nnc(-c2ccn3c(-c4cc(NC(=O)NCC(C)C)cc(OC(C)C)c4)cnc3c2)o1]
Compound F-14, example B2a
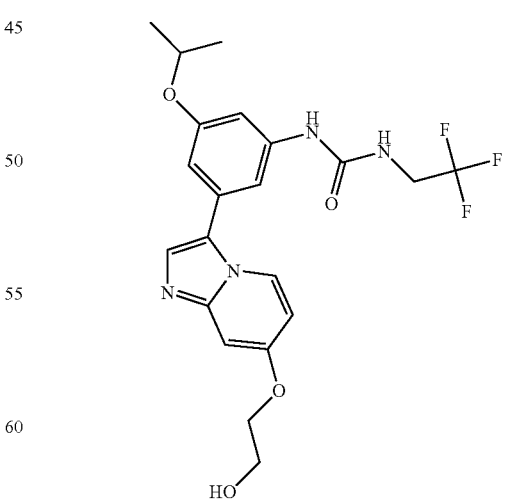
Compound F-17, example B3
mp. 185.42° C.

TABLE F-continued
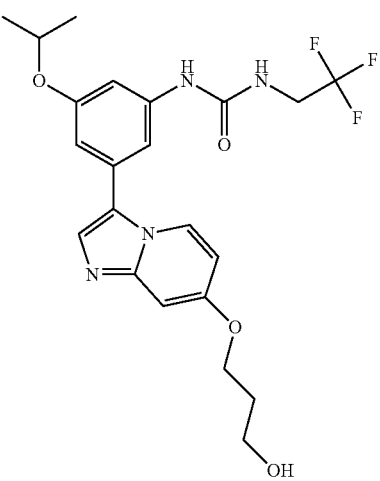 [SMILES: CC(C)Oc1cc(NC(=O)NCC(F)(F)F)cc(-c2cnc3cc(OCCCO)ccn23)c1]
Compound F-18, example B3
mp. 186.92° C.
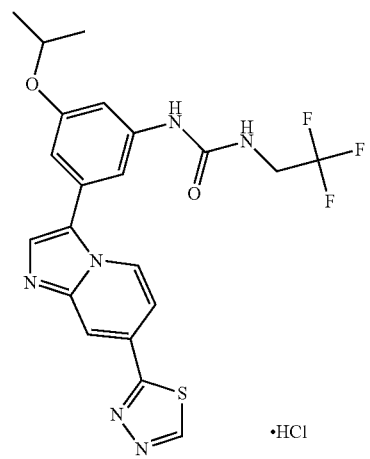 [SMILES: CC(C)Oc1cc(NC(=O)NCC(F)(F)F)cc(-c2cnc3cc(-c4nncs4)ccn23)c1 ; Cl]
•HCl
Compound F-19, example B2b.2
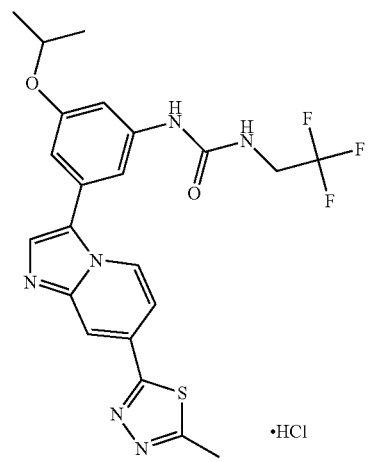 [SMILES: Cc1nnc(-c2ccn3c(-c4cc(NC(=O)NCC(F)(F)F)cc(OC(C)C)c4)cnc3c2)s1 ; Cl]
•HCl
Compound F-20, example B2b.2
TABLE F-continued
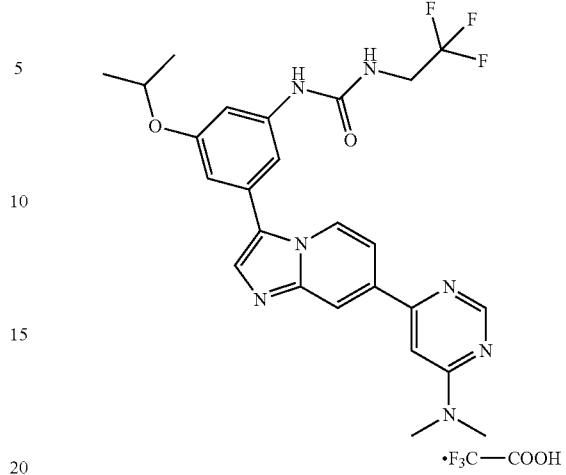
•F$_3$C—COOH
Compound F-21, example B2b.2
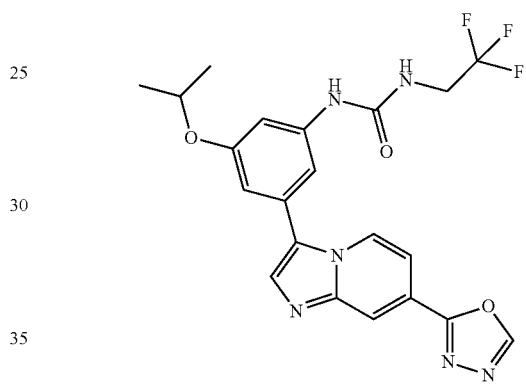
Compound F-22, example B2b.2
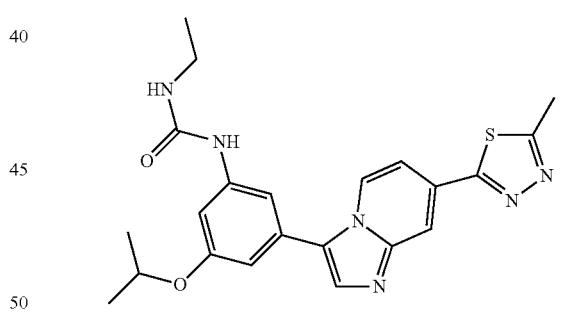
Compound F-23, example B10
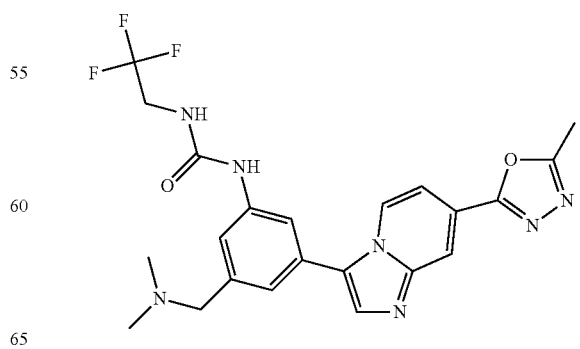
Compound F-24, example B4

TABLE F-continued
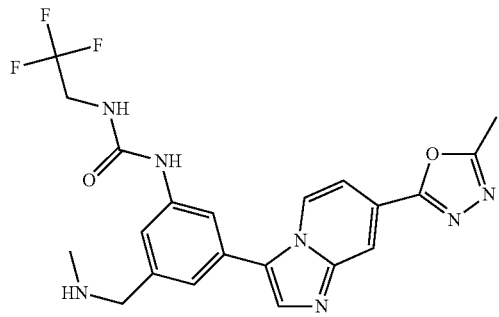 [SMILES: CNCc1cc(NC(=O)NCC(F)(F)F)cc(-c2cnc3cc(-c4nnc(C)o4)ccn23)c1]
Compound F-25, example B5
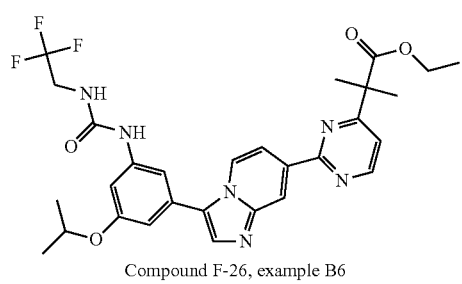
Compound F-26, example B6
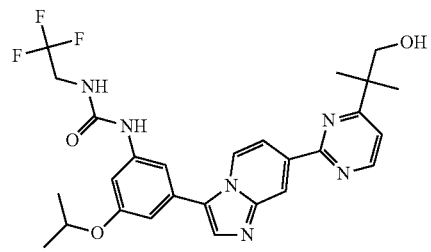 [SMILES: CC(C)Oc1cc(NC(=O)NCC(F)(F)F)cc(-c2cnc3cc(-c4nccc(C(C)(C)CO)n4)ccn23)c1]
Compound F-27, example B7
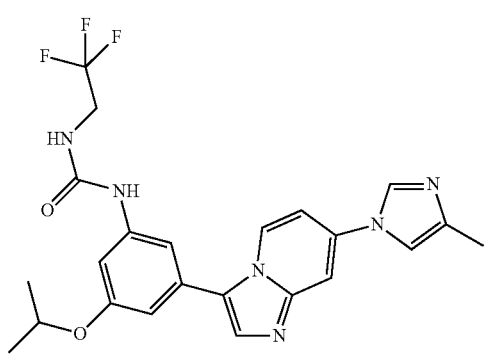 [SMILES: Cc1cn(-c2ccn3c(-c4cc(NC(=O)NCC(F)(F)F)cc(OC(C)C)c4)cnc3c2)cn1]
Compound F-28, example B11
TABLE F-continued
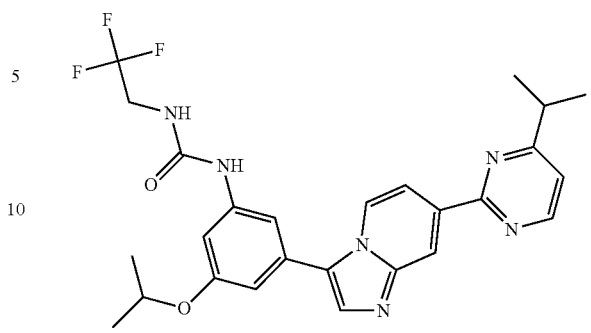
Compound F-29, example B8
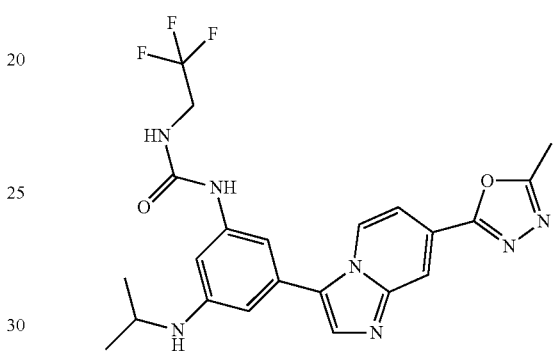
Compound F-30, example B12
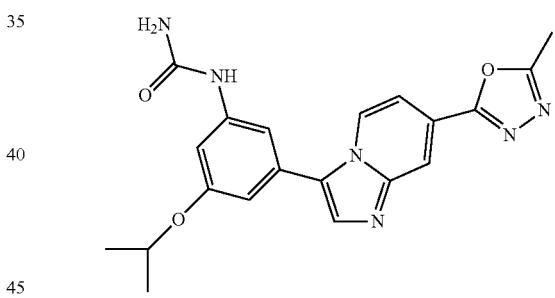
Compound F-31, example B9a
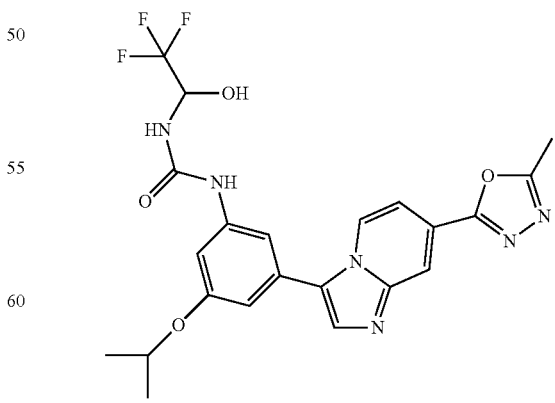
Compound F-32, example B9b Analytical Part
LCMS
LCMS General Procedure The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

LCMS—Procedure

In addition to the general procedure: Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

TABLE 2

Analytical data - Retention time ($R_t$ in minutes) and $(MH)^+$ peak

| Compound no.. | $R_t$ | $[M + H]^+$ |
|---|---|---|
| F-1 | 3.44 | 504 |
| F-3 | 4.03 | 501 |
| F-4 | 3.19 | 500 |
| F-9 | 3.62 | 525 |
| F-14 | 3.42 | 449 |
| F-24 | 2.45 | 474 |
| F-25 | 2.25 | 460 |
| F-27 | 3.61 | 543 |
| F-29 | 4.19 | 513 |
| F-32 | 3.15 | 491 |
| F-23 | 3.13 | 437 |
| F-28 | 3.27 | 473 |
| F-30 | 3.18 | 474 |

Analytical LC-MS System and Method Description

The examples below were characterised by liquid chromatography and mass spectroscopy using the systems and operating conditions set out below. Where atoms with different isotopes are present and a single mass quoted, the mass quoted for the compound is the monoisotopic mass (i.e. $^{35}Cl$; $^{79}Br$ etc.). Several systems were used, as described below, and these were equipped with, and were set up to run under, closely similar operating conditions. The operating conditions used are also described below.

Adilent 1200SL-6140 LC-MS System—RAPID:
HPLC System: Agilent 1200 series SL
Mass Spec Detector: Agilent 6140 single quadrupole
Second Detector Agilent 1200 MWD SL
BASIC_RR01
Eluent A: 95:5 10 mM NH4HCO3+NH4OH:CH3CN (pH=9.2)
Eluent B: $CH_3CN$
Gradient: 5-95% eluent B over 1.1 minutes
Flow: 0.9 ml/min
Column: Waters Acquity UPLC BEH C18; 1.7μ; 2.1×50 mm
Column T: 50° C.
Agilent MS Running Conditions:
Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-800 amu
Ionisation Mode ElectroSpray Positive-Negative switching

| F-19 | MS: $[M + H]^+$ 477 |
| F-20 | MS: $[M + H]^+$ 491 |
| F-22 | MS: $[M + H]^+$ 461 |
| F-21 | MS: $[M + H]^+$ 514 |

Mass Directed Purification LC-MS System

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K. Wisnoski O. Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

One such system for purifying compounds via preparative LC-MS is described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS System Description:
Waters Fractionlynx System:
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1
Waters MS Running Conditions:
Capillary voltage: 3.5 kV (3.2 kV on ES Negative)
Cone voltage: 25 V Source Temperature: 120° C.
Multiplier: 500 V
Scan Range: 125-800 amu
Ionisation Mode ElectroSpray Positive or
ElectroSpray Negative
Agilent 1100 LC-MS Preparative System:
Hardware:
Autosampler: 1100 series "prepALS"
Pump: 1100 series "PrepPump" for preparative flow gradient and 1100 series
"QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
Software:
Chemstation: Chem32
Agilent MS Running Conditions:
Capillary voltage: 4000 V (3500 V on ES Negative
Fragmentor/Gain: 150/1
Drying gas flow: 13.0 L/min
Gas Temperature: 350° C.
Nebuliser Pressure: 50 psig
Scan Range: 125-800 amu
Ionisation Mode: ElectroSpray Positive or
ElectroSpray Negative
Columns:
1. Low pH chromatography:
Phenomenex Synergy MAX-RP, 10µ, 100×21.2 mm
(alternatively used Thermo Hypersil-Keystone HyPurity Aquastar, 5µ, 100×21.2 mm for more polar compounds)
2. High pH chromatography:
Waters XBridge C18 100×19 mm
(alternatively used Phenomenex Gemini, 5µ, 100×21.2 mm)
Eluents:
1. Low pH chromatography F.A.:
Solvent A: $H_2O$+0.1% Formic Acid, pH~2.3
Solvent B: $CH_3CN$+0.1% Formic Acid
Solvent C: $CH_3OH$+0.1% Formic Acid
2. Low pH chromatography TFA:
Solvent A: $H_2O$+0.1% TFA, pH~1.5
Solvent B: $CH_3CN$+0.1% TFA
Solvent C: $CH_3OH$+0.1 TFA
3. High pH chromatography:
Solvent A: $H_2O$+10 mM $NH_4HCO_3$+NH4OH, pH=9.2
Solvent B: $CH_3CN$
Solvent B: $CH_3OH$
4. Make up solvent:
MeOH+0.2% Formic Acid (for all chromatography type)
Methods:
According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running condition for both low and high pH chromatography methods were:
Flow rate: 24 ml/min
Gradient: Generally all gradients had an initial 0.4 min step with 95% A+5% B (or C). Then according to analytical trace a 3.6 min gradient was chosen in order to achieve good separation (e.g. from 5% to 50% B for early retaining compounds; from 35% to 80% B for middle retaining compounds and so)
Wash: 1.2 minute wash step was performed at the end of the gradient
Re-equilibration: 2.1 minutes re-equilibration step was ran to prepare the system for the next run
Make Up flow rate: 1 ml/min
Solvent:
All compounds were usually dissolved in 100% MeOH or 100% DMSO
From the information provided someone skilled in the art could purify the compounds described herein by preparative LC-MS.
NMR Data
Compound F-19
1H NMR (400 MHz, DMSO-d6): 9.81 (1H, s), 9.21 (1H, s), 8.84 (1H, d), 8.52 (1H, s), 8.32 (1H, s), 7.94 (1H, dd), 7.33 (1H, s), 7.26 (1H, t) 7.00 (1H, t) 6.87 (1H, s), 4.72-4.60 (1H, m), 3.99-3.90 (2H, m), 1.32 (6H, d).
Compound F-20
1H NMR (400 MHz, DMSO-d6): 9.35 (1H, s), 8.86 (1H, d), 8.47 (1H, s), 8.42 (1H, s), 7.95 (1H, dd), 7.34 (1H, s), 7.27 (1H, t), 7.07 (1H, t), 6.87 (1H, s), 4.72-4.59 (1H, m), 3.99-3.90 (2H, m), 2.87 (3H, s), 1.32 (6H, d).
Compound F-21
$^1$H NMR (DMSO-d6) 9.04 (1H, br s), 8.78 (1H, d), 8.67 (1H, 2), 8.65 (1H, s), 8.20 (1H, br s), 8.02 (1H, d), 7.44 (1H, s), 7.36 (1H, s), 7.18 (1H, m), 6.94 (1H, d), 6.86 (1H, m), 4.66 (1H, m), 3.94 (2H, m), 3.23 (6H, s), 1.32 (6H, d)
Compound F-22
$^1$H NMR (DMSO-d6) 9.43 (1H, s), 9.32 (1H, br s), 8.74 (1H, d), 8.27 (1H, s), 7.96 (1H, s), 7.55 (1H, dd), 7.30-7.25 (3H, m), 6.80 (1H, s), 4.66 (1H, m), 3.92 (2H, m), 1.31 (6H, d)
Compound F-26
$^1$H NMR (500 MHz, DMSO-d6) δ 8.88-9.01 (2H, m), 8.69 (1H, d, J=7.2 Hz), 8.57 (1H, s), 7.83-7.96 (2H, m), 7.54 (1H, d, J=5.4 Hz), 7.22 (2H, m), 6.86 (1H, t, J=6.1 Hz), 6.81 (1H, s), 4.66 (1H, q, J=6.1 Hz), 4.14 (2H, qt, J=7.1 Hz), 3.86-4.00 (2H, m), 1.61 (6H, s), 1.31 (6H, d, J=6.1 Hz), 1.13 (3H, t, J=7.1 Hz).
Compound F-27
$^1$H NMR (500 MHz, DMSO-d6) δ 8.98 (1H, s), 8.84 (1H, d, J=5.4 Hz), 8.69 (1H, d, J=7.2 Hz), 8.62 (1H, s), 7.96 (1H, d, J=7.2 Hz), 7.89 (1H, s), 7.49 (1H, d, J=5.4 Hz), 7.24 (1H, s), 7.20 (1H, s), 6.89 (1H, t, J=6.1 Hz), 6.81 (1H, s), 4.78 (1H, t, J=5.4 Hz), 4.67 (1H, qt, J=6.1 Hz), 3.87-4.00 (2H, m), 3.66 (2H, d, J=6.1 Hz), 1.34 (6H, s), 1.31 (6H, d, J=6.1 Hz).
Compound F-31
$^1$H NMR (400 MHz, DMSO-d6) δ 8.64-8.76 (2H, m), 8.17 (1H, s), 7.93 (1H, s), 7.49 (1H, dd, J=1.5, 7.6 Hz), 7.22 (1H, s), 7.19 (1H, s), 6.75 (1H, s), 5.95 (2H, s), 4.64 (1H, qt, J=6.1 Hz), 2.62 (3H, s), 1.25-1.34 (6H, d, J=6.1 Hz).
Biological Assays
FGFR3, VEGFR2 and PDGFR in vitro Kinase Inhibitory Activity Assays
Enzymes (from Upstate), prepared at 2× final concentration, were incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 3 hours (FGFR3), 1 hour (VEGFR2, PDGFR-beta) at room temperature on a plate shaker at 700 rpm before being stopped with 35 mM EDTA, pH 8 (FGFR3, VEGFR2) or 55 mM EDTA, pH 8 (PDGFR-beta). 5× detection mix/50 mM HEPES pH 7.5, 0.1% BSA, 11.34 nM Eu-anti-pY (PY20) (PerkinElmer) 74 nM SA-XL665 (Cisbio) for FGFR3, 50 mM HEPES, pH 7.5, 0.1% BSA, 11.34 nM Eu-anti-pY (PY20), 187.5 nM SA-XL665 for VEGFR2 and 50 mM HEPES, pH 7.5, 0.1% BSA, 11.34 nM Eu-anti-pY (PT66) (PerkinElmer), 375 nM SA-XL665 (Cisbio) for PDGFR-beta) was then added to each well and the plate sealed and incubated at room temperature for one hour on a plate shaker at 700 rpm. The plate was then read on a Packard Fusion plate reader or a BMG Pherastar both in TRF mode.

TABLE 1

Final assay conditions for FGFR3, VEGFR2 and PDGFR-beta assays

| Enzyme | 1 × Assay Buffer | Flt3 substrate concentration | ATP concentration |
|---|---|---|---|
| FGFR3 | A | 0.125 μM | 8 μM |
| VEGFR2 | B | 0.5 μM | 0.5 μM |
| PDGFR-beta | C | 1 μM | 70 μM |

Kinase Assay buffers were:
A: 50 mM HEPES pH 7.5, 6 mM $MnCl_2$, 1 mM DTT, 0.01% TritonX-100
B: 50 mM HEPES pH 7.5, 6 mM $MnCl_2$, 1 mM DTT, 0.01% TritonX-100, 0.1 mM Sodium orthovanadate
C: 20 mM HEPES pH 7.5, 10 mM $MnCl_2$, 0.01% Triton X-100, 1 mM DTT, 0.1 mM Sodium orthovanadate FGFR3 and VEGFR2 Data for the compounds of the invention in the above assays are provided in Table A.

FGFR1, FGFR2, FGFR4, VEGFR1 and VEGFR3 In vitro Kinase Inhibitory Activity Assays The inhibitory activity against FGFR1, FGFR2, FGFR4, VEGFR1 and VEGFR3 can be determined at Upstate Discovery Ltd. Enzymes are prepared at 10× final concentration in enzyme buffer (20 mM MOPS, pH 7.0, 1 mM EDTA, 0.1% B-mercaptoethanol, 0.01% Brij-35, 5% glycerol, 1 mg/ml BSA). Enzymes are then incubated in assay buffer with various substrates and $^{33}$P-ATP (~500 cpm/pmol) as described in the table.

The reaction is initiated by the addition of Mg/ATP. The reaction is allowed to proceed for 40 minutes at room temperature before being stopped with 5 μl of a 3% phosphoric acid solution. Ten μl of the reaction mix is transferred to either a filtermatA or P30 filtermat and washed three times in 75 mM phosphoric acid and once in methanol before being dried for scintillation counting.

Compounds are tested at the concentrations of the assay reagents as detailed below in duplicate against all kinases and the percent activity compared to control is calculated. Where inhibition is high an $IC_{50}$ can be determined.

| Enzyme | Assay Buffer | Substrate | ATP Concentration (μM) |
|---|---|---|---|
| FGFR1 | A | 250 μM KKKSPGEYVNIEFG | 200 μM |
| FGFR2 | B | 0.1 mg/ml poly(Glu, Tyr) 4:1 | 90 μM |
| FGFR4 | C | 0.1 mg/ml poly(Glu, Tyr) 4:1 | 155 μM |
| VEGFR1 | A | 250 μM KKKSPGEYVNIEFG | 200 μM |
| VEGFR3 | A | 500 μM GGEEEEYFELVKKKK | 200 μM |

Enzyme buffer A: 8 mM MOPS, pH 7.0, 0.2 mM EDTA, 10 mM MgAcetate
Enzyme buffer B: 8 mM MOPS, pH 7.0, 0.2 mM EDTA, 2.5 mM MnCl2, 10 mM MgAcetate
Enzyme buffer C: 8 mM Mops, pH 7.0, 0.2 mM EDTA, 10 mM MnCl2, 10 mM MgAcetate.

Cell-Based pERK ELISA Method

LP-1 or JIM-1 multiple myeloma cells were seeded in 96 well plates at 1×10$^6$ cells/ml in 200 ul per well in serum free media. HUVEC cells were seeded at 2.5×10$^6$ cells/ml and allowed to recover for 24 h prior to transfer to serum free media. Cells were incubated for 16 h at 37° C. prior to the addition of a test compound for 30 minutes. Test compounds were administered at a 0.1% final DMSO concentration. Following this 30 minute incubation a FGF-1/Heparin (FGF-1 at 100 ng/ml final and Heparin at 100 ug/ml) mixture or VEGF$^{165}$ (100 ug/ml) was added to each of the wells for a further 5 minutes. The media was removed and 50 ul ERK ELISA lysis buffer (R and D Systems DuoSet ELISA for pERK and Total ERK #DYC-1940E, DYC-1018E) added. ELISA plates and standards were prepared according to the standard DuoSet protocols and the relative amounts of pERK to total ERK in each sample calculated according to the standard curve.

In particular, compounds of the invention were tested against the LP-1 cell line (DSMZ no.: ACC 41) derived from human multiple myeloma.

HUVEC Cell Based Selectivity Assays

HUVEC cells are seeded in 6 well plates at 1×10$^6$ cells/well and allowed to recover for 24 h. They are transferred to serum free media for 16 hours prior to treatment with test compound for 30 minutes in 0.1% DMSO final. Following compound incubation FGF-1 (100 ng/ml) and Heparin (100 ug/ml) or VEGF$^{165}$ (100 ng/ml) are added for 5 minutes. Media is removed, cells washed with ice-cold PBS and lysed in 100 ul TG lysis buffer (20 mM Tris, 130 nM NaCl, 1% Triton-X-100, 10% Glycerol, protease and phosphatase inhibitors, pH 7.5). Samples containing equivalent amounts of protein are made up with LDS sample buffer and run on SDS PAGE followed by western blotting for a number of downstream VEGFR and FGFR pathway targets including phospho-FGFR3, phospho-VEGFR2 and phospho-ERK1/2. The western blot can then be analysed by visual inspection or densitometry.

Ba/F3-TEL-FGFR3 & Ba/F3 (WT) Cell Proliferation Assays

Stably transfected Ba/F3-TEL-FGFR3 cells were plated out into black 96-well tissue culture plates with clear bottoms in RPMI medium containing 10% FBS and 0.25 mg/ml G418 at a density of 5×10$^3$ cells/well (200 μl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Systems) at a density of 2.5×10$^3$ cells/well (200 μl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 μl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an $IC_{50}$ can be determined.

Data for the compounds of the invention in the above assays are provided in Table A.

TABLE A

| Compound No | FGFR3 IC50(μM) or % I | VEGFR2 IC50(μM) or % I | BaF3 WT prolif (μM) | BaF3-TEL-FGFR3 prolif (μM) |
|---|---|---|---|---|
| F-1 | 0.00720 | 1.35 | 42.0% at 10.0 μM | 0.12 |
| F-2 | 0.0144 | 1.14 | 33.0% at 10.0 μM | 0.17 |
| F-5 | 0.0154 | 0.635 | 59.0% at 10.0 μM | 0.22 |
| F-19 | 0.00247 | 0.092 | 0.000% at 1.00 μM | 0.042 |
| F-15 | 0.0250 | 0.340 | 23.0% at 10.0 μM | 0.37 |
| F-7 | 0.0180 | 0.170 | 0.000% at 10.0 μM | 0.35 |
| F-6 | 0.00120 | 0.0740 | 5.6 | 0.031 |
| F-8 | 0.0340 | 1.20 | 2 | 0.17 |
| F-13 | 0.0610 | 55.0% at 3 μM | 3.2 | 0.82 |
| F-17 | 0.0170 | 0.510 | 0.000% at 10.0 μM | 0.5 |
| F-16 | 0.0270 | 0.400 | 32.0% at 10.0 μM | 0.47 |
| F-20 | 0.000960 | 0.0290 | 0.000% at 3.00 μM | 0.009 |
| F-18 | 0.0200 | 0.670 | 54.0% at 10.0 μM | 0.44 |
| F-10 | 0.0130 | 0.360 | 34.0% at 10.0 μM | 0.23 |
| F-11 | 0.0460 | 59.0% at 1 μM | 14.0% at 10.0 μM | 0.52 |
| F-9 | 0.00930 | 0.0570 | 17.0% at 3.00 μM | 0.24 |
| F-12 | 60.0% at 0.3 μM | 2.20 | | |
| F-3 | 0.00870 | 0.480 | 8 | 0.33 |
| F-4 | 45.0% at 0.003 | 0.100 | 5.00% at 10.0 μM | 50.0% at 0.100 μM |
| F-22 | 0.041 | 1.1 | 19.0% at 10.0 μM | 1.3 |
| F-14 | 0.20 | 2.6 | — | — |
| F-21 | 0.012 | 0.79 | 2.3 | 0.24 |
| F-24 | — | 2.8 | — | — |
| F-25 | 0.46 | 1.7 | — | — |
| F-27 | 0.042 | 1.2 | 50% at 3.00 μM | 1.58 |
| F-29 | 0.092 | 53% at 10 μM | 3.98 | 3.16 |
| F-32 | — | 1.2 | — | — |
| F-23 | 0.004 | 0.087 | 5% at 10.00 μM | 0.05 |
| F-28 | 0.0016 | 0.077 | 73% at 10.00 μM | 0.1 |
| F-30 | 0.17 | 5.8 | — | — |

In Vivo Models of Hypertension

A number of animal models exist to measure the potential hypertensive effects of small molecule inhibitors. They can be classified into two main types; indirect and direct measurements. The most common indirect method is the cuff technique. Such methods have the advantages of being non-invasive and as such can be applied to a larger group of experimental animals however the process allows only intermittent sampling of blood pressure and requires the animal to be restrained in some way. Application of restraint can stress the animal and means that changes in blood pressure attributable to a specific drug effect can be hard to pick up.

Direct methodologies include those that make use of radio telemetry technology or via indwelling catheters connected to externally mounted transducers. Such methods require a high level of technical expertise for the initial surgery involved in implantation and costs involved are high. However a key advantage is that they allow continuous monitoring of blood pressure without restraint over the time period of the experiment. These methods are reviewed in Kurz et al (2005), Hypertension. 45, 299-310.

hERG Activity

The activity of compound of formula (I) against the hERG $K^+$ ion channel can be determined using the assay described in the article by M. H. Bridgland-Taylor et al., *Journal of Pharmacological and Toxicological Methods*, 54 (2006), 189-199. This IonWorks™ HT hERG screening assay is performed commercially by Upstate (Millipore) using the PrecisION™ hERG-CHO cell line.

Determination of Potency Against Cytochrome P450

The potency of the compound of formula (I) against cytochrome P450 (CYP450) enzymes 1A2, 2C9, 2019, 3A4 and 2D6 can be determined using the Pan Vera Vivid CYP450 screening kits available from Invitrogen (Paisley, UK). The CYP450s are supplied in the form of baculosomes containing the CYP450 and NADPH reductase and the substrates used are the fluorescent Vivid substrates. The final reaction mixtures are as follows:

1A2

100 mM potassium phosphate, pH 8, 1% acetonitrile, 2 μM 1A2 Blue vivid substrate, 100 μM $NADP^+$, 4 nM CYP450 1A2, 2.66 mM glucose-6-phosphate, 0.32 U/ml glucose-6-phosphate dehydrogenase.

$2C_{9-50}$ mM potassium phosphate, pH 8, 1% acetonitrile, 2 μM Green vivid substrate, 100 μM $NADP^+$, 8 nM CYP450 2C9, 2.66 mM glucose-6-phosphate, 0.32 U/ml glucose-6-phosphate dehydrogenase.

2C19

50 mM potassium phosphate, pH 8, 1% acetonitrile, 8 μM Blue vivid substrate, 100 μM $NADP^+$, 4 nM CYP450 2C19, 2.66 mM glucose-6-phosphate, 0.32 U/ml glucose-6-phosphate dehydrogenase.

3A4

100 mM potassium phosphate, pH 8, 1% acetonitrile, 10 μM 3A4 Blue vivid substrate. 100 μM $NADP^+$, 2.5 nM CYP450 3A4, 2.66 mM glucose-6-phosphate, 0.32 U/ml glucose-6-phosphate dehydrogenase.

2D6

100 mM potassium phosphate, pH 8, 1% acetonitrile, 5 μM 2D6 Blue vivid substrate, 100 μM $NADP^+$, 16 nM CYP450 2D6, 2.66 mM glucose-6-phosphate, 0.32 U/ml glucose-6-phosphate dehydrogenase.

Fluorescence is monitored for 20 minutes at 30 second intervals on a Molecular Devices Gemini fluorescence plate reader. The excitation and emission wavelengths are 390 nm and 460 nm for 1A2, 2C19 and 3A4, 390 nm and 485 nm for 2D6 and 485 nm and 530 nm for 2C9. Initial rates are determined from progress curves.

The test compound is made up in methanol or acetonitrile and tested against the CYP450s at a concentration of 10 μM.

Ba/F3-Flt3 Assay

Ba/F3, a murine interleukin-3 dependent pro-B cell line is increasingly popular as a model system for assessing both the potency and downstream signaling of kinase oncogenes, and the ability of small-molecule kinase inhibitors to block kinase activity. Facilitated by their growth properties. Ba/F3 cells have recently been adapted to high throughput assay formats for compound profiling. Further, several published approaches show promise in predicting resistance to small-molecule kinase inhibitors elicited by point mutations interfering with inhibitor binding (*Ba/F3 cells and their use in kinase drug discovery*; Markus Warmuth, Sungjoon Kim, Xiang-ju Gu, Gang Xia and Francisco Adria'n; Curr Opin Oncol 19:55-60).

Procedure:

Ba/F3-Flt3 cells (cultured in phenol red free RPMI-1640, 10% A FCS and 50 μg/ml Gentamycin at 37° C. and 5% 002) were plated at a density of 10000 cells in a total volume of 180 μl medium in a black TC-treated sterile 96-well plate (Corning). After 24 hours, drugs in different dilutions were added to a final volume of 200 μl and at a final DMSO concentration of 0.2% prior to incubation at 37° C., and 5% $CO_2$.

After 24 h, to each well 40 μl Alamar Blue solution (Aldrich) was added and the cells were further incubated for 4 hours at 37° C. Fluorescence (ex. 544, em. 590 nm) was measured using a fluorescence reader (Labsystems) and IC50's were calculated.

In the condition containing IL3, 10 ng/ml of murine IL3 (PeproTech) was added during compound incubation.

Ba/F3-Flt3 assay data for the compounds of the invention are provided in Table B.

EB1 Cellular Assay

The Eb1 Comet assay relies on the detection of the Eb1 protein at the plus end of polymerizing microtubules (Mimori-Kiyosue, 2000) using indirect immunofluorescence. Disruption of microtubule dynamics through de-polymerization or stabilization results in a de-localization of Eb1 from the growing microtubule ends and this is visualized by the disappearance of Eb1 containing cytoplasmic foci.

Briefly, human prostate cancer PC3 cells obtained from the American Type Culture Collection were grown in 96-well plates (Greiner, cat. no. 655090) in HAM's F12 medium as recommended by the provider (ATCC). The cells were treated for 1 hour at 37° C. with compounds dissolved in DMSO (0.6% final DMSO concentration). The culture medium was then removed by aspiration and the cells were fixed by adding cold methanol (−20° C.). After a 15 minutes incubation at −20° C., the cells were washed twice with DPBS (Gibco) containing 0.5% Triton X-100. Mouse Eb1 antibody (BD Transduction Laboratories, cat. no. 610534) was added to the cells (1/250 dilution in DPBS containing 1% BSA) and incubated overnight at room temperature. The antibody was subsequently removed and the cells washed twice with DPBS, 0.5% Triton X-100. Secondary goat anti-mouse antibody conjugated to Alexa 488 fluorescent dye (Molecular Probes) was added at a 1/500 dilution in DPBS, 1% BSA and incubated for 1 hour at 37° C. The cells were washed twice with DPBS, 0.5% Triton X-100 and then DPBS containing 0.5% Triton X-100 and 1/5000 Hoechst 33342 (Molecular Probes) was added. Microscopy based Eb1 foci visualization was carried out using an IN Cell Analyser 1000 (Amersham Biosciences) using a 20× objective. Compound dependent microtubule disruption was visually determined by the disappearance in Eb1 foci. The lowest active concentration (LAC) was determined as the concentration where Eb1 foci were absent in at least 50% of the treated cells. Herein the effects of test compounds are expressed as pLAC (the negative log value of the LAC-value)

EB1 cellular assay data for the compounds of the invention are provided in Table B.

TABLE B

| Compound no | Eb1 LAC μM | Ba/F3-flt3 − IL3 $pIC_{50}$ | Ba/F3-flt3 + IL3 $pIC_{50}$ |
|---|---|---|---|
| F-1 | >10 | <5 | <5 |
| F-2 | >10 | <5 | <5 |
| F-3 | >10 | <5 | <5 |
| F-4 | 1 | <5 | <5 |
| F-5 | >10 | <5 | <5 |
| F-6 | 3 | <5 | <5 |
| F-7 | 10 | <5 | <5 |
| F-8 | 5 | <5 | <5 |
| F-9 | 2 | <5 | <5 |
| F-10 | 5 | 5.04 | <5 |
| F-11 | >10 | <5 | <5 |
| F-12 | >10 | <5 | <5 |
| F-13 | 5 | <5 | <5 |
| F-14 | — | — | — |
| F-15 | 10 | <5 | <5 |
| F-16 | >10 | <5 | <5 |
| F-17 | 3 | <5 | <5 |
| F-18 | 5 | <5 | <5 |
| F-19 | 3 | <5 | <5 |
| F-20 | 0.1 | <5 | <5 |
| F-21 | — | — | — |
| F-22 | — | — | — |
| F-24 | >10 | <5 | <5 |
| F-25 | >10 | <5 | <5 |
| F-27 | >10 | <5 | <5 |
| F-29 | >10 | <5 | <5 |
| F-32 | >10 | <5 | <5 |
| F-23 | 5 | <5 | <5 |
| F-28 | 5 | <5 | <5 |
| F-30 | 10 | <5 | <5 |

The invention claimed is:

1. A compound of formula (I):

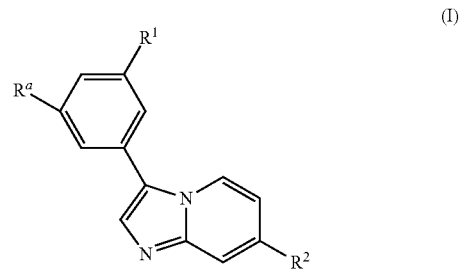

wherein $R^1$ represents —NHCONR$^4$R$^5$ or —NHCSNR$^4$R$^5$ or —NH-heterocyclyl wherein heterocyclyl represents thiadiazolyl or oxadiazolyl, and wherein the heterocyclyl group is optionally substituted by one or more halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^d$, —(CH$_2$)$_n$—O—$C_{1-6}$ alkyl, —O—(CH$_2$)$_n$—OR$^d$, halo$C_{1-6}$ alkyl, halo$C_{1-6}$ alkoxy, $C_{1-6}$ alkanol, =O, =S, nitro, Si(R$^d$)$_4$, —(CH$_2$)$_s$—CN, —S—R$^d$, —SO—R$^d$, —SO$_2$—R$^d$, —COR$^d$, —(CR$^d$R$^e$)$_s$—COOR$^d$, —(CH$_2$)$_s$—CONR$^d$R$^e$, —(CH$_2$)$_s$—NR$^d$R$^e$, —(CH$_2$)$_s$—NR$^d$COR$^e$, —(CH$_2$)$_s$—NR$^d$SO$_2$—R$^e$, —(CH$_2$)$_s$—NH—SO$_2$—

NR$^d$R$^e$, —OCONR$^d$R$^e$, —(CH$_2$)$_s$—NR$^d$CO$_2$R$^e$, —O—(CH$_2$)$_s$—CR$^d$R$^e$—(CH$_2$)$_t$—OR$^f$ or —(CH$_2$)$_s$—SO$_2$NR$^d$R$^e$ groups;

R$_a$ represents C$_{2-4}$alkoxy, haloC$_{2-4}$alkoxy, C$_{1-4}$-alkoxy C$_{1-4}$alkyl, cyclobutoxy, cyclopropoxy, —NH—C$_{1-4}$ alkyl, —N(C$_{1-4}$alkyl)$_2$, —C$_{1-4}$alkyl-NH(C$_{1-4}$alkyl), —C$_{1-4}$alkyl-N(C$_{1-4}$alkyl)$_2$, C$_{1-4}$alkyl-S(=O)$_2$—C$_{1-4}$ alkyl or —S(=O)$_2$—C$_{1-4}$alkyl;

R$^2$ represents —C(=O)—R$^x$, —O—R$^x$ or a 5 or 6-membered heterocyclyl optionally substituted by one or more halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^g$, —(CH$_2$)$_n$—O—C$_{1-6}$ alkyl, —O—(CH$_2$)$_n$—OR$^g$, haloC$_{1-6}$ alkyl, haloC$_{1-6}$ alkoxy, C$_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$-COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_s$—SO$_2$NR$^g$R$^h$ groups;

R$^x$ represents C$_{3-6}$cycloalkyl optionally substituted with hydroxyl or NR'R", or C$_{1-6}$alkyl optionally substituted with hydroxyl or NR'R";

R' and R" each independently represent hydrogen, C$_{1-4}$alkyl or R' and R" taken together with the nitrogen to which they are attached may form a saturated heterocycle selected from piperidinyl, piperazinyl, morpholinyl or thiomorpholinyl;

R$^4$ and R$^5$ each independently represent hydrogen, C$_{1-6}$ alkyl, C$_{2-6}$ alkenyl, C$_{2-6}$ alkynyl, C$_{3-8}$ cycloalkyl, C$_{3-8}$ cycloalkenyl, C$_{1-6}$ alkanol, haloC$_{1-6}$ alkyl, —(CH$_2$)$_n$—NR$^g$R$^h$, —(CH$_2$)$_s$—COOR$^k$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said C$_{1-6}$ alkyl, C$_{2-6}$ alkenyl, C$_{2-6}$ alkynyl, C$_{3-8}$ cycloalkyl, C$_{3-8}$ cycloalkenyl, aryl and heterocyclyl groups may be optionally substituted by one or more R$^P$ groups;

R$^P$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^g$, —(CH$_2$)$_n$—O—C$_{1-6}$ alkyl, —O—(CH$_2$)$_n$—OR$^g$, haloC$_{1-6}$ alkyl, haloC$_{1-6}$ alkoxy, C$_{1-6}$ alkanol, =O, =S, nitro, Si(R$^g$)$_4$, —(CH$_2$)$_s$—CN, —S—R$^g$, —SO—R$^g$, —SO$_2$—R$^g$, —COR$^g$, —(CR$^g$R$^h$)$_s$—COOR$^k$, —(CH$_2$)$_s$—CONR$^g$R$^h$, —(CH$_2$)$_s$—NR$^g$R$^h$, —(CH$_2$)$_s$—NR$^g$COR$^h$, —(CH$_2$)$_s$—NR$^g$SO$_2$—R$^h$, —(CH$_2$)$_s$—NH—SO$_2$—NR$^g$R$^h$, —OCONR$^g$R$^h$, —(CH$_2$)$_s$—NR$^g$CO$_2$R$^h$, —O—(CH$_2$)$_s$—CR$^g$R$^h$—(CH$_2$)$_t$—OR$^k$ or —(CH$_2$)$_s$—SO$_2$NR$^g$R$^h$ groups;

R$^d$, R$^e$ and R$^f$ independently represent hydrogen, C$_{1-6}$ alkyl, C$_{2-6}$ alkenyl, C$_{2-6}$ alkynyl, C$_{1-6}$ alkanol, hydroxy, C$_{1-6}$alkoxy, haloC$_{1-6}$ alkyl, —CO—(CH$_2$)$_n$—C$_{1-6}$ alkoxy, C$_{3-8}$ cycloalkyl, or C$_{3-8}$ cycloalkenyl;

R$^g$, R$^h$ and R$^k$ independently represent hydrogen, C$_{1-6}$ alkyl, C$_{2-6}$ alkenyl, C$_{2-6}$ alkynyl, C$_{1-6}$ alkanol, —COOC$_{1-6}$ alkyl, hydroxy, C$_{1-6}$alkoxy, haloC$_{1-6}$ alkyl, —CO—(CH$_2$)$_n$—C$_{1-6}$alkoxy, C$_{1-6}$alkylamino-, C$_{3-8}$ cycloalkyl, or C$_{3-8}$ cycloalkenyl;

m and n independently represent an integer from 1-4;

s and t independently represent an integer from 0-4;

or a pharmaceutically acceptable salt, tautomer, N-oxide or solvate thereof.

2. A compound as defined in claim 1 wherein R$^1$ represents —NHCONR$^4$R$^5$, or a pharmaceutically acceptable salt, tautomer, N-oxide or solvate thereof.

3. A compound as defined in claim 2 wherein R$^1$ represents —NHCONHCH$_2$CF$_3$, —NHCONHCH$_2$CH$_3$ or NHCONHCH$_2$CH(CH$_3$)$_2$, or a pharmaceutically acceptable salt, tautomer, N-oxide or solvate thereof.

4. A compound as defined in claim 1 wherein R$_a$ represents C$_{2-4}$alkoxy, C$_{1-4}$alkoxyC$_{1-4}$alkyl, cyclobutoxy, —NH—C$_{1-4}$alkyl, —C$_{1-4}$alkyl-NH(C$_{1-4}$alkyl), or —C$_{1-4}$alkyl-N(C$_{1-4}$alkyl)$_2$, or a pharmaceutically acceptable salt, tautomer, N-oxide or solvate thereof.

5. A compound as defined in claim 4 wherein R$^a$ represents C$_{2-4}$alkoxy, cyclobutoxy or C$_{1-4}$alkoxyC$_{1-4}$alkyl, or pharmaceutically acceptable salt, tautomer, N-oxide or solvate thereof.

6. A compound as defined in claim 4 wherein R$^a$ represents —O—CH$_2$—CH$_3$ or —O—CH(CH$_3$)$_2$, or a pharmaceutically acceptable salt, tautomer, N-oxide or solvate thereof.

7. A compound as defined in claim 1 wherein R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more of halogen, C$_{1-6}$alkyl, haloC$_{1-6}$ alkyl, —(CH$_2$)$_s$—NR$^g$R$^h$, C$_{1-6}$alkanol or —(CR$^g$R$^h$)COOR$^k$, or a pharmaceutically acceptable salt, tautomer, N-oxide or solvate thereof.

8. A compound as defined in claim 7 wherein R$^2$ represents —C(=O)—R$^x$ or —O—R$^x$, wherein R$^x$ is C$_{3-6}$cycloalkyl or R$^x$ is C$_{1-6}$alkyl substituted with hydroxyl, or a pharmaceutically acceptable salt, tautomer, N-oxide or solvate thereof.

9. A compound as defined in claim 1 wherein R$^1$ represents NHCONR$^4$R$^5$ and R$^4$ represents hydrogen and R$^5$ represents haloC$_{1-6}$alkyl and R$^a$ represents C$_{2-4}$alkoxy and R$^2$ represents pyrimidinyl, pyridinyl, thiadiazolyl or oxadiazolyl, each of said rings being optionally substituted, or a pharmaceutically acceptable salt, tautomer, N-oxide or solvate thereof.

10. A compound as defined in claim 9 wherein the pyrimidinyl, thiadiazolyl or oxadiazolyl is substituted by one or more, of —CH$_3$, —F, —CF$_3$ and —NH$_2$, or a pharmaceutically acceptable salt, tautomer, N-oxide or solvate thereof.

11. A compound as defined in claim 1 wherein R$^1$ represents NHCONR$^4$R$^5$ and R$^4$ represents hydrogen and R$^5$ represents haloC$_{1-6}$alkyl and R$^a$ represents C$_{2-4}$alkoxy and R$^2$ represents a 5 or 6-membered optionally substituted heterocyclyl, or a pharmaceutically acceptable salt, tautomer, N-oxide or solvate thereof.

12. A compound as defined in claim 11 wherein the heterocyclyl is optionally substituted by one or more of halogen, C$_{1-6}$alkyl, haloC$_{1-6}$alkyl, —(CH$_2$)$_s$—NR$^g$R$^h$, C$_{1-6}$alkanol or —(CR$^g$R$^h$)COOR$^k$, or a pharmaceutically acceptable salt, tautomer, N-oxide or solvate thereof.

13. A compound as defined in claim 11 wherein the heterocyclyl is substituted by one or more of —CH$_3$, —F, —CF$_3$ or —NH$_2$, or a pharmaceutically acceptable salt, tautomer, N-oxide or solvate thereof.

14. A compound as defined in claim 1 wherein:

R$^1$ is —NHCONR$^4$R$^5$ wherein R$^4$ represents hydrogen and R$^5$ represents hydrogen, C$_{1-6}$alkyl optionally substituted with one or more R$^p$ group;

R$^a$ represents C$_{2-4}$alkoxy, C$_{1-4}$alkoxyC$_{1-4}$alkyl, cyclobutoxy, —NH—C$_{1-4}$alkyl, —C$_{1-4}$alkyl-N(C$_{1-4}$alkyl)$_2$ or —C$_{1-4}$alkyl-NH(C$_{1-4}$alkyl); and R$^2$ represents —C(=O)—R$^x$, —O—R$^x$, or a heterocyclyl selected from thiadiazolyl, oxadiazolyl, imidazoyl, piperidinyl, pyridinyl and pyrimidinyl wherein the heterocyclyl is optionally substituted by one or more of halogen, C$_{1-6}$alkyl, haloC$_{1-6}$ alkyl, —(CH$_2$)$_s$—NR$^g$R$^h$, C$_{1-6}$alkanol or —(CR$^g$R$^h$)COOR$^k$;

R$^P$ represents halogen or —OR$^g$;

$R^g$ represents hydrogen;
$R^x$ is $C_{3-6}$cycloalkyl or $R^x$ is $C_{1-6}$alkyl substituted with hydroxyl; and
$R^g$, $R^h$ and $R^k$ are independently selected from hydrogen and $C_{1-6}$alkyl, or a pharmaceutically acceptable salt, tautomer, N-oxide or solvate thereof.
15. A compound as defined in claim 1 which is a compound selected from:
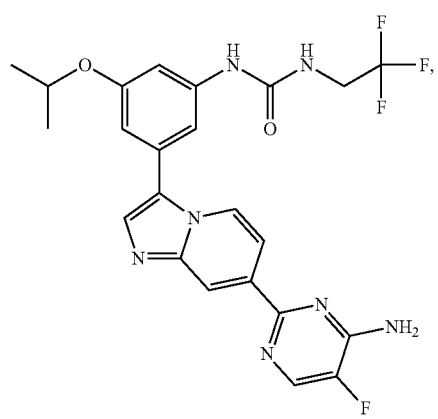
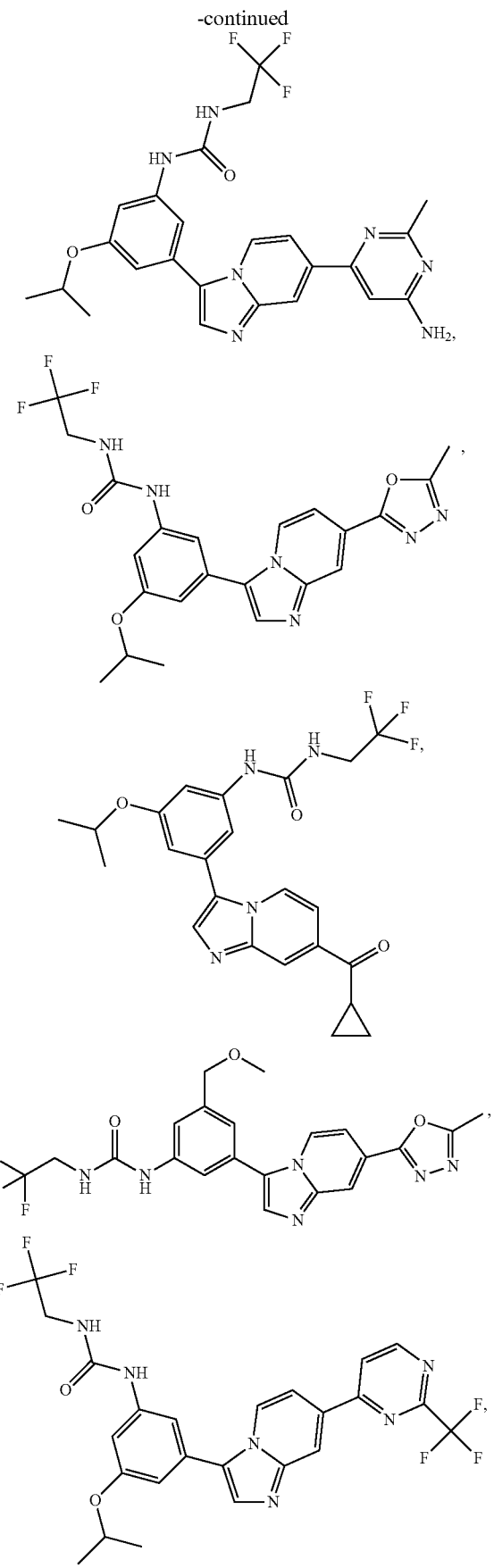

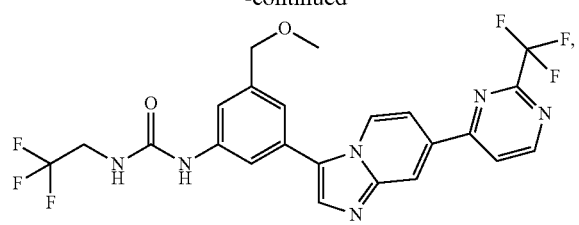
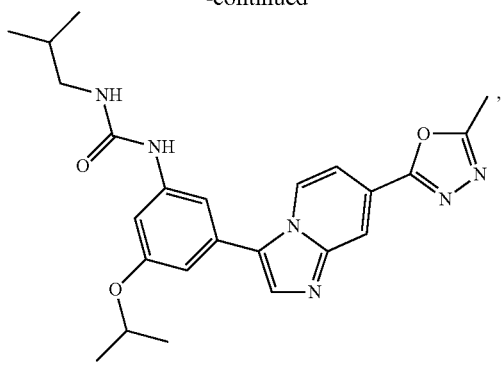
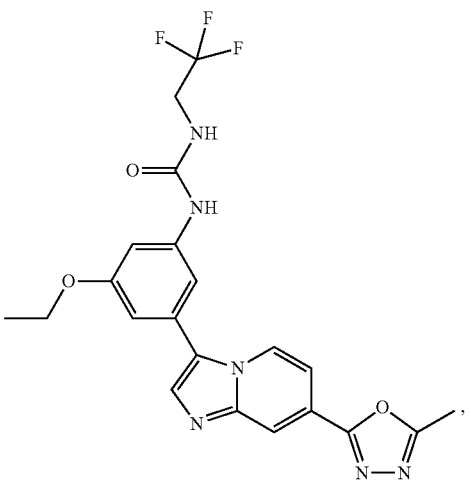
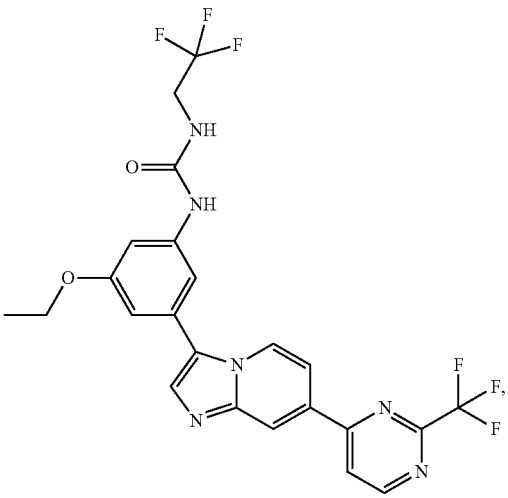

121
-continued
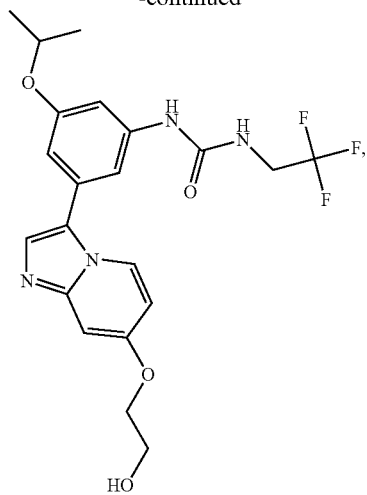
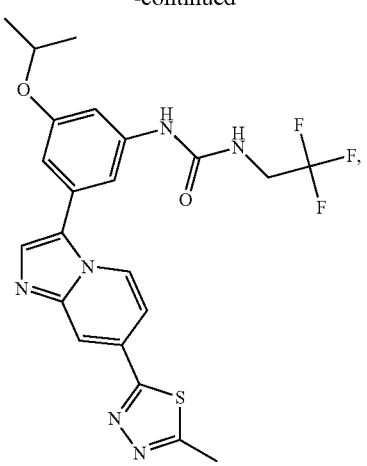
122
-continued
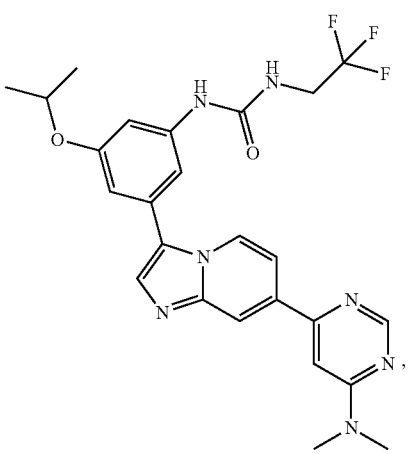
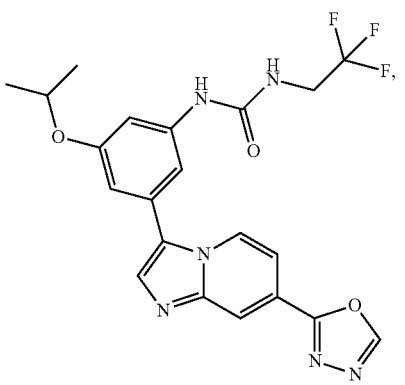
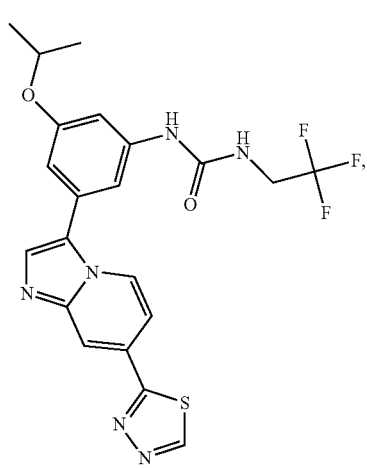
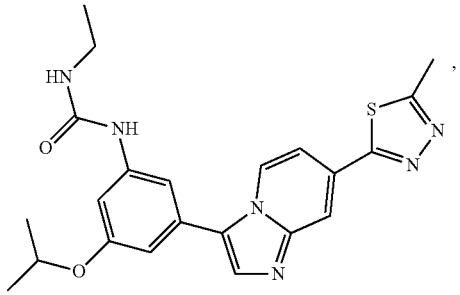

123
-continued

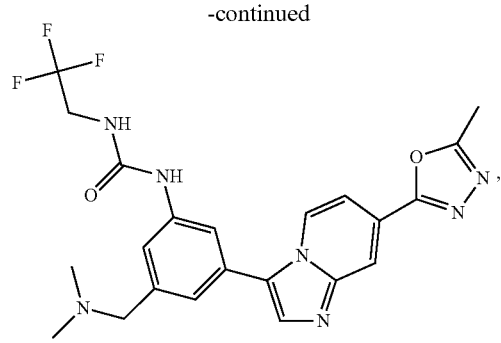

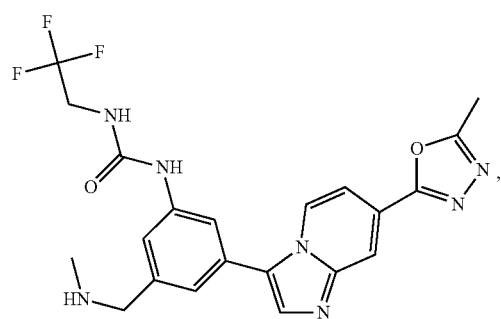

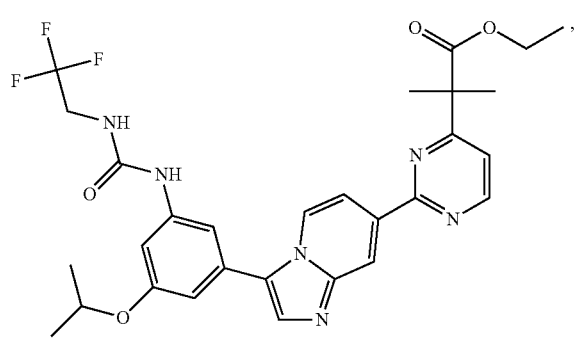

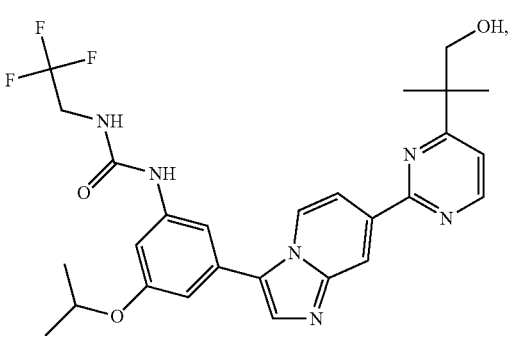

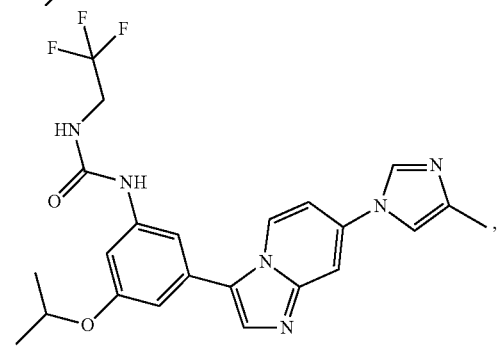

124
-continued

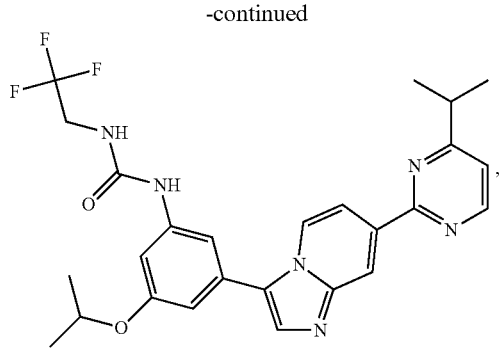

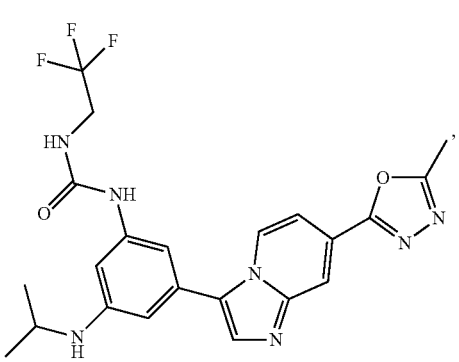

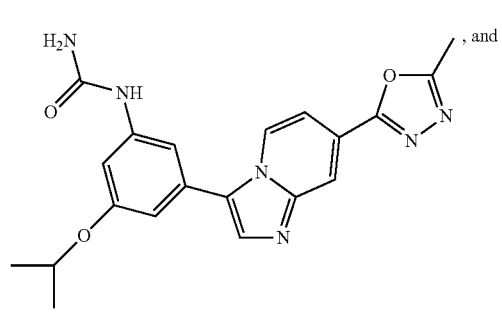

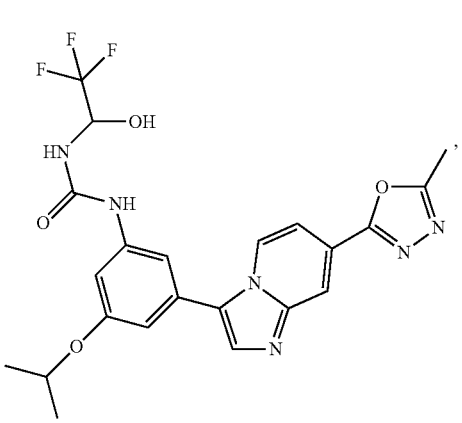 [SMILES: Cc1nnc(-c2ccn3c(-c4cc(NC(=O)NC(O)C(F)(F)F)cc(OC(C)C)c4)cnc3c2)o1]

or a pharmaceutically acceptable salt, tautomer, N-oxide or solvate thereof.

16. A compound as defined in claim 1 or a pharmaceutically acceptable salt or solvate thereof.

17. A process for the preparation of a compound of formula (I) as defined in claim 1, or a pharmaceutically acceptable salt, tautomer, N-oxide or solvate thereof, which process comprises:

(i) the reaction of a compound of the formula (XX):

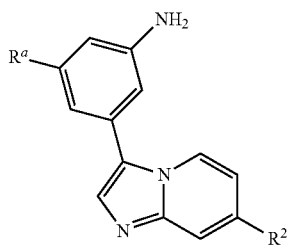

(XX)

or a protected form thereof, wherein $R^a$ and $R^2$ are as defined hereinbefore, with an appropriately substituted isocyanate or an appropriately substituted amine in the presence of carbonyl diimidazole (CDI) and thereafter removing any protecting group present; or (ii) reacting a compound of formula (V) and (VI):

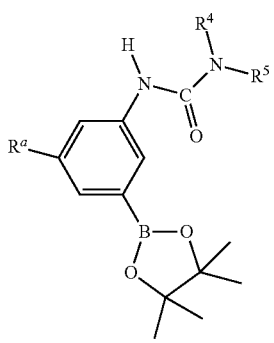

(V)

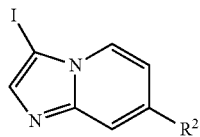 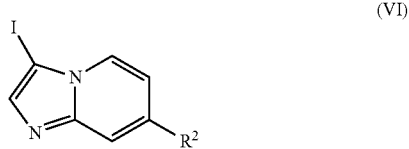

(VI)

wherein $R^a$, $R^2$, $R^4$ and $R^5$ are as defined above for compounds of formula (I) for example, using a Suzuki reaction;

and optionally thereafter converting one compound of the formula (I) into another compound of the formula (I).

18. A pharmaceutical composition comprising a compound of formula (I) as defined in claim 1, or a pharmaceutically acceptable salt, tautomer, N-oxide or solvate thereof.

19. A method for the treatment of cancer, wherein the cancer is mediated by a FGFR kinase, which method comprises administering to a subject suffering from, or being at risk of suffering from the cancer, a compound of the formula (I) as defined in claim 1 or a pharmaceutically acceptable salt, tautomer, N-oxide or solvate thereof.

20. A method of inhibiting a FGFR kinase, which method comprises contacting the kinase with a compound of the formula (I) as defined in claim 1, or a pharmaceutically acceptable salt, tautomer, N-oxide or solvate thereof.

\* \* \* \* \*